United States Patent
Wong et al.

(10) Patent No.: US 12,384,811 B2
(45) Date of Patent: Aug. 12, 2025

(54) SIALIDASE-RESISTANT SACCHARIDE AND METHOD OF MAKING AND USING THE SAME

(71) Applicant: Academia Sinica, Taipei (TW)

(72) Inventors: Chi-Huey Wong, Rancho Santa Fe, CA (US); Hong-Jay Lo, New Taipei (TW)

(73) Assignee: Academia Sinica, Taipei (TW)

( * ) Notice: Subject to any disclaimer, the term of this patent is extended or adjusted under 35 U.S.C. 154(b) by 981 days.

(21) Appl. No.: 17/598,064

(22) PCT Filed: Mar. 10, 2020

(86) PCT No.: PCT/US2020/014608
§ 371 (c)(1),
(2) Date: Sep. 24, 2021

(87) PCT Pub. No.: WO2020/205034
PCT Pub. Date: Oct. 8, 2020

(65) Prior Publication Data
US 2022/0267363 A1    Aug. 25, 2022

Related U.S. Application Data

(60) Provisional application No. 62/829,736, filed on Apr. 5, 2019.

(51) Int. Cl.
*C07H 15/18* (2006.01)
*C07H 1/00* (2006.01)
*C07K 16/28* (2006.01)

(52) U.S. Cl.
CPC .............. *C07H 15/18* (2013.01); *C07H 1/00* (2013.01); *C07K 16/283* (2013.01); *C07K 16/2887* (2013.01); *C07K 2317/24* (2013.01); *C07K 2317/41* (2013.01); *C07K 2317/92* (2013.01)

(58) Field of Classification Search
None
See application file for complete search history.

(56) References Cited

U.S. PATENT DOCUMENTS

| 7,871,626 | B2 | 1/2011 | Hoffmann et al. |
| 10,301,377 | B2 | 5/2019 | Graham et al. |
| 10,906,944 | B2 | 2/2021 | He et al. |

(Continued)

FOREIGN PATENT DOCUMENTS

| CN | 105934441 A | 9/2016 |
| CN | 112626124 A | 4/2021 |

(Continued)

OTHER PUBLICATIONS

Okamoto, K. et al. Tetrahedron Letters, 1986, vol. 27, No. 43, pp. 5233-5236 (Year: 1986).*

(Continued)

*Primary Examiner* — Karl J Puttlitz
(74) *Attorney, Agent, or Firm* — Prosyla Group PC

(57) ABSTRACT

Disclosed are a method of preparing a saccharide that contains a 3-fluoro-sialic acid and a method of bonding it to a homogeneous antibody. Also within the scope of this invention are compounds each containing a 3-fluoro-sialic acid, monoclonal antibodies bonded to α2,6-linked 3-fluoro-sialo-side terminated N-glycans, and treatment of cancer with such monoclonal antibodies.

7 Claims, 3 Drawing Sheets

(56) References Cited

U.S. PATENT DOCUMENTS

| | | |
|---|---|---|
| 10,953,089 B1 | 3/2021 | Smith et al. |
| 10,954,289 B1 | 3/2021 | Babb et al. |
| 11,480,391 B2 | 10/2022 | Wong et al. |
| 11,866,485 B2 | 1/2024 | Lin et al. |
| 11,918,641 B2 | 3/2024 | Wong |
| 11,992,525 B2 | 5/2024 | Wong et al. |
| 12,085,340 B2 | 9/2024 | Wong et al. |
| 2006/0073542 A1 | 4/2006 | Bayer et al. |
| 2010/0041740 A1 | 2/2010 | Wong et al. |
| 2010/0247571 A1 | 9/2010 | Wong et al. |
| 2013/0309176 A1 | 11/2013 | Port et al. |
| 2014/0107049 A1 | 4/2014 | Bennani et al. |
| 2015/0132330 A1 | 5/2015 | Garcia-Sastre et al. |
| 2016/0199481 A1 | 7/2016 | Bloom |
| 2016/0376321 A1 | 12/2016 | Hotez et al. |
| 2018/0043007 A1 | 2/2018 | LeFebvre et al. |
| 2019/0388460 A1 | 12/2019 | Hedrick et al. |
| 2020/0046826 A1 | 2/2020 | Wong et al. |
| 2020/0078452 A1 | 3/2020 | Wong et al. |
| 2020/0079808 A1 | 3/2020 | Pfister et al. |
| 2020/0231633 A1 | 7/2020 | Berman et al. |
| 2020/0283743 A1 | 9/2020 | Zhang et al. |
| 2021/0017563 A1 | 1/2021 | Bhatnagar et al. |
| 2021/0207106 A1 | 7/2021 | Anthony et al. |
| 2021/0316002 A1 | 10/2021 | Ellis |
| 2022/0233713 A1 | 7/2022 | Callan et al. |
| 2023/0000741 A1 | 3/2023 | Wong et al. |
| 2023/0074185 A1 | 3/2023 | Wong et al. |
| 2023/0105209 A1 | 4/2023 | Lin et al. |
| 2023/0002790 A1 | 9/2023 | Lin et al. |
| 2023/0279080 A1 | 9/2023 | Lin et al. |
| 2024/0016917 A1 | 1/2024 | Ma et al. |
| 2024/0066113 A1 | 2/2024 | Wong et al. |
| 2024/0100147 A1 | 3/2024 | Wong et al. |
| 2024/0228591 A1 | 7/2024 | Lin et al. |
| 2024/0366516 A1 | 11/2024 | Wong et al. |
| 2024/0366517 A1 | 11/2024 | Wong et al. |
| 2024/0384320 A1 | 11/2024 | Wong et al. |
| 2025/0041222 A1 | 2/2025 | Wong et al. |

FOREIGN PATENT DOCUMENTS

| | | |
|---|---|---|
| CN | 116478948 A | 7/2023 |
| EP | 1987068 A1 | 11/2008 |
| EP | 2949665 A1 | 12/2015 |
| JP | 2012530499 A | 12/2012 |
| JP | 2017518989 A | 7/2017 |
| RU | 2720614 C1 | 5/2020 |
| RU | 2730897 C1 | 8/2020 |
| WO | 2004099240 A2 | 11/2004 |
| WO | 2004099240 A3 | 11/2004 |
| WO | 2007008918 A2 | 1/2007 |
| WO | 2007095506 A1 | 8/2007 |
| WO | 2009002516 A1 | 12/2008 |
| WO | 2009007427 A2 | 1/2009 |
| WO | 2010022737 A1 | 3/2010 |
| WO | 2010111687 A2 | 9/2010 |
| WO | 2010148511 A1 | 12/2010 |
| WO | 2011115862 A1 | 9/2011 |
| WO | 2012054907 A2 | 4/2012 |
| WO | 2012088428 A1 | 6/2012 |
| WO | 2013043729 A1 | 3/2013 |
| WO | 2013067652 A1 | 5/2013 |
| WO | 2014115797 A1 | 7/2014 |
| WO | 2015057942 A1 | 4/2015 |
| WO | 2015073727 A1 | 5/2015 |
| WO | 2015176662 A1 | 11/2015 |
| WO | WO-2015/184004 A1 | 12/2015 |
| WO | 2017062496 A2 | 4/2017 |
| WO | WO2017081082 A2 | 5/2017 |
| WO | 2018089407 | 11/2017 |
| WO | 2018089407 A1 | 5/2018 |
| WO | 2019028190 A1 | 2/2019 |
| WO | 2015028478 A1 | 6/2019 |
| WO | 2019246363 A1 | 12/2019 |
| WO | 2020011275 A1 | 1/2020 |
| WO | 2020058239 A1 | 3/2020 |
| WO | WO2020205034 | 3/2020 |
| WO | 2019246363 | 4/2020 |
| WO | 2020172072 A1 | 8/2020 |
| WO | 2020198865 A1 | 10/2020 |
| WO | 2021019102 A2 | 2/2021 |
| WO | 2021035325 A1 | 3/2021 |
| WO | 2021045632 A1 | 3/2021 |
| WO | 2021045836 A1 | 3/2021 |
| WO | 2021226533 | 5/2021 |
| WO | 2021174128 A1 | 9/2021 |
| WO | 2021180602 A1 | 9/2021 |
| WO | 2021183195 A1 | 9/2021 |
| WO | 2021186028 A1 | 9/2021 |
| WO | 2021214204 A1 | 10/2021 |
| WO | 2021219897 A1 | 11/2021 |
| WO | 2021233989 A1 | 11/2021 |
| WO | 2021257586 A1 | 12/2021 |
| WO | 2022047401 A1 | 3/2022 |
| WO | 2022221835 | 4/2022 |
| WO | 2022221837 | 4/2022 |
| WO | 2022221835 A2 | 10/2022 |
| WO | 2023056482 | 10/2022 |
| WO | 2022227927 A1 | 11/2022 |
| WO | 2022229854 A1 | 11/2022 |
| WO | 2023129928 | 12/2022 |
| WO | 2023021111 A1 | 2/2023 |
| WO | 2023056482 A1 | 4/2023 |
| WO | 2023069551 A1 | 4/2023 |
| WO | 2023129928 A2 | 7/2023 |
| WO | 2024215614 A2 | 10/2024 |
| WO | 2024215616 A2 | 10/2024 |
| WO | PCTUS2460715 | 12/2024 |

OTHER PUBLICATIONS

Chokhawala, H. A. et al. J. Am. Chem. Soc., 2007, vol. 129, No. 35, pp. 10630-10631 (Year: 2007).*

Kurzawa, Synlett 2015, 26, 1422-1423 (Year: 2015).*

Doboszewski et al., 1987, Canadian Journal of Chemistry. 65(2): 412-419 (Year: 1987).*

Bennua-Skalmowski et al., Tetrahedron Letters, vol. 36, No. 15, pp. 2611-2614, 1995 (Year: 1995).*

Lo et al., J. Am. Chem. Soc. 2019, 141, 6484-6488 (Year: 2019).*

Chokhawala et al "Enzymatic Synthesis of Fluorinated Mechanistic Probes for Sialidases and Sialyltransferases" Journal of the American Chemical Society vol. 129, pp. 10630-10631, 2007.

Hayashi et al "Stereospecific a-Sialylation by Site-Selective Fluorination" Angewandte Chemie International Edition vol. 58, pp. 3814-3818, 2019.

Lo et al "Synthesis of Sialidase-Resistant Oligosaccharide and Antibody Glycoform Containing α2,6-Linked 3F $^{ax}$-Neu5Ac" Journal of the American Chemical Society vol. 141, pp. 6484-6488, 2019.

Okamoto et al "An Effective Synthesis of α-Glycosides of N-Acetylneuraminic Acid by Use of 2β-Halo-3β-Hydroxy-4,7,8,9-Tetra-O-Acetyl-N-Acetylneuraminic Acid Methyl Ester" Tetrahedron Letters vol. 27, pp. 5233-5236, 1986.

Castrucci, M.R. et al., "Biologic importance of neuramindase stalk length in influenza A virus", Journal of Virology, 1993, vol. 67, No. 2, pp. 759-764.

Dowling, W. et al., "Influences of Glycosylation on Antigenicity, Immunogenicity, and Protective Efficacy of Ebola Virus GP DNA Vaccines", J. of Virology, 2007, vol. 81, No. 4, pp. 1821-1837, p. 1822, second column, fourth paragraph; p. 1823, second column, third paragraph; doi:10.1128/JVI.02098-06.

Feng et al., "A Glycolipid Adjuvant, 7DW8-5, Enhances the Protective Immune Response to the Current Slpit Influenza Vaccine in Mice", Frontiers in Microbiology, Sep. 18, 2019, vol. 10, No. 2157M, pp. 1-9; abstract.

Galili, "Amplifying immunogenicity of prospective Covid-19 vaccines by glycoengineering the coronavirus glycan-shield to present alpha-gal epitopes", Vaccine, Aug. 19, 2020; abstract; Fig. 1; DOI: 10.1016/j.vaccine.2020.08032.

(56) References Cited

OTHER PUBLICATIONS

GenBank Accession CCH23214, haemagglutinin [Influenza A virus (A/WSN/1933(H1N1))], 2013.
GenBank Accession, ACF54601, neuraminidase [Influenza A virus (A/WSN/1933(H1N1))], 2008.
Gillian, M. Air, "Influenza neuraminidase", Influenza and Other Respiratory Viruses, 2011.
Hughes et al., "Adaptation of Influenza A Viruses to Cells Expressing Low Levels of Sialic Acid Leads to Loss of Neuraminidase Activity", Journal of Virology, 2001, vol. 75, No. 8, pp. 3766-3770.
Li, et al., Glycosylation of Neuraminidase Determines the Neurovirulence of Influenza A/WSN/33 Virus, 1993, Journal of Virology, vol. 67, No. 11, pp. 6667-6673.
Liu, Wen-Chun et al., "Unmasking Stem-Specific Neutralizing Epitopes by Abolishing N-Linked Glycosylation Sites of Influenza Virus Hemagglutinin Proteins for Vaccine Design", Journal of Virology, vol. 90 No. 19, Oct. 2016.
Medina, Rafael A. et al., "Glycosylations in the globular head of the hemagglutinin protein modulate the virulence and antigenic properties of the H1N1 influenza viruses", Sci Transl Med., May 29, 2013.
Nobusawa et al., "Comparison of Complete Amino Acid Sequences and Receptor-Binding Properties among 13 Serotypes of Hemagglutinins of Influenza A Viruses", Virology, 182, 475-485 (1991).
Rahman, M Shaminur et al., "Epitope-based chimeric peptide vaccine design against S, M, and E proteins of SARS-CoV-2, the etiologic agent of COVID-19 pandemic, an in silico approach", PeerJ, Jul. 27, 2020 (publication date), DOI 10.7717/peerj.9572, Internal pp. 1-30, Supplemental Information pp. 1, 2. Abstract; and supplemental information pp. 1, 2.
Roberts, Paul C. et al., "Role of Conserved Glycosylation Sites in Maturation and Transport of Influenza A Virus Hemagglutinin", Journal of Virology, Jun. 1993, p. 3048-3060.
Sun et al., "N-Linked Glycosylation of the Hemagglutinin Protein Influences Virulence and Antigenicity of the 1918 Pandemic and Seasonal H1N1 Influenza A Viruses", 2013, Journal of Virology, vol. 87, No. 15, pp. 8756-8766.
Wu, Chung-Yi et al., "Influenza A surface glycosylation and vaccine design", PNAS, Jan. 2017, (Epub Dec. 27, 2016), vol. 114, No. 2, pp. 280-285.
Yang, Zhiwei et al., "Mutation effects of neuraminidases and their docking with ligands: a molecular dynamics and free energy calculation study", J Comput Aided Mol Des, 27: 935-950, 2013.
Zaraket, Hassan et al., "Full Genome Characterization of Human Influenza A/H3N2 Isolates from Asian Countries Reveals a Rare Amantadine Resistance-Conferring Mutation and Novel PB1-F2 Polymorphisms", Frontiers in Microbiology, vol. 7, Article 262, Mar. 2016.
Zhang, Xiaojian et al., "Role of stem glycans attached haemagglutinin in the biological characteristics of H5N1 avian influenza virus", Journal of General Virology, 96, 1248-1257, 2015.
Zhang, Yan et al., "Glycosylation on Hemagglutinin Affects the Virulence and Pathogenicity of Pandemic H1N1/2009 Influenza A Virus in Mice", PLOS One, vol. 8, Issue 4, Apr. 2013.
Zhao, "Glycans of SARS-CoV-2 Spike Protein in Virus Infection and Antibody Production", Frontiers in Molecular Biosciences, Apr. 13, 2021; Entire Document; DOI: 10.3389/fmolb.2021.629873.
Zheng, J. et al., "Identification of N-linked glycosylation sites in the spike protein and their functional impact on the replication and infectivity of coronavirus infectious bronchitis virus in cell culture", Virology, Oct. 13, 2017, vol. 513, pp. 65-74; abstract; p. 65, 1st column, second paragraph; p. 66, col. 5th paragraph; p. 68, first column, first, third paragraphs; Table 3; figure 5; http://dx.doi.org/10.1016/j.virol.2017.10.003.
Davies, Nicholas G. et al., "Estimated transmissibility and impact of SARS-CoV-2 lineage B.1.1.7 in England," Science, Apr. 2021, vol. 372, pp. 149 (10 pages).
Focosi, Daniele, "Neutralising antibody escape of SARS-CoV-2 spike protein: Risk assessment for antibody-based Covid-19 therapeutics and vaccines," Rev. Med Virol., 2021, vol. 31, 21 pp. e2231.
GenBank accession MN908947.3, Mar. 18, 2020, 11 pages. (https://www.ncbi.nlm.nih.gov/nuccore/MN908947).
Magazine, Nicholas et al., "Mutations and Evolution of the SARS-COV-2 Spike Protein," Viruses, 2022, vol. 14, 640, 11 pgs.
Office Action and Search Report issued in Taiwan Patent Application No. 111113933 on Mar. 26, 2024. English translation of search report.
Watanabe, Yasunori et al., "Site-specific glycan analysis of the SARS-CoV-2 spike," Science, Jul. 2020, vol. 369, pp. 330-333.
Bosch, Berend Jan et al.,"Coronavirus Escape from Heptad Repeat 2 (HR2)-Derived Peptide Entry Inhibition as a Result of Mutations in the HR1 Domain of the Spike Fusion Protein," J of Virol., Mar. 2008, vol. 82, No. 5, pp. 2580-2585.
Galili, Uri, "Amplifying immunogenicity of prospective Covid-19 vaccines by glycoengineering the coronavirus glycan-shield to present [alpha]-gal epitopes," Vaccine, 2020, vol. 38, pp. 6487-6499.
GenBank Accession BCN86353.1 accessed on Jan. 22, 2021. https://www.ncbi.nlm.nih.gov/protein/BCN86353.1?report=genbank&log$=protalign&blast_rank=2&RID=EYKWWEAA016.
GenBank: QLB39105.1 accessed on Jan. 1, 2020. https://www.ncbi.nlm.nih.gov/protein/QLB39105.1?report=genbank&log$=protalign&blast_rank=1&RID=EYKWWEAA016.
GenBank: QTA38985.1 accessed Mar. 21, 2021. https://www.ncbi.nlm.nih.gov/protein/QTA38985.1?report=genbank&log$=protalign&blast_rank=3&RID=EYKWWEAA016.
International Search Report and Written Opinion issued on Jun. 22, 2023 in International Patent Application No. PCT/US22/82428.
Official Action, dated Aug. 31, 2023, received in Russia Patent Application No. 2023100504. English translation provided.
Search Report, dated Aug. 31, 2023, received in Russia Patent Application No. 2023100504.
Tai, Wanbo et al., "Characterization of the receptor-binding domain (RBD) of 2019 novel coronavirus: implication for development of RBD protein as a viral attachment inhibitor and vaccine," Cell Mol Immunol. Jun. 2020;17(6):613-620 https://pubmed.ncbi.nlm.nih.gov/32203189/.
Tian, Jing-Hui et al., "SARS-CoV-2 spike glycoprotein vaccine candidate NVX-CoV2373 immunogenicity in baboons and protection in mice," Nature Communications, 2021, 14 pages. Downloaded Sep. 27, 2023: https://doi.org/10.1038/s41467-020-20653-8.
Weissman, Drew et al., "D614G Spike Mutation Increases Sars CoV-2 Susceptibility to Neutralization," Cell Host & Microbe, Jan. 13, 2021, vol. 29, pp. 23-31 (e1-e4).
Bernstein, David et al., "Immunogenicity of chimeric haemagglutinin-based, universal influenza virus vaccine candidates: interim results of a randomized, placebo-controlled, phase 1 clinical trial", The Lancet Infectious Disease, Elsevier, Amerstdam, NL, vol. 20, No. 1, Oct. 17, 2019, pp. 80-91, XP085982810. ISSN: 1473-3099, DOI: 10.1016/S1473-3099(19)30393-7.
Galili, Uri, "COVID-19 variants as moving targets and how to sop them by glycoengineered whole-virus vaccines," Virulence, 12:1, 1717-1720, DOI:10.1080/21505594.2021.1939924. (https://doi.org/10.1080/21505594.2021.1939924).
GenBank Accession: QHD43416.1, (Mar. 18, 2020) [Described in the Office Action as Appendix A] (Year: 2020).
Huang et al., "Impact of glycosylation on SARS-CoV-2 infection and broadly protective vaccine design," BioRxiv, May 25, 2021, DOI: https://doi.org/10.1101/2021.05.25.445523, internal pp. 1-48.
Watanabe, Yasunori et al., "Exploitation of glycosylation in enveloped virus pathobiology," BBA—General Subjects 1863, 2019), pp. 1480-1497.
Cao, Yiwei et al., "Dynamic Interactions of Fully Glycosylated SARS-CoV-2 Spike Protein with Various Antibodies," JCTC, Sep. 16, 2021, vol. 17, pp. 6559-6569.
Edwards, et al., "The Remarkable Flexibility of the Human Antibody Repertoire; Isolation of Over One Thousand Different Antibodies to a Single Protein, BLyS," J. Mol. Biol., Nov. 2003, 14:334(1):103-18; doi: 10.1016/jmb.2003.09.054. PMID 14596803.
Goel, Manisha et al., "Plasticity within the Antigen-Combining Site May Manifest as Molecular Mimicry in the Humoral Immune Response," J. Immunol., Dec. 15, 2004, 173(12):7358-67 PMID: 15585860 DOI: 10.4049/jimmunol.173.12.7358.

(56) References Cited

OTHER PUBLICATIONS

Janeway Jr., Charles A et al., "Immunobiology: The Immune System in Health and Disease," 3rd edition, Garland Publishing Inc., 1997, pp. 3:1-3:11.

Kanyavuz, Alexia et al., "Breaking the law: unconventional strategies for antibody diversification," Nat Rev Immunol., Jun. 2019, 19(6):355-368. doi:10.1038/S41577-019-0126-7. PMID: 30718829.

Lescar et al., "Crystal Structure of a Cross-reaction Complex between Fab F9.13.7 and Guinea Fowl Lysozyme," J Biol Chem., Jul. 1995, 270(30):18067-76. doi: 10.1074/jbc.270.30.18067. PMID: 7629116.

Lloyd, C. et al., "Modelling the human immune response: performance of a 10(11) human antibody repertoire against a broad panel of therapeutically relevant antigens," Protein Engineering Design & Selection, 2009, vol. 22, No. 3, pp. 159-168. doi: 10.1093/protein/gzn058.

Non-Final Office Action issued in U.S. Appl. No. 17/937,744 dated Jul. 5, 2023.

Rees-Spear, Chloe et al., "The effect of spike mutations on SARS-CoV-2 neutralization," Cell Rep., Mar. 2023, 34 (12): 108890. Published online Mar. 6, 2021. doi: 10.1016/j.celrep.2021.108890: 10.1016/j.celrep.2021.108890 PMCID: PMC7936541 PMID: 33713594.

Rudikoff et al., "Single amino acid substitution altering antigen-binding specificity," Proc. Natl Acad Sci U S A, Mar. 1982, vol. 79(6), pp. 1979-1983. doi: 10.1073/pnas.79.6.1979. PC/D: 6804947.

U.S. Appl. No. 17/598,064, filed Sep. 24, 2021, Chi-Huey Wong.
U.S. Appl. No. 18/029,758, filed Mar. 31, 2023, Chi-Huey Wong.
U.S. Appl. No. 18/501,578, filed Nov. 3, 2023, Chi-Huey Wong.
U.S. Appl. No. 63/266,008, filed Dec. 27, 2021, Kuo-I Lin.
U.S. Appl. No. 63/458,102, filed Apr. 8, 2023, Chi-Huey Wong.
U.S. Appl. No. 63/581,389, filed Sep. 8, 2023, Chi-Huey Wong.

Dang, Juanjuan et al., "Multivalency-assisted membrane-penetrating siRNA delivery sensitizes photothermal ablation via inhibition of tumor glycolysis metabolism," Biomaterials, vol. 223, Dec. 2019, 119463.

Lostalé-Seijo, Irene and Montenegro, Javier, "Synthetic materials at the forefront of gene delivery," Nature Reviews Chemistry, vol. 2, Sep. 21, 2018, pp. 258-277.

Office Action issued in Taiwan Patent Application No. 111113932 on Oct. 16, 2023.

Office Action issued on Nov. 14, 2022, in Israel Patent Application No. 293502.

Sanda, Miloslav et al., "N- and O-Glycosylation of the SARS-CoV-2 Spike Protein," Anal. Chem., vol. 93, No. 4, Jan. 7, 2021, pp. 2003-2009.

Torres-Vanegas, Julian D., "Delivery Systems for Nucleic Acids and Proteins: Barriers, Cell Capture Pathways and Nanocarriers," Pharmaceutics, vol. 13, No. 3, Mar. 22, 2021, pp. 428.

Vogel, Annette B. et al. "BNT162b vaccines protect rhesus macaques from SARS-CoV-2," Nature, vol. 592, Feb. 1, 2021, pp. 283-289.

Alam, MM et al., "Glycan-Modified Virus-Like Particles Evoke T Helper Type 1-Like Immune Responses," ACS Nano, vol. 15, No. 1, Jan. 26, 2021, published online Aug. 17, 2020, doi: 10.1021/acsnano.0c03023, pp. 309-321; (p. 19, figure 1b).

Avinash, MB et al., "Nanoarchitectonics of biomolecular assemblies for functional applications," Nanoscale, vol. 6, No. 22, Nov. 21, 2014, doi: 10.1039/c4nr04340e, pp. 13348-13369. (p. 18, figure 13c).

Bej, Raju et al., "Disulfide chemistry in responsive aggregation of amphiphilic systems," Royal Society of Chemistry, 2020, vol. 16, pp. 11-26. DOI: 10.1039/C9SM01960J.

Bellato, Frederica, "Targeting dendritic cells with mannosylated cationic glycopolymers for nucleic acid-mediated cancer immunotherapy," UNITesi, Magazzini Digitali, 2019, 25 pages. (https://tesidottorato.depositolegale.it/handle/20.500.14242/98191).

Chokhawala, Harshal A. et al., "Enzymatic Synthesis of Fluorinated Mechanistic Probes for Sialidases and Sialyltransferases," JACS Communications, 2007, vol. 129, pp. 10630-10631.

Definition of hemagglutinin [Influenza A virus (A/chicken/Jembrana/BPPV6/2004(H5N1))]. GenBank: ABE97562.1. https://www.ncbi.nlm.nih.gov/protein/ABE97562.1?report=genbank&log$=prottop&blast_rank=1&RID=CGUK0N57013.
Definition of hemagglutinin [Influenza A virus (A/Singapore/GP4444/2010(H1N1))]. GenBank: AEH59357.1. https://www.ncbi.nlm.nih.gov/protein/AEH59357.1?report=genbank&log$=prottop&blast_rank=1&RID=CGTA0JCD016.
Fan, CY et al., "Synthesis of Dendritic Cell-Targeted Polymeric Nanoparticles for Selective Delivery of mRNA Vaccines to Elicit Enhanced Immune Responses," bioRxiv, Epub: Nov. 14, 2023; pp. 1-12; entire document; DOI: 10.1101/2023.11.13.566827.
Huang, Han-Yi et al., "Vaccination with SARS-CoV-2 spike protein lacking glycan shields elicits enhanced protective responses in animal models," Sci. Transl. Med., vol. 14, eabm0899, (2022), 13 pages.
Krammer, Florian et al., "Chimeric Hemagglutinin Influenza Virus Vaccine Constructs Elicit Broadly Protective Stalk-Specific Antibodies," Journal of Virology, Jun. 2013, vol. 87, No. 12, pp. 6542-6550.
Wang, Shih-Chi et al., "Development of a universal influenza vaccine using hemagglutinin stem protein produced from Pichia pastoris," Virology, 2019, vol. 526, pp. 125-137.
Yang et al., "Glucoproteomic Characterization of FUT8 Knock-Out Cells Reveals Roles of FUT8 in the Glycosylation," Frontiers in Chemistry, Oct. 28, 2021, vol. 9, No. 755238, pp. 1-9, entire document.
Bang, Eun-Kyoung et al., JACS, 2013, vol. 135, pp. 2088-2091. dx.doi.org/10.1021/ja311961k.
Byrne et al., "CRISPR/Cas9 gene editing for the creation of an MGAT1-deficient CHO cell line to control HIV-1 vaccine glycosylation," PLOS Biology, 2018, vol. 16, No. 8: e2005817.
Chuard, Nicolas et al., "Cell-penetrating poly(disulfide)s: the dependence of activity, depolymerization kinetics and intracellular localization on their length," Organic & Biomolecular Chemistry, 2015, vol. 13, pp. 64-67.
Ding, Li et al., "A *Photobacterium* sp. [alpha]2-6-sialyltransferase (Psp2,6ST) mutant with an increased expression level and improved activities in sialylating Tn antigens," Carbohydrate Research, 2014, vol. 408, 127-133 (7 pages).
Engdahl, Cecilia et al., "Estrogen induces St6gal1 expression and increases IgG sialylation in mice and patients with rheumatoid arthritis: a potential explanation for the increased risk of rheumatoid arthritis in postmenopausal women," Arthritis Research & Therapy, 2018, vol. 20:84 (11 pages).
Geisler, Christoph et al., "Engineering [beta]1,4-galactosyltransferase I to reduce secretion and enhance N-glycan elongation in insect cells," Journal of Biotechnology, 2015, vol. 193, 52-65 (14 pages).
GenBank Accession NCBI No. QHD43416.1 (surface glycoprotein [Severe acute respiratory syndrome coronavirus 2]; published Mar. 18, 2020.
GenBank Accession No. nC_048600.1 (*Cricetulus griseus* strain 17A/GY chromosome 7, alternate assembly CriGri-PICRH-1.0, whole genome shotgun sequence. Jul. 12, 2020.
Gong, Yanqiu et al., "The glycosylation in SARS-CoV-2 and its receptor ACE2," Signal Transduction and Targeted Therapy, 2021, vol. 6, 396 (24 pages).
Goswami, Roshan et al., "Conjugation of Mannans to Enhance the Potency of Liposome Nanoparticles for the Delivery of RNA Vaccines," Pharmaceutics, 2021, vol. 13, 240, 13 pages.
Grant, Oliver C. et al., "Analysis of the SARS-CoV-2 spike protein glycan shield reveals implications for immune recognition," Scientific Reports, 2020, vol. 10, 14991. https://doi.org/10.1038/s41598-020-71748-7.
Gutierrez Reyes, Cristian D., et al. "N-Glycome Profile of the Spike Protein S1: Systemic and Comparative Analysis from Eleven Variants of SARS-CoV-2," Biomolecules, 2023, vol. 13, pp. 1421 (17 pages).
Hombu, Ryoma et al., "Cellular and Molecular Engineering of Glycan Sialylation in Heterologous Systems," Molecules, 2021, vol. 26, 5950 (27 [ages).

(56) References Cited

OTHER PUBLICATIONS

Huang et al., "Vaccination with SARS-CoV-2 spike protein lacking glycan shields elicits enhanced protective responses in animal models," Sci Transl Med., Apr. 6, 2022, vol. 14(639):eabm0899.

Levit, Mariia et al., "Bio-Inspired Amphiphilic Block-Copolymers Based on Synthetic Glycopolymer and Poly(Amino Acid) as Potential Drug Delivery Systems," Polymers, 2020, vol. 12, pp. 183 (27 pages). doi:10.3390/polym12010183.

Pappalardo, Juan Sebastian et al., "Characterization of a Nanovaccine Platform Based on an [alpha]1,2-Mannobiose Derivative Shows Species-non-specific Targeting to Human, Bovine, Mouse, and Teleost Fish Dendritic Cells," Molecular Pharmaceutics, 2021, vol. 18, 2540-2555.

Shin et al., "CRISPR/Cas9 targeting events cause complex deletions and insertions at 17 sites in the mouse genome," Nature Communications, 2017, vol. 8, Art. 15464.

Shivatare, Vidya et al., "Study on antibody Pc-glycosylation for optimal effector functions," Chem Commun (Camb), 2024, vol. 59, iss. 37, pp. 5555-5558. doi:10.1039/d3cc00672g.

Wang, Ce et al., "Lymphatic-targeted cationic liposomes: A robust vaccine adjuvant for promoting long-term immunological memory," Vaccine, 2014, vol. 32, 5475-5483.

Wang, Ce et al., Supplementary Data, 2014, Vaccine, 32, 5475-5483.

Wang, Qiong et al., "Antibody glycoengineering strategies in mammalian cells," Biotechnology and Bioengineering, 2018, vol. 115:1378-1393.

Wu, Chung-Yi et al., "Glycosite-deleted mRNA of SARS-CoV-2 spike protein as a broad-spectrum vaccine," PNAS, 2022, vol. 119, No. 9. https://doi.irg/10.1073/pnas.2119995119.

Zhang, Penghui et al., "Engineering the Surface of Smart Nanocarriers Using a pH-/Thermal-/GSH-Responsive Polymer Zipper for Precise Tumor Targeting Therapy in Vivo," Advanced Materials, 2017, vol. 29, 1702311 (10 pages).

Zhang, Ruhe et al., "Poly(disulfide)s: From Synthesis to Drug Delivery," Bio Macromolecules, 2022, vol. 23, pp. 1-19.

Zhang, Yong et al., "Site-specific N-glycosylation Characterization of Recombinant SARS-CoV-2 Spike Proteins," Mol Cell Proteomics, 2021, vol. 20, 100058. https://doi.org/10.1074/mcp.RA120.002295.

Du, Dan et al., "The role of glucose transporters in the distribution of p-aminophenyl-[alpha]-D-mannopyranoside modified liposomes within mice brain," Journal of Controlled Released, 2014, vol. 182. pp. 99-110.

He, P. et al., "Advances in aluminum hydroxide-based adjuvant research and its mechanism," Human Vaccine and Immunotherapeutics, 2015, vol. 11, iss. 2, pp. 477-488.

Ma et al., "The Role of Glucose Transporters in the Distribution of p-aminophenyl mannppyranose modified liposomes within mice brains," Journal of Controlled Release, 182, pp. 99-110. (Year: 2014).

\* cited by examiner

A.

B.

SIALIDASE-RESISTANT SACCHARIDE AND METHOD OF MAKING AND USING THE SAME

CROSS REFERENCE TO RELATED APPLICATIONS

This patent application is the National Stage of International Patent Application No. PCT/US2020/014608, filed on Mar. 10, 2020, which claims the benefit and priority of U.S. Provisional Patent Application No. 62/829,736, filed on Apr. 5, 2019, the disclosures of which are incorporated by reference herein in their entirety as part of the present application.

BACKGROUND

Sialic acid is a negatively charged monosaccharide often displayed at the outmost end of glycans on glycolipids and glycoproteins, which are involved in many physiological intra- and intercellular processes, including interactions with other biomolecules and receptors on cells, viruses, and bacteria.[1] In addition, sialylation plays an important role in regulating the function and fate of secreted glycoproteins and membrane-bound receptors. For example, sialylation of the epidermal growth factor receptor (EGFR) was shown to inhibit EGFR dimerization, thus interfering with EGF binding and phosphorylation, which is associated with tumorgenesis.[2] Also, sialylation modulates the half-life of glycoproteins in blood circulation as desialylation of N-glycans exposes the underlining galactose, which is recognized by the hepatic asialoglycoprotein receptors leading to a rapid removal of the glycoprotein from circulation.[3] Hence, increasing the degree of sialylation could improve the half-life and undesirable effects of glycoprotein therapeutics.

In recent years, the role of glycosylation on protein structure and function has been intensively studied inspiring the development of new methods for glycan synthesicampillary and glycoengineering of proteins, particularly therapeutic monoclonal antibodies (mAbs).[5] For instance, it has been shown that afucosylated biantennary N-glycan with terminal α-2,6-linked sialic acids has the optimal glycan structure for the enhancement of antibody-dependent cellular cytotoxicity (ADCC), complement-dependent cytotoxicity (CDC) and anti-inflammatory activities.[6]

Sialic acid derivatives with fluorine at the C-3 position are known to inhibit sialyltransferases and sialidases (or neuraminidases) and are more stable.[7] However, glycosylation with fluorinated sugars as donors often present a major challenge due to the strong electronic effect of the fluorine group that inactivates glycosylation reaction. Although there is a sialyltransferase capable of transferring a 3-fluoro-sialic acid residue from the corresponding cytidine monophosphate-sialic acid to form an α-2,3-linked sialoside, there is no corresponding α-2,6-sialyltransferase available.[11]

Thus, there is a need to provide a method for reliably preparing saccharides containing α-2,6-linked 3-fluoro-sialosides, which can be used for developing glycoprotein therapeutics.

SUMMARY

An aspect of the present invention is a method of preparing a saccharide that contains a 3-fluoro-sialic acid. The method includes conducting a glycosylation reaction by reacting a 3-hydroxy-sialic acid with a saccharide to form an α2,6-linked 3-hydroxy-sialoside and conducting a fluorination reaction by reacting the α2,6-linked 3-hydroxy-sialoside with a fluorinating agent to form a saccharide containing a 3-fluoro-sialic acid.

Another aspect of this invention is a method of preparing a homogeneous antibody bonded to a saccharide that contains a 3-fluoro-sialic acid. The method is carried out by glycosylating a monoclonal antibody with the saccharide.

An additional aspect of this invention relates to compounds of formula (VI):

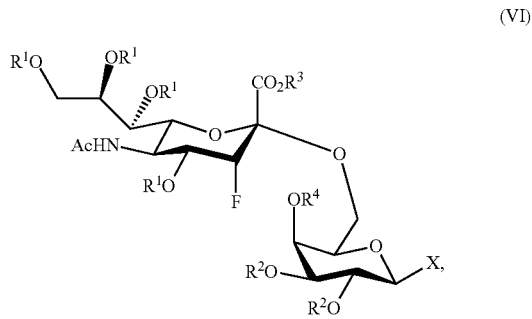

(VI)

in which $R^1$ is Ac or H, $R^2$ is Bz or H, $R^3$ is methyl or H, $R^4$ is Bn or H, and X is OH, a leaving group, or a saccharide. Note that "Ac" represents acetyl, "Bz" represents benzoyl, "Bn" represents benzyl, and the saccharide can be a monosaccharide, a disaccharide, or an oligosaccharide.

Also within the scope of the present invention is a monoclonal antibody bonded to an α2,6-linked 3-fluoro-sialoside terminated N-glycan.

Further covered by this invention is a method of treating a cancer. The method includes administering to a subject in need thereof an effective amount of a monoclonal antibody bonded to an α2,6-linked 3-fluoro-sialoside terminated N-glycan.

The details of the invention are set forth in the description below. Other features, objects, and advantages of the invention will be apparent from the following detailed description of several embodiments, and also from the appending claims.

BRIEF DESCRIPTION OF THE DRAWINGS

The description below refers to the accompanying drawings, of which.

DETAILED DESCRIPTION

Figure 1:
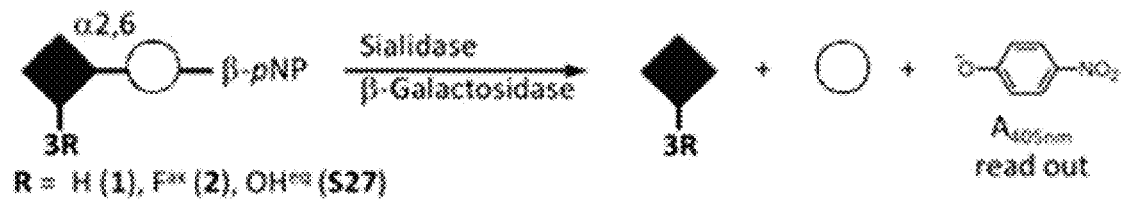
FIG. 1A shows two graphs depicting enzyme-catalyzed hydrolysis of three sialosides, i.e., 1, 2, and S27, as a function of enzyme concentration.
FIG. 1B shows two graphs depicting sialidase inhibition as a function of the concentration of 2, S27, or 2-deoxy-2,3-didehydro-N-acetylneuraminic acid (DANA), a sialidase inhibitor.
Figure 1:
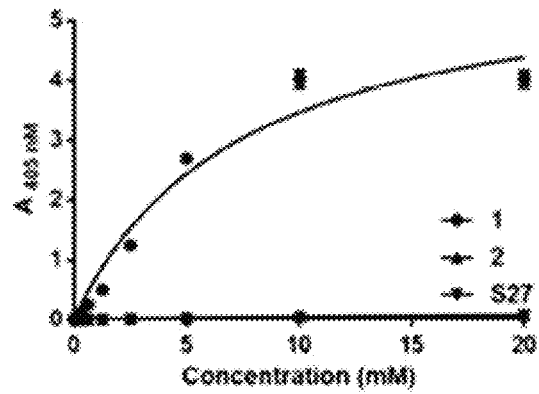
Figure 1:
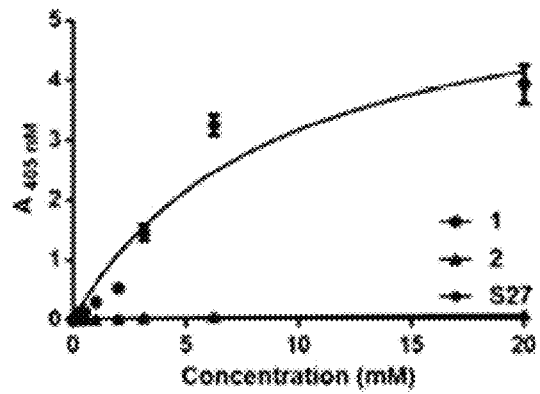
Figure 1:
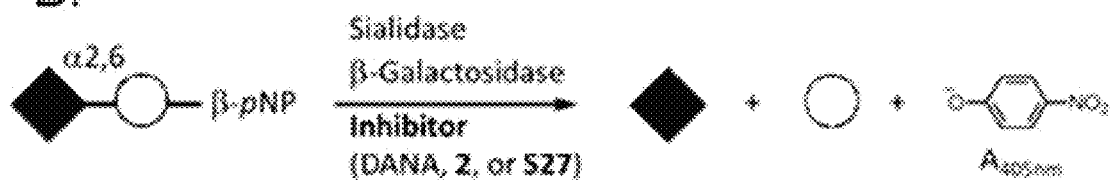
Figure 1:
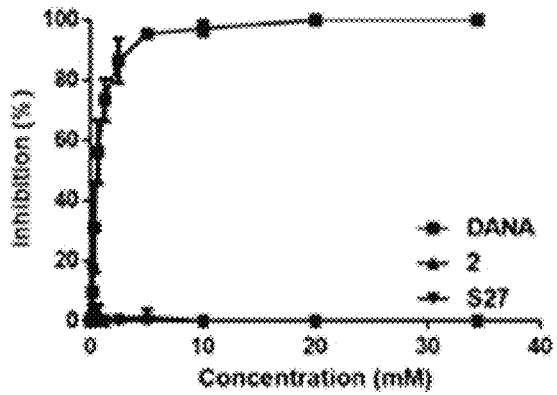
Figure 1:
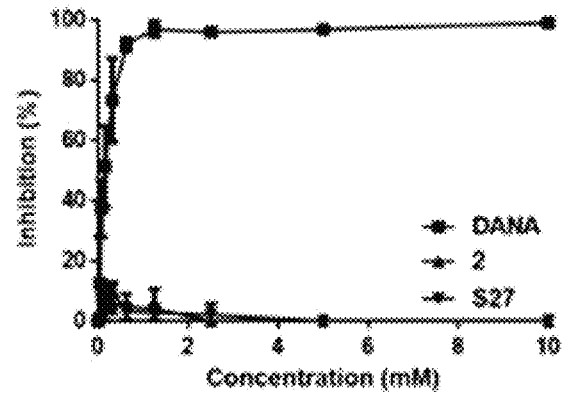

Disclosed first in detail herein is a method of preparing a saccharide that contains a 3-fluoro-sialic acid.

To reiterate, the method includes the steps of conducting a glycosylation reaction by reacting a 3-hydroxy-sialic acid with a saccharide to form an α2,6-linked 3-hydroxy-sialoside and conducting a fluorination reaction by reacting the α2,6-linked 3-hydroxy-sialoside with a fluorinating agent to form a saccharide containing a 3-fluoro-sialic acid. The saccharide can be a monosaccharide, a disaccharide, or an oligosaccharide. In an exemplary method, the saccharide is a monosaccharide.

In certain embodiments of this method, the 3-hydroxy-sialic acid is a 2-bromo-3-hydroxy-sialic acid, and the glycosylation reaction is conducted in the presence of silver trifluoromethanesulfonate (AgOTf) and disodium phosphate ($Na_2HPO_4$). Preferably, the glycosylation reaction is conducted in toluene.

In other embodiments of this method, the fluorinating agent is perfluoro-1-butanesulfonyl fluoride (NfF), and the fluorination reaction is conducted in the presence of a catalyst. For example, the catalyst is 1,8-diazabicyclo[5,4,0]-undec-7-ene (DBU). Preferably, the fluorination reaction is conducted in toluene. Of note, this reaction can be conducted further in the presence of tris(dimethylamino)sulfonium difluorotrimethylsilicate (TASF).

In an exemplary method, the 3-hydroxy-sialic acid is of formula (I):

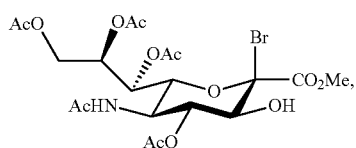

(I)

the saccharide is a compound of formula (II):

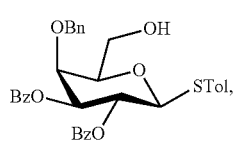

(II)

the α2,6-linked 3-hydroxy-sialoside is a compound of formula (III):

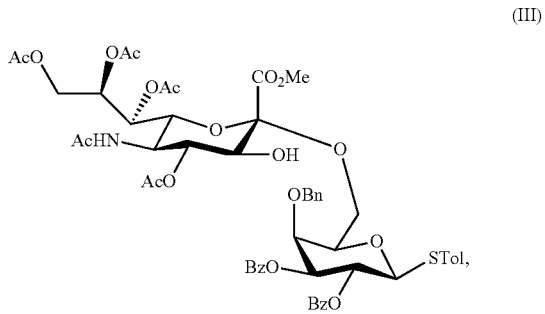

(III)

and
the saccharide containing a 3-fluoro-sialic acid is a compound of formula (IV):

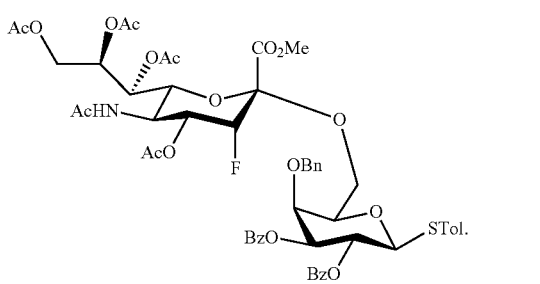

(IV)

In additional embodiments, the method further includes conducting another glycosylation reaction by reacting the saccharide containing a 3-fluoro-sialic acid with a second saccharide.

Also within the scope of this invention is a method of preparing a homogeneous antibody bonded to a saccharide containing a 3-fluoro-sialic acid. Again, this method includes glycosylating a monoclonal antibody with a saccharide containing a 3-fluoro-sialic acid.

In certain embodiments of this method, the saccharide containing a 3-fluoro-sialic acid is obtained by the method, and embodiments thereof, described above, which includes the steps of conducting a glycosylation reaction by reacting a 3-hydroxy-sialic acid with a saccharide to form an α2,6-linked 3-hydroxy-sialoside and conducting a fluorination reaction by reacting the α2,6-linked 3-hydroxy-sialoside with a fluorinating agent to form a saccharide containing a 3-fluoro-sialic acid.

In other embodiments, the saccharide containing a 3-fluoro-sialic acid is an α2,6-linked 3-fluoro-sialoside terminated N-glycan, which can be of formula (V):

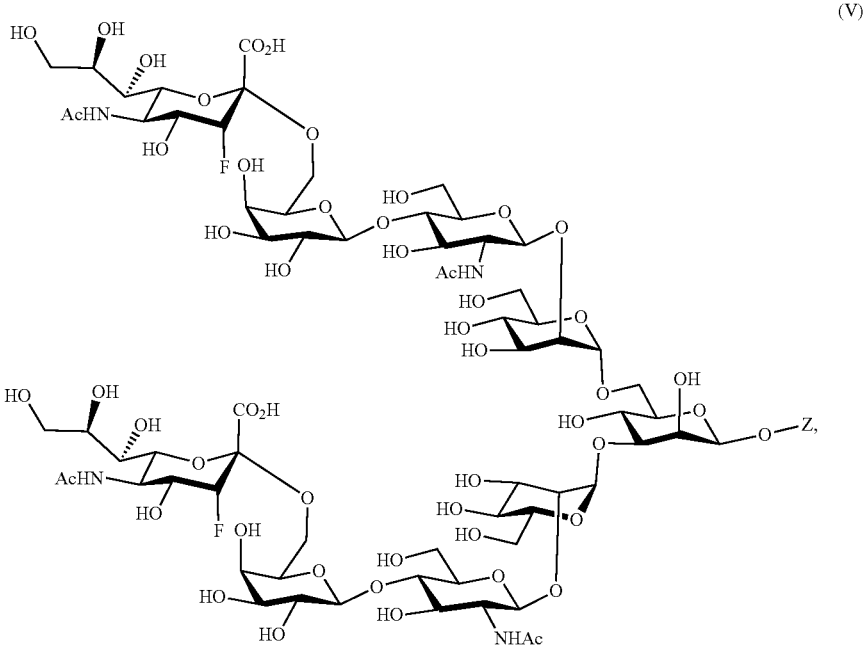
(V)
in which Z is
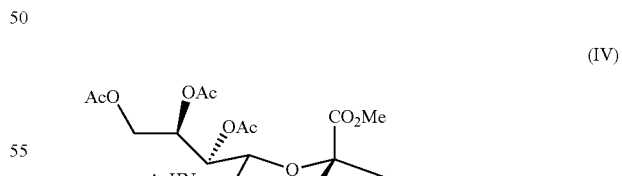
Another aspect of this invention relates to compounds of formula (VI):
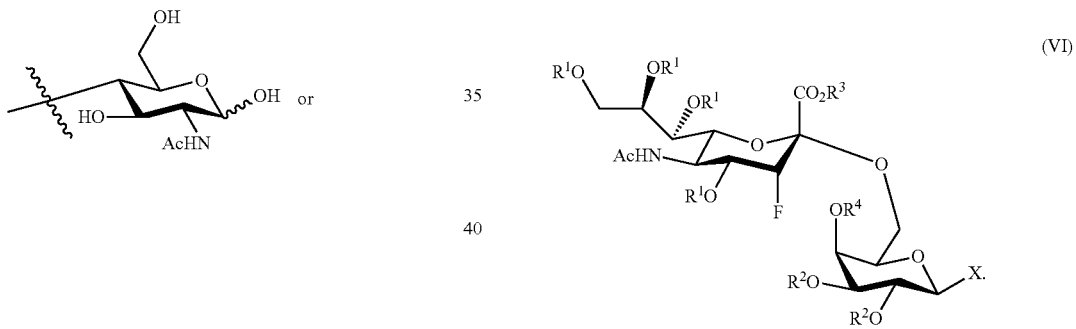
$R^1$, $R^2$, $R^3$, $R^4$, and X are defined in the SUMMARY section above.
In one embodiment, the compound is of formula (IV):
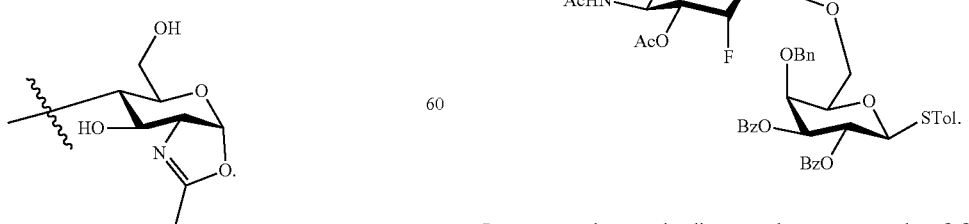
In yet another embodiment, the compounds of formula (VI) each includes X being an N-glycan. An exemplary compound of this embodiment is of formula (V):

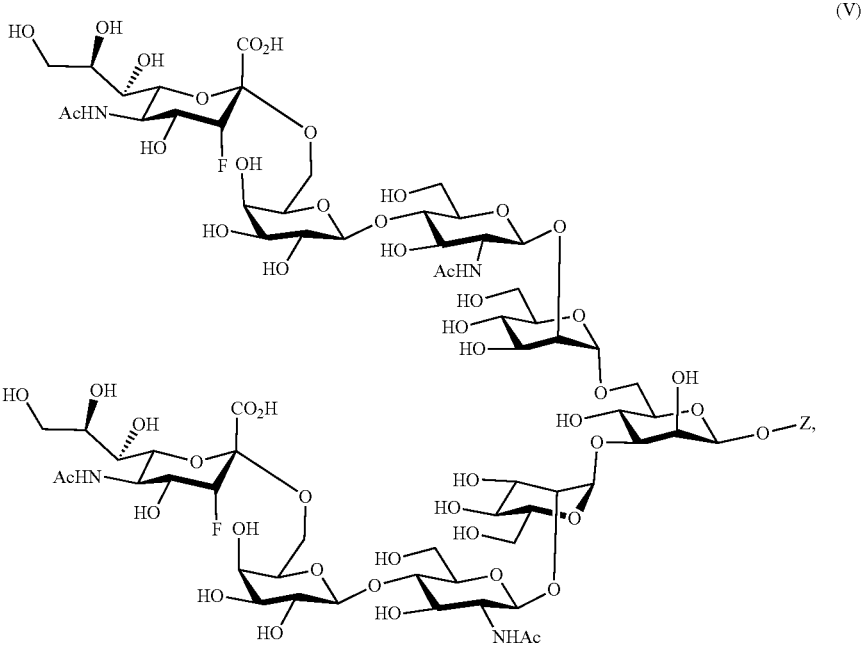

(V)

in which Z is

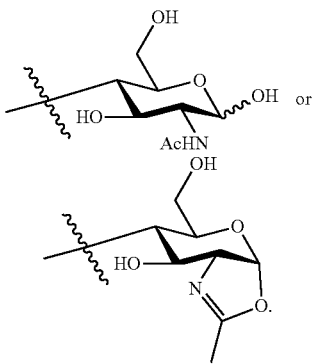

The present invention also covers a monoclonal antibody bonded to a saccharide containing a 3-fluoro-sialic acid, the saccharide containing a 3-fluoro-sialic acid being an α2,6-linked 3-fluoro-sialoside terminated N-glycan. Preferably, the α2,6-linked 3-fluoro-sialoside terminated N-glycan is of formula (V) shown above.

Further covered by this invention is a method of treating a cancer or an autoimmune disease, which includes administering to a subject in need thereof an effective amount of an above-described monoclonal antibody. For example, the cancer can be leukemia or lymphoma, and the autoimmune disease can be rheumatoid arthritis, autoimmune hemolytic anemia, pure red cell aplasia, thrombotic thrombocytopenic purpura, idiopathic thrombocytopenic purpura leukemia, lymphoma, Evans syndrome, vasculitis, bullous skin disorders, type 1 diabetes mellitus, Sjogren's syndrome, anti-NMDA receptor encephalitis, Devic's disease, Graves' ophthalmopathy, autoimmune pancreatitis, opsoclonus myoclonus syndrome, or a IgG4-related disease.

The term "treating" or "treatment" herein refers to administering a pharmaceutical composition described above to a subject, who has an above-described disease, i.e., cancer, a symptom of such a disease, or a predisposition toward such a disease, with the purpose of conferring a therapeutic or prophylactic effect. The term "an effective amount" refers to the amount of an active drug that is required to confer such effect. Effective doses will vary, as recognized by those skilled in the art, depending on the types of disease treated, route of administration, excipient usage, and the possibility of co-usage with other therapeutic treatment.

Provided below are more detailed descriptions of certain specific aspects of the present invention.

3-fluoro-substituted sialic acid derivatives, compared to non-fluorinated sialic acid derivatives, are known to be more stable towards sialidases.[7] By introducing the fluorine atoms to the anomeric and C-3 positions, a 2,3-difluorosialic acid (DFSA) was developed (Scheme 1)[8] and used as a biochemical probe,[9] and the activity-based protein profiling probe to study sialidases.[10] With the help of DFSA, it was shown that the fluorine atom at the axial position at C-3 ($3F^{ax}$) has a greater effect on slowing down both the deactivation ($k_i$) and reactivation ($k_{hydr}$) of the enzyme than the $3F^{eq}$ derivative.[8b] Inspired by this observation, we wanted to investigate the stability of sialosides with 3-fluorosialic acids for their potential use in glycoprotein therapeutics. Specifically, we intend to study if incorporation of a $3F^{ax}$-Neu5Ac motif at the terminal end of N-glycan on a mAb could increase its stability towards sialidases and sustain its effector functions.

Towards our goal, we developed a preparative method for the synthesis of α2,6-linked $3F^{ax}$-Neu5Ac oligosaccharides, including the biantennary N-glycan. We also showed that the synthetic $3-F^{ax}$Neu5Ac-α2,6-Gal linkage is more stable in the presence of sialidases and the antibody with the corresponding biantennary glycan has the same binding avidity as that of the non-fluorinated counterpart.

Several methods were reported for the synthesis of 3F-Neu5Ac, including (a) fluorination of protected glycans with $XeF_2$—$BF_3 \times OEt_2$,[12] molecular fluorine[13] and Selectfluor;[7c] (b) inversion of equatorial hydroxyl group at C3 in a sialic acid derivative;[7f] and (c) aldolase-catalyzed enzymatic transformation of ManNAc and 3-fluoro-pyruvate into $3F^{eq}$Neu5Ac and 3FaxNeu5Ac.[7a, 11a, 14] However, to the best of our knowledge, there is no method describing the synthesis of N-glycans terminated with $3F^{ax}$-Neu5Ac so far.

The only account disclosing the preparation of disaccharides with $3F^{ax}$-Neu5Ac was limited to the enzymatic synthesis of 3-FaxNeu5Ac-α2,3-Lac, and not the required α2,6-linkage.[11a] We, therefore, focused our effort on the chemical synthesis of this linkage.[15]

Scheme 1

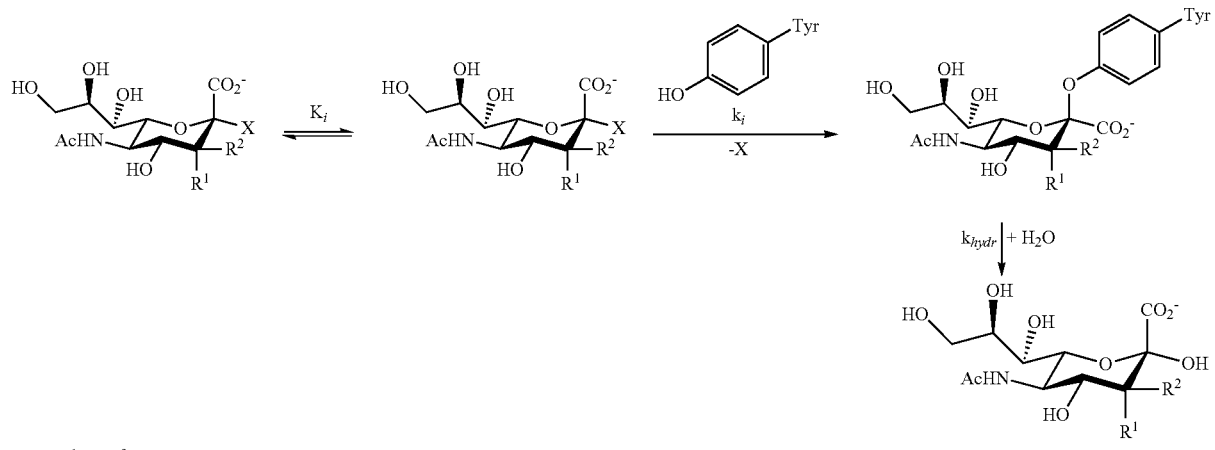

DFSA: $R^1 = F$, $R^2 = H$, $X = F$ ($k_i \gg k_{hydr}$)
Neu5Ac-α2,6-Gal-βpNP (1): $R^1 = H$, $R^2 = H$, $X = $ α2,6-Gal-βpNP
$3F^{ax}$Neu5Ac-α2,6-Gal-βpNP (2): $R^1 = F$, $R^2 = H$, $X = $ α2,6-Gal-βpNP After screening a variety of glycosylation conditions using $3F^{ax}$-Neu5Ac-based donors (Scheme 2a), we investigated the alternative strategies, which encompassed the $S_N2$ reaction of the $3OH^{eq}$ to $3F^{ax}$ in 3OH-Neu5Ac-α2,6-Gal-STol (Scheme 2b). First, we studied the sialylation at O-6 using conditions reported by Goto et al. (Table 1, entry 1).[16] The reaction was carried out using 1 equiv. of AgOTf as a promoter and $Na_2HPO_4$ as a base in toluene at −10° C. (Scheme 3). These conditions provided disaccharide 6 in low yield (15%) with a 3:1 (α:β) anomeric ratio. Changing the solvent to $CH_2Cl_2$ did not improve the diastereoselectivity (entry 2). By increasing the temperature and reaction time, the yield was improved, however, the selectivity decreased dramatically (entries 3-5). Surprisingly, the more equivalents of acceptor were used, the better stereoselectivity was observed (entry 3 vs. 6). The optimized conditions (entry 7) provided 6 in 35% (99% brsm) yield with excellent α-selectivity (α:β=13:1).

Scheme 2

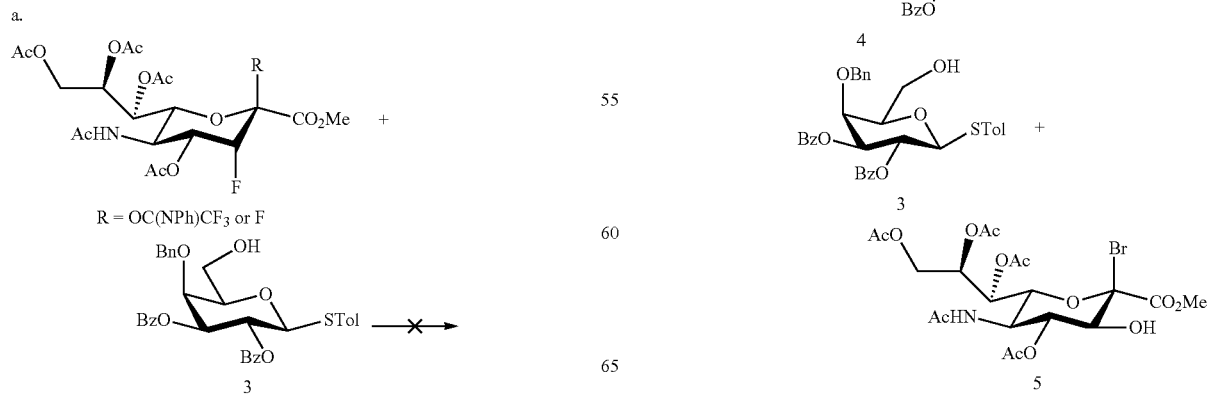

-continued
Scheme 3

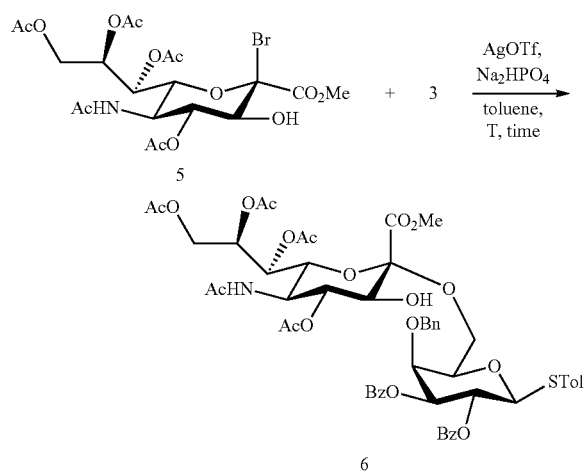

TABLE 1

Optimization of the glycosylation step.

| entry | 5/3/AgOTf/ Na$_2$HPO$_4$, (equiv.) | T (°C.) | time (h) | α:β$^a$ | Yield$^b$ (%) (brsm)$^c$ |
|---|---|---|---|---|---|
| 1 | 1/1.1/1/4.6 | −10 | 0.5 | 3.1:1 | 15$^d$ |
| 2$^e$ | 1.1/1/1.1/— | −78 to −20 | 3 | 2.7:1 | 21$^d$ |
| 3 | 0.8/1/1.6/4.5 | −50 | 16 | 5.2:1 | 46 (94) |
| 4 | 0.7/1/1.5/4.2 | −50 to −35 | 16 | 3.8:1 | 53 (99) |
| 5 | 0.7/1/1.5/4.2 | −50 to −15 | 16 | 1.8:1 | 72 (99) |
| 6 | 1/1.25/1.5/4.2 | −50 | 16 | 16:1 | 28 |
| 7 | 1/1.5/4.2 | −50 | 16 | 13:1 | 35 (99) |
| 8$^f$ | 1/1.1/1.5/— | −50 | 16 | 11:1 | 33 (99) |
| 9$^g$ | 1/1.1/1.5/4.2 | −50 | 24 | 13:1 | 35 (99) |

$^a$Determined by $^1$H NMR.
$^b$Yield of isolated product.
$^c$Yield based on the recovered starting material (brsm), acceptor.
$^d$The donor and acceptor were not completely consumed.
$^e$Using CH$_2$Cl$_2$ with 4Å MS.
$^f$With 4Å MS.
$^g$Gram-scale.

Inversion of OH$^{eq}$ to F$^{ax}$ turned out to be a challenging task. Substitution of OTf and OMs by fluorine using TASF led to decomposition of the starting material. To optimize this transformation, we screened a variety of fluorinating reagents without any success. However, treatment of 6 with perfluoro-1-butanesulfonyl fluoride (NfF) in the presence of 1,8-diazabicyclo[5,4,0]-undec-7-ene (DBU) in anhydrous toluene (Scheme 3) for 2 days at 90° C. gave 4 in 6% yield (Table 2, entry 1).[17] Further optimization of the reaction conditions, such as decreasing reaction temperature (entries 1, 5 and 6) and increasing reaction times (entry 7), improved the overall yield of 4. It seems that the transformation of 7 to 4 is a rate-limiting step due to the steric hindrance around C-3. In many cases, we were able to isolate 7 formed in the presence of NfF and DBU at room temperature within 1 day. However, conversion of 7 to 4 (77% brsm yield) requires long reaction times. The attempts to improve the conversion by elevating reaction temperature resulted in decomposition of 7. Thus, our best result was obtained by increasing amounts of reagents and reaction times to 15 days (entry 8). Finally, we found that addition of TASF helped improve the reaction efficiency reducing the reaction time to only 2 days (entry 9). The stereochemistry of fully protected 3F$^{ax}$-Neu5Ac-α2,6-Gal-STol disaccharide (4) was verified by the X-ray diffraction analysis.

Scheme 4

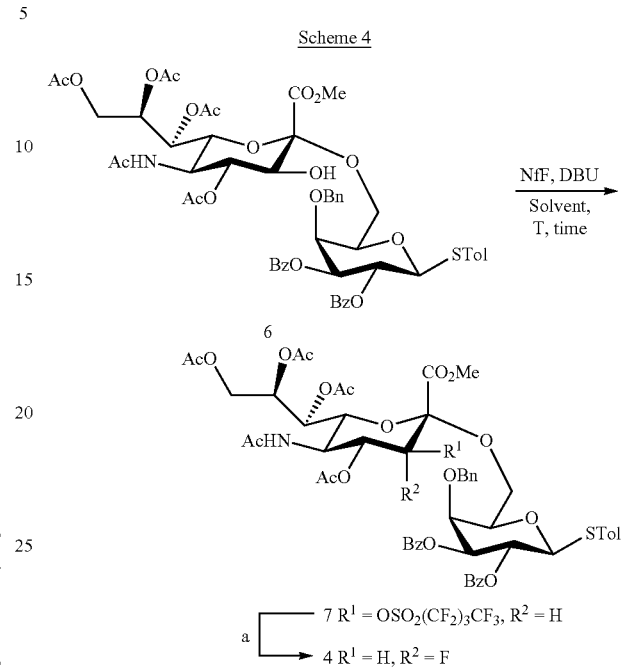

TABLE 2

Optimization of the fluorination step.

| entry | NfF/DBU, (equiv.) | solvent | T (°C.) | time (day) | Yield,$^b$ (%) 4:7 |
|---|---|---|---|---|---|
| 1 | 6/6 | THF | 25 to 90 | 2 | 4 |
| 2 | 6/6 | CH$_3$CN | 25 to 90 | 2 | 2 |
| 3 | 6/6 | toluene | 25 to 90 | 2 | 6 |
| 4 | 4/4 | DMF | 40 | 9 | —$^c$ |
| 5 | 4/4 | toluene | 50 | 6 | 8:71 |
| 6 | 4/4 | toluene | 40 | 7 | 30:52 |
| 7 | 4/4 | toluene | 40 | 17 | 36:44 |
| 8$^d$ | 8/8 | toluene | 40 | 15 | 63:15 |
| 9$^e$ | 8/8 | toluene | 40 | 2 | 60:8 |

$^a$Reagents and conditions: (a) NfF, DBU, toluene, 40° C., 15 d, 49% (77% brsm).
$^b$Yield of isolated product.
$^c$No product observed.
$^d$Portion-wise addition of NfF (4 equiv./day) and DBU (4 equiv./day) followed by stirring for 14 days.
$^e$Portion-wise addition of NfF (4 equiv./day), DBU (4 equiv./day) and tris(dimethylamino) sulfonium difluorotrimethylsilicate (TASF) (2 equiv./day).

Referring to Scheme 5, the 3F$^{ax}$-Neu5Ac-disaccharide donor 4 was coupled with the acceptor (8) using NIS/TMSOTf to give 9. Next, the O-allyl group at the anomeric position was removed by isomerization with PdCl$_2$ in AcOH/NaOAc, and the anomeric hydroxyl group (10) was further transformed into fluoride (11) and imidate (12). The glycosylation of the core disaccharide (13) at O-3 with 3F$^{ax}$-Neu5Ac-terminated fluoride donor (11) using Cp$_2$HfCl$_2$/AgOTf conditions gave hexasaccharide 14 in 85% yield. After removal of the benzylidene group, 15 was glycosylated at the O-6 position to give the desired decasaccharide (16) in 70% yield with excellent regio- and α-stereoselectivity. We also tested the TfOH-promoted glycosylation with N-phenyl trifluoroacetimidate donor (12), which, however, gave the product in a poor yield. Next, the fully deprotected glycan (17) was obtained in 40% overall yield following a sequence of steps: (a) saponification with LiOH to remove the esters and the NHTroc group; (b) acetylation of free amines and alcohols; (c) removal of the OAc groups with sodium methoxide; and (d) hydrogenolysis of the O-benzyl groups with Pd/C in a mixture of MeOH/water/ $HCO_2H$.[4b]

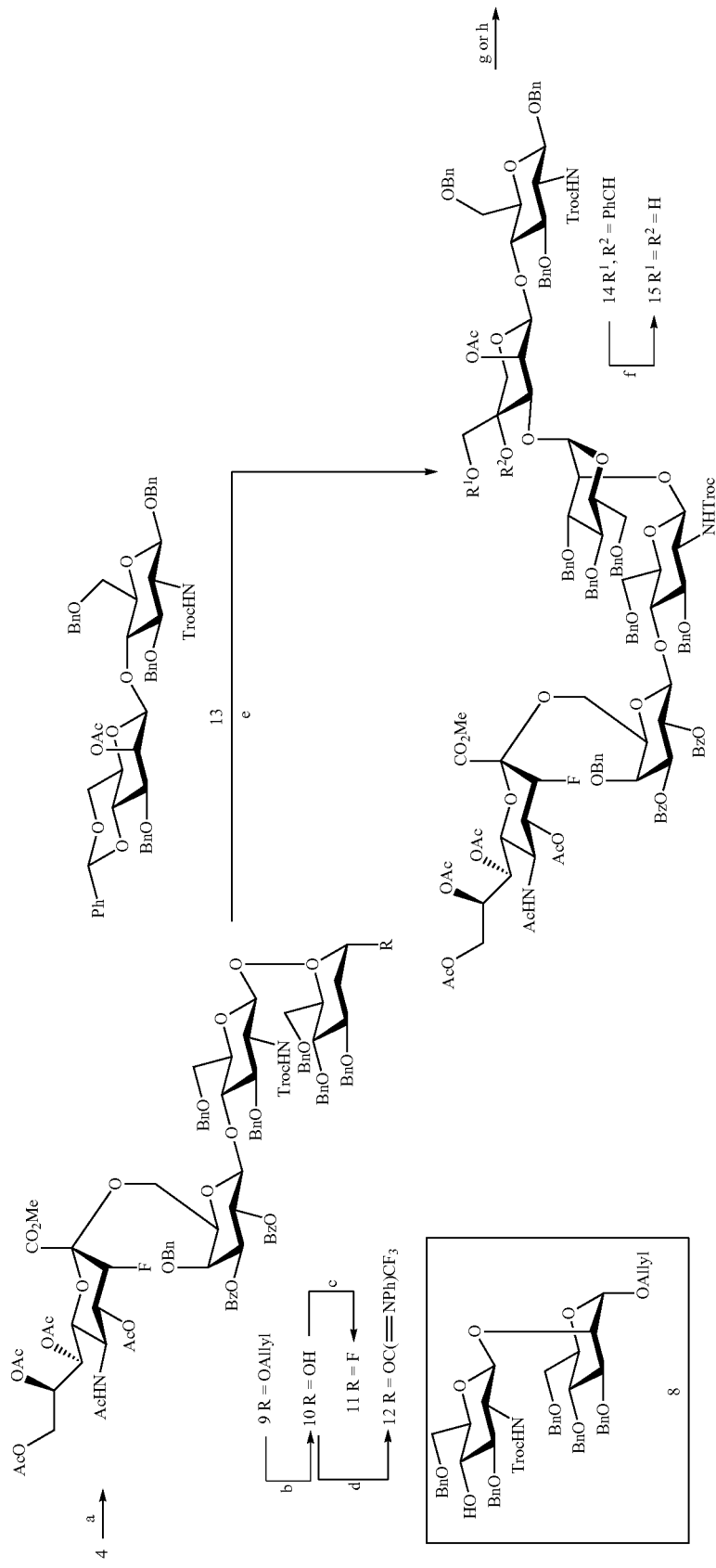

-continued

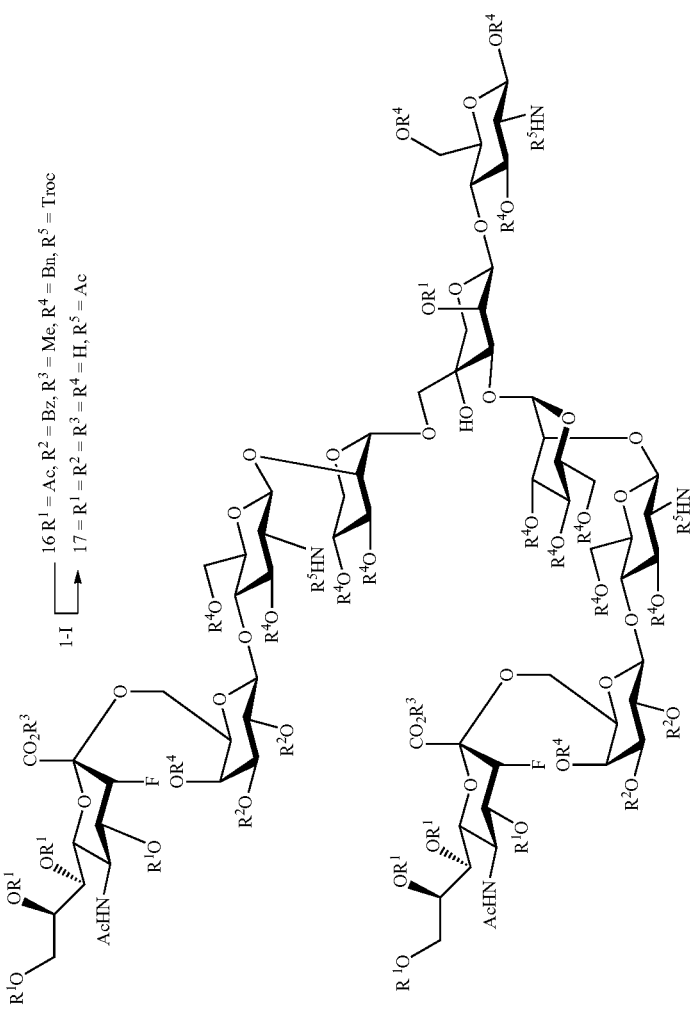

16 R¹ = Ac, R² = Bz, R³ = Me, R⁴ = Bn, R⁵ = Troc
17 R¹ = R² = R³ = R⁴ = H, R⁵ = Ac Reagents and conditions in Scheme 5:
(a) 8, TfOH, NIS, 4 Å MS, CH₂Cl₂, -40° C., 2 h, 64%.
(b) PdCl₂, CH₃COONa, AcOH/H₂O, 82%.
(c) DAST, CH₂Cl₂, -20° C., 73%.
(d) ClC(=NPh)CF₃, Cs₂CO₃, CH₂Cl₂ 0° C. to r.t, 3 h, 56%;
(e) 11, AgOTf, Cp₂HfCl₂, toluene, 4 Å MS, 0° C., 3 h, 85%;
(f) pTSA·H₂O, CH₃CN, r.t., 6 h, 75%;
(g) 11, AgOTf, Cp₂HfCl₂, toluene, 4 Å MS, -15° C., 3 h, 70% (80% brsm);
(h) 12, TfOH, CH₂Cl₂, 4 Å MS, -60 to -20° C., 3 h, 33% (55% brsm);
(i) LiOH, dioxane/H₂O (4:1), 90° C., 16 hrs;
(j) Ac₂O, Py, 16 h;
(k) NaOMe, MeOH, 16 h;
(l) Pd(OH)₂, MeOH/H₂O/HCOOH (6:3:1), H₂, 16 h, 40% (4 steps).

Reagents and conditions in Scheme 5: (a) 8, TfOH, NIS, 4 Å MS, CH$_2$Cl$_2$, 40° C., 2 h, 64%. (b) PdCl$_2$, CH$_3$COONa, AcOH/H$_2$O, 82%. (c) DAST, CH$_2$Cl$_2$, −20° C., 73%. (d) ClC(=NPh)CF$_3$, Cs$_2$CO$_3$, CH$_2$Cl$_2$, 0° C. to r.t., 3 h, 56%; (e) 11, AgOTf, Cp$_2$HfCl$_2$, toluene, 4 Å MS, 0° C., 3 h, 85%; (f) pTSA·H$_2$O, CH$_3$CN, r.t., 6 h, 75%; (g) 11, AgOTf, Cp$_2$HfCl$_2$, toluene, 4 Å MS, −15° C., 3 h, 70% (80% brsm); (h) 12, TfOH, CH$_2$Cl$_2$, 4 Å MS, −60 to −20° C., 3 h, 33% (55% brsm); (i) LiOH, dioxane/H$_2$O (4:1), 90° C., 16 hrs; (j) Ac$_2$O, Py, 16 h; (k) NaOMe, MeOH, 16 h; (l) Pd(OH)$_2$, MeOH/H$_2$O/HCOOH (6:3:1), H$_2$, 16 h, 40% (4 steps).

Having established a protocol for the stepwise synthesis, we streamlined the glycan assembly by developing a programmable [2+2+2] one-pot synthesis of hexasaccharide (14), which is a precursor of 17 (Scheme 6). The designed one-pot protocol was comprised of the initial coupling of the 3F$^{ax}$-Neu5Ac-disaccharide donor (4) (RRV=2053) with a less reactive acceptor (18) (RRV=537) at −40° C., followed by injection of the reducing-end acceptor 13 at −20° C. After 1 h at −10° C. and a standard purification protocol, the hexasaccharide 14 was isolated in 26% yield.

Scheme 6

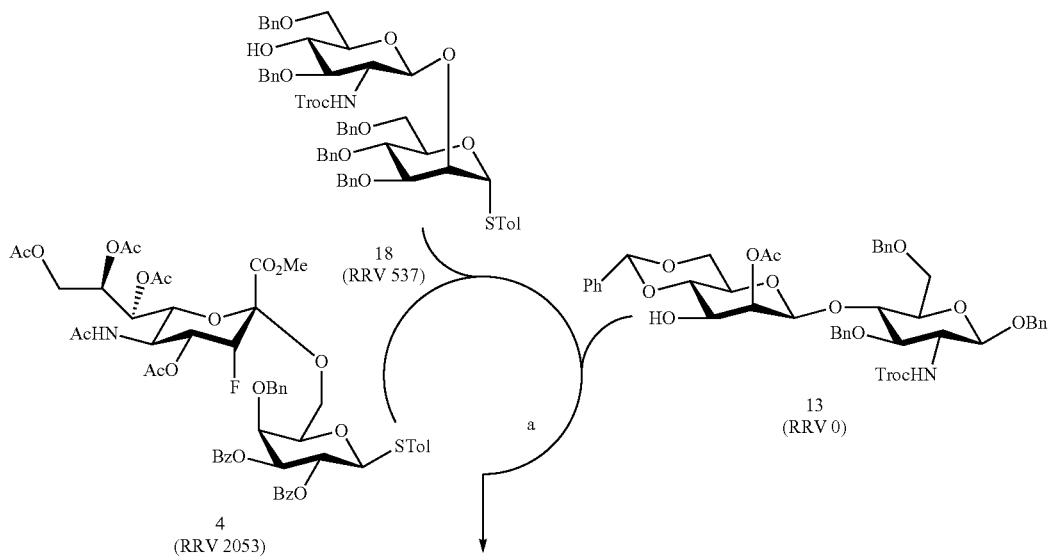

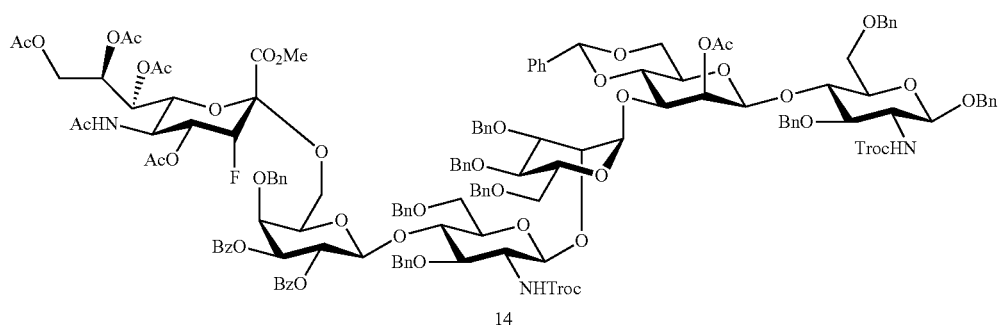

Reagents and conditions in Scheme 6: (a) TfOH, NIS, 4Å MS, CH$_2$Cl$_2$, -40° C. to -10° C., 3 h, 26%

In order to gather preliminary data about the stability of the 3F$^{ax}$-Neu5Ac-α2,6-Gal motif in the presence of sialidases, we prepared Neu5Ac-α2,6-Gal-pNP (1) and the 3F$^{ax}$-Neu5Ac analog (2) as substrates (Scheme 1) for the in vitro assay[19] with the commercially available sialidases from *C. perfingens* and *V. cholera*. Both enzymes showed the expected hydrolytic activity for the native substrate 1 but were inactive toward the 3F$^{ax}$-analog 2 (see FIG. 1A). We also observed that 2 did not significantly inhibit the hydrolysis of 1 as DANA did (see FIG. 1B).

To prepare a homogeneous glycoform of mAb, compound 17 was converted into the oxazoline donor and ligated to the GlcNAc-primed IgG (without core fucose) in the presence of Endo S2 (D184Q) following a standard protocol.[6] The binding avidity of the homogeneous 3F$^{ax}$-Neu5Ac-glycoform to FcγRIIIa was measured by surface plasma resonance analysis[6] together with the parent nonfluorinated glycoform (G2S2) and a commercial sample of rituximab (major glycoforms: G1F1, G0F1, G2F1). When compared to the commercial sample of rituximab, the homogeneous glycoforms of IgG bearing biantennary N-glycans with α2,6-sialylation and without core fucose demonstrated 39.9-fold (Neu5Ac-G2S2) and 37.4-fold (3F$^{ax}$-Neu5Ac-G2S2) improvement in binding avidity (see Table 4). The fact that the avidity of the 3F$^{ax}$-Neu5Ac-modified glycoform was found to be within the same range as that of the parent glycan provides a premise for the in vivo studies of 3F$^{ax}$-Neu5Ac-glycosylated mAb. These results will be reported in a due course.

In conclusion, we have developed a chemical synthesis of 3F$^{ax}$-Neu5Ac-α2,6-Gal-STol as building block for the synthesis of sialidase-resistant oligosaccharides and a representative homogeneous antibody with 3F$^{ax}$-Neu5Ac-terminated bi-antennary N-glycan. When compared with the commercial rituximab sample, the homogeneous glycoform modified with 3F$^{ax}$-Neu5Ac-glycans showed a 37.4-fold improvement in binding to the FcγRIIIa. Moreover, the parent nonfluorinated and 3F$^{ax}$-Neu5Ac-modified antibody glycoforms demonstrated similar binding avidity to an Fc receptor. Overall, our results have revealed a new general strategy for the improvement of half-lives of therapeutic glycoproteins.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. All publications cited herein are incorporated by reference in their entirety.

Example 1: Synthesis of Saccharides Containing a 3-fluoro-sialic acid and Precursors All reactions were carried out under an inert atmosphere unless mentioned otherwise, and standard syringe-septa techniques were followed. Solvents were purchased from commercial sources and used without further purification. Pulverized molecular sieves 4 Å (EMD Millipore) were grounded in powder and activated before use. The progress of all the reactions was monitored by TLC glass plates precoated with silica gel 60 F254 (Merck KGaA). The TLC was visualized by UV light (254 nm), p-anisaldehyde and/or ceric ammonium molybdate stains. Column chromatography was performed on Across silica gel (particle size 0.035-0.070 mm, 60 Å). $^1$H, $^{13}$C, and $^{19}$F NMR spectra were recorded with Bruker AVIII-600, DRX-500, AV-400, DPX-400, AVANCE 500 AV and AVANCE 600 spectrometers at 25° C. and chemical shifts were measured in δ (ppm) with residual solvent peaks as internal standards (δ, ppm: 7.24 (CHCl$_3$), 4.80 (H$_2$O) in $^1$H NMR; and 77 (CDCl$_3$) in $^{13}$C NMR). Coupling constants (J) were measured in Hz. Data are represented as follows: chemical shift, multiplicity (s=singlet, d=doublet, t=triplet, q=quartet, m=multiplet, br=broad). High-resolution mass spectra (HRMS) were recorded on an Agilent LC/MSD TOF mass spectrometer by electrospray ionization time-of-flight (ESI-TOF) reflectron experiments. The single crystal X-ray diffraction studies were carried out on a Bruker D8 Platinum-$^{135}$ CCD diffractometer equipped with Cu K$_α$ radiation (□=1.5478). HPLC measurements were performed on a Hitachi HPLC D-7000 system. RRV measurements were recorded using a normal-phase ZORBAX RX-SIL, 5 μm, 4.6×250 mm (Colloidal Silica, Agilent Technologies) using the solvent system EtOAc/hexane with 1 mL/min flow rate, and visualized at 254 nm.

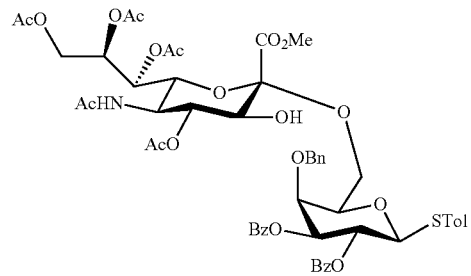

p-Tolyl [methyl 5-acetamido-4,7,8,9-tetra-O-acetyl-5-deoxy-D-erythro-α-L-gluco-non-2-ulopyranosonate]-(2→6)-2,3-di-O-benzoyl-4-O-benzyl-1-thio-β-D-galactopyranoside 6α. A mixture of acceptor 3 (1.05 g, 1.80 mmol, 1 equiv.) and donor 5 (1.02 mg, 1.80 mmol, 1 equiv.) in anhydrous toluene (60 mL) was stirred under argon atmosphere for 10 min. Then, the reaction mixture was cooled to −50° C. and dry Na$_2$HPO$_4$ (1.07 g, 7.54 mmol, 4.2 equiv.) was added, followed by AgOTf (692 mg, 2.69 mmol, 1.5 equiv., in toluene 18 mL) with stirring. Upon completion of the reaction (TLC indicated the disappearance of starting materials after 24 hrs), the reaction mixture was diluted with EtOAc (80 mL), washed with 20% aq. Na$_2$S$_2$O$_3$ (10 mL), satd. aq. NaHCO$_3$ (5 mL) and brine (5 mL), then the organic layer was dried over MgSO$_4$, filtered, and concentrated. The obtained residue was purified by silica gel column chromatography using acetone/toluene (3:7) as eluent to give compound 6 (α:β=13:1) as a white powder (680 mg, 35%) along with recovered acceptor 3 (670 mg, 99% brsm). α-anomer 6α: R$_f$=0.36 (silica gel, CHCl$_3$:MeOH=20:1); $^1$H NMR (600 MHz, CDCl$_3$): δ 7.96-7.94 (m, 2H, Ar—H), 7.91-7.90 (m, 2H, Ar—H), 7.50-7.47 (m, 2H, Ar—H), 7.40-7.39 (m, 2H, Ar—H), 7.37-7.32 (m, 5H, Ar—H), 7.25-7.18 (m, 4H, Ar—H), 7.06-7.04 (m, 2H, Ar—H), 5.81 (dd, J=10.2, 9.6 Hz, 1H), 5.59 (d, J=10.2 Hz, 1H), 5.38 (dd, J=9.0, 3.0 Hz, 1H), 5.35-5.32 (m, 1H), 5.25 (dd, J=10.2, 9.6 Hz, 1H), 5.24 (d, J=7.8, 2.4 Hz, 1H), 4.92 (d, J=9.6 Hz, 1H, C1-H$_β$), 4.71 (d, J=12.0 Hz, 1H), 4.60 (d, J=12.0 Hz, 1H), 4.49 (dd, J=10.8, 1.8 Hz, 1H), 4.30 (dd, J=12.6, 3.0 Hz, 1H), 4.26 (ddd, J=10.2, 10.2, 10.2 Hz, 1H), 4.20 (d, J=3.0 Hz, 1H), 4.10 (dd, J=10.2, 7.2 Hz, 1H), 4.04 (dd, J=12.6, 6.6 Hz, 1H), 4.00 (dd, J=6.6, 6.6 Hz, 1H), 3.86 (d, J=9.6 Hz, 1H), 3.82-3.73 (m, 2H), 3.75 (s, 3H, —CH$_3$), 2.30 (s, 3H, —CH$_3$), 2.09 (s, 3H, —CH$_3$), 2.07 (s, 3H, —CH$_3$), 2.06 (s, 3H, —CH$_3$), 1.96 (s, 3H, —CH$_3$), 1.89 (s, 3H, —CH$_3$); $^{13}$C NMR (150 MHz, CDCl₃): δ 171.6, 170.6, 170.3, 170.1, 169.5, 168.5, 165.8, 165.1, 138.0, 137.9, 133.4, 133.1, 129.8, 129.7, 129.6, 128.9, 128.6, 128.4, 128.3, 128.2, 127.7, 127.6, 100.3, 86.6, 75.9, 74.5, 73.7, 73.2, 73.1, 72.5, 68.8, 68.3, 63.1, 62.5, 52.8, 48.4, 23.1, 21.2, 20.9, 20.8, 20.7, 20.7; HRMS (ESI-TOF) m/e: Calcd for $C_{54}H_{59}NO_{20}SNa$ [M+Na]⁺: 1096.3243 found 1096.3241.

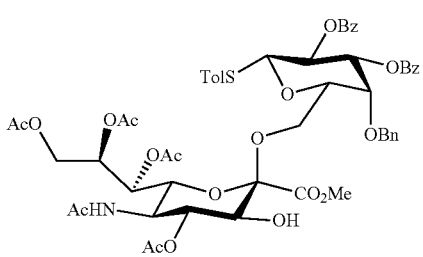

p-Tolyl [methyl 5-acetamido-4,7,8,9-tetra-O-acetyl-5-deoxy-D-erythro-β-L-gluco-non-2-ulopyranosonate]-(2→6)-2,3-di-O-benzoyl-4-O-benzyl-1-thio-β-D-galactopyranoside 6β. β-anomer 6β $R_f$=0.42 (silica gel, CHCl₃:MeOH=20:1); ¹H NMR (600 MHz, CDCl₃): δ 7.94-7.92 (m, 4H, Ar—H), 7.50-7.47 (m, 2H, Ar—H), 7.43-7.40 (m, 6H, Ar—H), 7.37-7.31 (m, 5H, Ar—H), 7.13-7.12 (m, 2H, Ar—H), 5.81 (dd, J=10.2, 10.2 Hz, 1H), 5.51 (dd, J=10.2, 3.0 Hz, 1H), 5.22 (ddd, J=6.0, 6.0, 3.0 Hz, 1H), 5.14 (d, J=13.2 Hz, 1H), 5.07 (dd, J=6.0, 2.4 Hz, 1H), 4.90 (d, J=10.2 Hz, 1H, C1-H_β), 4.66-4.62 (m, 2H), 4.55 (dd, J=12.6, 2.4 Hz, 1H), 4.29 (d, J=1.8 Hz, 1H), 4.14 (dd, J=7.8, 7.2 Hz, 1H), 4.08 (ddd, J=10.8, 10.8, 10.8 Hz, 1H), 3.98 (dd, J=12.6, 6.6 Hz, 1H), 3.92-3.88 (m, 2H), 3.85-3.77 (m, 3H), 3.83 (s, 3H, —CH₃), 3.53 (dd, J=10.8, 2.4 Hz, 1H), 2.32 (s, 3H, —CH₃), 2.26 (s, 3H, —CH₃), 2.07 (s, 3H, —CH₃), 2.04 (s, 3H, —CH₃), 1.97 (s, 3H, —CH₃), 1.68 (s, 3H, —CH₃); ¹³C NMR (150 MHz, CDCl₃): δ 171.4, 170.6, 170.3, 169.8, 169.8, 166.6, 165.8, 165.2, 139.2, 138.4, 133.5, 133.4, 133.1, 129.9, 129.8, 129.5, 128.9, 128.5, 128.3, 127.2, 126.0, 99.6, 86.9, 76.0, 75.5, 74.3, 73.1, 72.5, 71.7, 70.3, 68.4, 67.2, 62.1, 62.0, 53.3, 47.5, 22.9, 21.5, 21.2, 20.8, 20.7, 20.7; HRMS (ESI-TOF) m/e: Calcd for $C_{54}H_{59}NO_{20}S$ [M+H]⁺: 1074.3424 found 1074.3458.

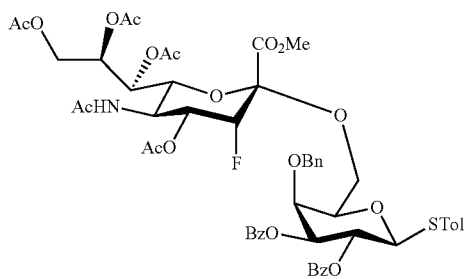

p-Tolyl [methyl 5-acetamido-4,7,8,9-tetra-O-acetyl-3,5-dideoxy-3-fluoro-D-erythro-α-L-manno-non-2-ulopyranosonate]-(2→6)-2,3-di-O-benzoyl-4-O-benzyl-1-thio-β-D-galactopyranoside 4. To a solution of compound 6a (500 mg, 0.47 mmol, 1 equiv.) in toluene (5 mL) in a screw-capped vial containing a stirring bar was added DBU (0.28 mL, 1.86 mmol, 4 equiv.), perfluoro-1-butanesulfonyl fluoride (0.33 mL, 1.86 mmol, 4 equiv.) and TASF (256 mg, 0.93 mmol, 2 equiv.). The reaction vial was sealed and stirred at 40° C. After 24 h, the reaction mixture was treated with additional amounts of DBU (0.28 mL, 1.86 mmol, 4 equiv.), perfluoro-1-butanesulfonyl fluoride (0.33 mL, 1.86 mmol, 4 equiv.) and TASF (256 mg, 0.93 mmol, 2 equiv.), then stirred at 40° C. for another 24 h. The reaction mixture was directly loaded onto the silica gel column and eluted with acetone/toluene (7:3). The disaccharide 4 was obtained as a light yellow powder (300 mg, 60%) along with perfluoro-1-butanesulfonyl compound 7 as a light yellow powder (50 mg, 8%).

Synthesis of the disaccharide 4 from 7: To a solution of compound 7 (730 mg, 0.54 mmol, 1 equiv.) in toluene (7 mL) in a screw-capped vial containing a stirring bar was added DBU (0.64 mL, 4.31 mmol, 8 equiv.) and perfluoro-1-butanesulfonyl fluoride (0.77 mL, 4.31 mmol, 8 equiv.). The container was sealed and stirred at 40° C. for 15 days. The reaction mixture was directly loaded onto the silica gel column and eluted with acetone/toluene (7:3) as eluent; disaccharide 4 was isolated as a light yellow powder (282 mg, 49%) along with perfluoro-1-butanesulfonyl compound 7 as a light yellow powder (267 mg, 77% brsm). $R_f$=0.43 (silica gel, acetone/toluene=2:3); ¹H NMR (600 MHz, CDCl₃): δ 7.95-7.93 (m, 2H, Ar—H), 7.87-7.85 (m, 2H, Ar—H), 7.48-7.44 (m, 2H, Ar—H), 7.41-7.39 (m, 2H, Ar—H), 7.35-7.33 (m, 2H, Ar—H), 7.31-7.29 (m, 2H, Ar—H), 7.25-7.24 (m, 2H, Ar—H), 7.21-7.19 (m, 2H, Ar—H), 7.16-7.14 (m, 1H, Ar—H), 7.04-7.03 (m, 2H, Ar—H), 5.79 (dd, J=10.2, 9.6 Hz, 1H), 5.49 (ddd, J=9.0, 5.4, 2.4 Hz, 1H), 5.42 (dd, J=10.2, 3.0 Hz, 1H), 5.31-5.28 (m, 2H), 5.20 (dd, J=27.0, 11.4 Hz, 1H, sia-C4-H), 5.01 (dd, J=51.6, 1.8 Hz, 1H, sia-C3-H), 4.97 (d, J=10.2 Hz, 1H, C1-H_β), 4.66 (d, J=11.4 Hz, 1H), 4.58 (d, J=11.4 Hz, 1H), 4.37 (dd, J=12.6, 2.4 Hz, 1H), 4.28-4.26 (m, 2H), 4.17 (dd, J=12.6, 5.4 Hz, 1H), 4.09-4.05 (m, 2H), 3.98 (dd, J=10.2, 6.0 Hz, 1H), 3.74 (dd, J=10.2, 8.4 Hz, 1H), 3.72 (s, 3H, —CH₃), 2.29 (s, 3H, —CH₃), 2.17 (s, 3H, —CH₃), 2.16 (s, 3H, —CH₃), 2.09 (s, 3H, —CH₃), 1.98 (s, 3H, —CH₃), 1.91 (s, 3H, —CH₃); ¹³C NMR (150 MHz, CDCl₃): δ 170.9, 170.7, 170.4, 170.2, 169.8, 165.6, 165.3, 138.3, 137.6, 133.2, 133.0, 132.6, 129.8, 129.8, 129.7, 129.5, 129.3, 129.1, 128.4, 128.3, 128.1, 127.5, 127.3, 98.3, 98.2, 88.1, 86.8, 86.4, 76.2, 75.6, 74.6, 74.0, 71.4, 69.2, 69.0, 68.5, 68.0, 67.3, 63.4, 62.5, 53.2, 45.5, 23.4, 21.2, 21.2, 20.8, 20.7, 20.7; ¹⁹F NMR (376 MHz, CDCl₃): δ −215.9; HRMS (ESI-TOF) m/e: Calcd for $C_{54}H_{58}FNO_{19}SNa$ [M+Na]⁺: 1098.3200 found 1098.3212.

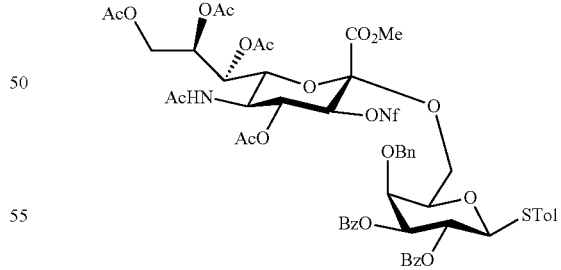

p-Tolyl [methyl 5-acetamido-4,7,8,9-tetra-O-acetyl-5-deoxy-3-O-(perfluoro-1-butane) sulfonyl-D-erythro-α-L-gluco-non-2-ulopyranosonate]-(2→6)-2,3-di-O-benzoyl-4-O-benzyl-1-thio-β-D-galactopyranoside 7. $R_f$=0.59 (silica gel, acetone:toluene=2:3); ¹H NMR (600 MHz, CDCl₃): δ 7.95-7.94 (m, 2H, Ar—H), 7.90-7.89 (m, 2H, Ar—H), 7.49-7.45 (m, 2H, Ar—H), 7.40-7.39 (m, 2H, Ar—H), 7.36-7.30 (m, 4H, Ar—H), 7.27-7.26 (m, 2H, Ar—H), 7.25-7.18 (m, 3H, Ar—H). 7.04-7.03 (m, 2H, Ar—H), 5.82

(dd, J=10.2, 9.6 Hz, 1H), 5.62-5.38 (m, 4H), 5.26 (d, J=9.0 Hz, 1H), 4.96-4.94 (m, 2H, C1-H$_\beta$), 4.70-4.64 (m, 3H), 4.35-4.30 (m, 1H), 4.22-4.20 (m, 2H), 4.09 (dd, J=9.6, 6.0 Hz, 1H), 4.02 (dd, J=12.6, 6.0 Hz, 1H), 3.98 (dd, J=6.6, 6.0 Hz, 1H), 3.93 (dd, J=10.2, 7.2 Hz, 1H), 3.76 (s, 3H, —CH$_3$), 2.29 (s, 3H, —CH$_3$), 2.17 (s, 3H, —CH$_3$), 2.09 (s, 3H, —CH$_3$), 2.06 (s, 3H, —CH$_3$), 1.94 (s, 3H, —CH$_3$), 1.90 (s, 3H, —CH$_3$); $^{13}$C NMR (150 MHz, CDCl$_3$): δ 170.6, 170.2, 170.1, 169.3, 167.0, 165.7, 165.2, 138.1, 137.7, 133.2, 133.0, 132.5, 129.8, 129.7, 129.7, 129.5, 129.1, 129.0, 128.4, 128.3, 128.1, 128.0, 127.5, 127.4, 97.8, 86.5, 83.4, 75.7, 74.6, 74.2, 72.6, 70.0, 68.4, 67.9, 66.5, 64.5, 62.4, 53.1, 49.0, 23.0, 21.1, 20.9, 20.7, 20.6, 20.3; $^{19}$F NMR (376 MHz, CDCl$_3$): δ −126.2, −126.2, −121.5, −121.5, −110.4, −110.4, −81.0, −80.9, −80.9; HRMS (ESI-TOF) m/e: Calcd for C$_{58}$H$_{58}$F$_9$NO$_{22}$S$_2$Na [M+Na]$^+$: 1378.2640 found 1378.2644.

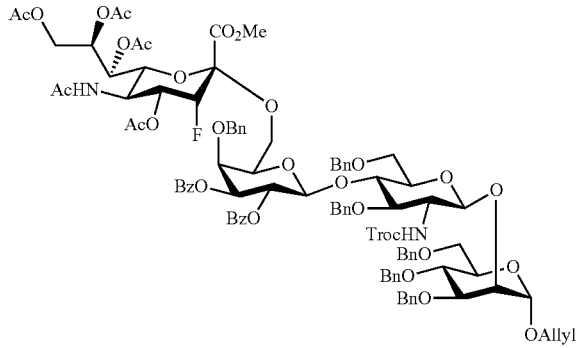

Allyl [methyl 5-acetamido-4,7,8,9-tetra-O-acetyl-3,5-dideoxy-3-fluoro-D-erythro-α-L-manno-non-2-ulopyranosonate]-(2→6)-[2,3-di-O-benzoyl-4-O-benzyl-1-β-D-galactopyranosyl]-(1→4)-[3,6-di-O-benzyl-2-deoxy-2-(2,2,2-trichloroethoxy)carbonylamino-β-D-glucopyranosyl]-(1→2)-3,4,6-tri-O-benzyl-α-D-mannopyranoside 9. A mixture of acceptor 8 (1.04 g, 1.03 mmol, 1 equiv.), donor 4 (1.39 g, 1.29 mmol, 1.25 equiv.) and activated pulverized 4 Å MS (0.70 g) in anhydrous CH$_2$Cl$_2$ (7 mL) was stirred under argon for 1 h. Then, the reaction mixture was cooled to −40° C. and NIS (465 mg, 2.06 mmol, 2 equiv.) was added, followed by TfOH (0.5 M in Et$_2$O, 0.62 mL, 0.31 mmol, 0.3 equiv.) with stirring. Upon completion of the reaction (TLC indicated the disappearance of starting materials after ~2 hrs), the reaction mixture was quenched with Et$_3$N (0.4 mL) and filtered through a pad of Celite. The filtrate was diluted with CH$_2$Cl$_2$ (30 mL), washed with 20% aq. Na$_2$S$_2$O$_3$ (10 mL), satd. aq. NaHCO$_3$ (15 mL) and brine (8 mL). The separated organic layer was dried over MgSO$_4$, and concentrated. The obtained residue was purified by silica gel column chromatography using acetone/toluene (1:2) as eluent to give compound 9 as a white powder (1.30 g, 64%). R$_f$=0.51 (silica gel, acetone:toluene=2:3); $^1$H NMR (600 MHz, CDCl$_3$): δ 7.90-7.88 (m, 4H, Ar—H), 7.48-7.45 (m, 2H, Ar—H), 7.34-7.22 (m, 24H, Ar—H), 7.18-7.13 (m, 10H, Ar—H), 5.85-5.78 (m, 2H), 5.47-5.44 (m, 1H), 5.35-5.32 (m, 4H), 5.24-5.16 (m, 2H), 5.11 (dd, J=10.2, 1.2 Hz, 1H), 5.06-4.97 (m, 3H, C1-H$_\beta$), 4.85-4.73 (m, 4H, C1-H$_\alpha$, C1-H$_\beta$), 4.70-4.54 (m, 6H), 4.53-4.42 (m, 4H), 4.33-4.26 (m, 2H), 4.23-4.18 (m, 3H), 4.14-4.04 (m, 3H), 3.97-3.93 (m, 1H), 3.89-3.81 (m, 5H), 3.73-3.58 (m, 10H), 3.45-3.43 (m, 1H), 3.32-3.30 (m, 1H), 2.16 (s, 3H, —CH$_3$), 2.13 (s, 3H, —CH$_3$), 2.10 (s, 3H, —CH$_3$), 2.01 (s, 3H, —CH$_3$), 1.92 (s, 3H, —CH$_3$); $^{13}$C NMR (150 MHz, CDCl$_3$): δ 170.7, 170.6, 170.4, 170.2, 169.8, 165.6, 165.4, 165.4, 165.1, 153.8, 138.8, 138.6, 138.5, 138.2, 138.2, 138.1, 133.7, 133.2, 133.1, 133.1, 130.8, 130.0, 129.8, 129.6, 129.4, 129.0, 128.4, 128.3, 128.3, 128.2, 128.2, 128.2, 128.1, 128.1, 128.0, 128.0, 127.9, 127.6, 127.6, 127.5, 127.4, 127.3, 127.2, 125.2, 117.1, 100.0, 98.3, 98.2, 96.9, 95.6, 88.1, 86.8, 77.9, 75.0, 74.7, 74.6, 74.5, 74.2, 74.1, 73.9, 73.4, 73.3, 73.1, 73.0, 72.4, 71.9, 71.4, 70.9, 70.9, 69.5, 69.2, 69.1, 69.0, 68.0, 67.9, 67.2, 62.9, 62.3, 57.2, 53.2, 45.5, 23.3, 21.0, 20.7, 20.7, 20.6; $^{19}$F NMR (376 MHz, CDCl$_3$): δ −215.6; HRMS (ESI-TOF) m/e: Calcd for C$_{100}$H$_{108}$Cl$_3$FN$_2$O$_{31}$Na [M+Na]$^+$: 1979.5878 found 1979.5889.

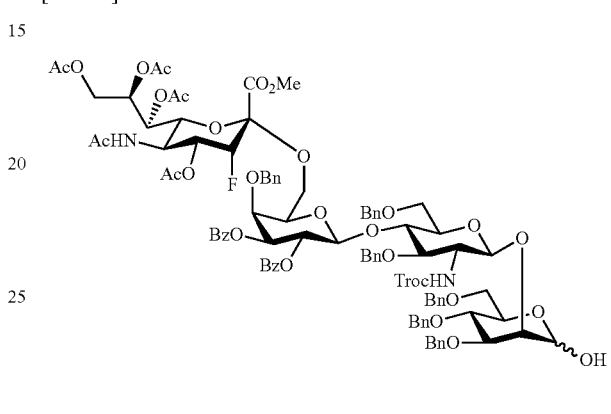

[Methyl 5-acetamido-4,7,8,9-tetra-O-acetyl-3,5-dideoxy-3-fluoro-D-erythro-α-L-manno-non-2-ulopyranosonate]-(2→6)-[2,3-di-O-benzoyl-4-O-benzyl-1-β-D-galactopyranosyl]-(1→4)-[3,6-di-O-benzyl-2-deoxy-2-(2,2,2-trichloroethoxy)carbonylamino-β-D-glucopyranosyl]-(1→2)-3,4,6-tri-O-benzyl-α-D-mannopyranoside 10. To a stirred solution of tetrasaccharide 9 (578 mg, 0.30 mmol, 1 equiv.) in acetic acid (6.0 mL, acetic acid/water, 10:1=v/v) was added CH$_3$COONa (121 mg, 1.48 mmol, 5 equiv.) followed by addition of PdCl$_2$ (105 mg, 0.59 mmol, 2 equiv.) at room temperature. After 20 h, when TLC indicated the disappearance of starting material, the reaction mixture was diluted with ethyl acetate (20 mL) and poured into satd. aq. NaHCO$_3$ (20 mL). The aqueous layer was extracted with ethyl acetate (2×10 mL), and the combined organic phases were dried over MgSO$_4$, and concentrated. The obtained residue was purified by silica gel column chromatography using acetone/hexane (2:3) as eluent to give compound 10 as a white powder (465 mg, 82%). R$_f$=0.23 (silica gel, acetone:hexane=2:3); $^1$H NMR (600 MHz, CDCl$_3$): δ 7.90-7.87 (m, 4H, Ar—H), 7.48-7.45 (m, 2H, Ar—H), 7.34-7.20 (m, 24H, Ar—H), 7.19-7.12 (m, 10H, Ar—H), 5.80-5.75 (m, 1H), 5.45-5.43 (m, 1H), 5.33-5.28 (m, 3H), 5.21-4.89 (m, 5H, man-C1-H$_\alpha$, man-C1-H$_\beta$, C1-H$_\beta$), 4.84-4.30 (m, 15H, C1-H$_\beta$), 4.27-3.79 (m, 12H), 3.78-3.43 (m, 12H), 2.13-2.12 (m, 6H, -2CH$_3$), 2.09-2.08 (m, 3H, —CH$_3$), 2.02-2.00 (m, 3H, —CH$_3$), 1.91 (br, 3H, —CH$_3$); $^{13}$C NMR (150 MHz, CDCl$_3$): δ 170.8, 170.7, 170.7, 170.7, 170.6, 170.5, 170.4, 170.3, 170.3, 170.2, 169.9, 169.8, 165.6, 165.6, 165.4, 165.2, 165.2, 154.0, 138.6, 138.5, 138.3, 138.2, 138.1, 133.2, 133.1, 129.8, 129.6, 129.5, 129.0, 128.4, 128.4, 128.3, 128.3, 128.2, 128.2, 128.2, 128.1, 128.0, 127.9, 127.9, 127.7, 127.7, 127.6, 127.5, 127.5, 127.4, 127.4, 127.3, 100.0, 99.5, 98.3, 98.2, 98.1, 95.8, 95.7, 92.3, 88.2, 88.1, 86.8, 76.1, 74.8, 74.7, 74.6, 74.3, 74.2, 74.2, 73.9, 73.8, 73.3, 73.2, 73.1, 73.1, 72.7, 72.6, 72.4, 72.3, 71.6, 71.4, 71.2, 70.9, 70.8, 69.9, 69.5, 69.3, 69.2, 69.1, 69.0, 68.1, 68.0, 67.2, 67.1, 63.0, 62.3, 62.2, 62.1, 53.3, 53.3, 45.5, 45.4, 26.3, 23.3, 21.1, 20.8, 20.7, 20.7, 20.6, 20.6; $^{19}$F NMR (376 MHz, CDCl$_3$): δ −215.2, −215.7; HRMS (ESI-TOF) m/e: Calcd for C$_{97}$H$_{104}$Cl$_3$FN$_2$O$_{31}$Na [M+Na]$^+$: 1939.5565 found 1939.5619.

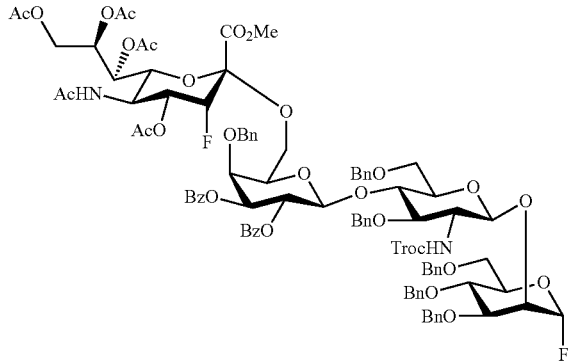

[Methyl 5-acetamido-4,7,8,9-tetra-O-acetyl-3,5-dideoxy-3-fluoro-D-erythro-α-L-manno-non-2-ulopyranosonate]-(2→6)-[2,3-di-O-benzoyl-4-O-benzyl-1-β-D-galactopyranosyl]-(1→4)-[3,6-di-O-benzyl-2-deoxy-2-(2,2,2-trichloroethoxy)carbonylamino-β-D-glucopyranosyl]-(1→2)-3,4,6-tri-O-benzyl-α-D-mannopyranosyl fluoride 11. To a well-stirred solution of hemicetal 10 (395 mg, 0.21 mmol, 1 equiv.) in anhydrous CH$_2$Cl$_2$ (12 mL) was added DAST (81.6 μL, 0.62 mmol, 3 equiv.) at −20° C. The reaction mixture was vigorously stirred until TLC indicated the disappearance of starting material (3 h). The reaction mixture was diluted with CH$_2$Cl$_2$ (10 mL) and washed with satd. aq. NaHCO$_3$ (5 mL) and brine (4 mL). The organic phase was dried over MgSO$_4$, filtered, and concentrated. The obtained residue was purified by silica gel column chromatography using acetone/hexane (3:4) as eluent to give compound 11 as a white powder (289 mg, 73%). R$_f$=0.32 (silica gel, acetone:hexane=3:4); $^1$H NMR (600 MHz, CDCl$_3$): δ 7.89-7.88 (m, 4H, Ar—H), 7.47-7.45 (m, 2H, Ar—H), 7.33-7.22 (m, 22H, Ar—H), 7.17-7.12 (m, 12H, Ar—H), 5.78 (dd, J=10.2, 7.8 Hz, 1H), 5.53-5.40 (m, 2H), 5.33-5.29 (m, 3H, C1-H$_α$), 5.21 (dd, J=27.6, 11.4 Hz, 1H, sia-C4-H), 5.05-4.96 (m, 2H, C1-H$_β$), 4.94 (d, J=11.4 Hz, 1H), 4.82-4.79 (m, 4H, C1-H$_β$), 4.75-4.72 (m, 1H), 4.68-4.59 (m, 3H), 4.58-4.54 (m, 2H), 4.50-4.48 (m, 2H), 4.30 (dd, J=12.6, 3.0 Hz, 1H), 4.26 (d, J=10.2 Hz, 1H), 4.23-4.15 (m, 4H), 4.08-4.04 (m, 2H), 3.95 (dd, J=9.0, 8.4 Hz, 1H), 3.89-3.78 (m, 5H), 3.72-3.57 (m, 9H), 3.50-3.48 (m, 1H), 3.35 (d, J=0.6 Hz, 1H) 2.14 (s, 3H, —CH$_3$), 2.12 (s, 3H, —CH$_3$), 2.09 (s, 3H, —CH$_3$), 2.00 (s, 3H, —CH$_3$), 1.91 (s, 3H, —CH$_3$); $^{13}$C NMR (150 MHz, CDCl$_3$): δ 170.8, 170.7, 170.4, 170.2, 169.9, 165.6, 165.4, 165.2, 153.9, 138.2, 138.1, 137.8, 133.2, 133.1, 129.8, 129.6, 129.4, 129.0, 128.4, 128.3, 128.2, 128.1, 128.0, 127.9, 127.7, 127.6, 127.6, 127.4, 127.3, 127.3, 106.9, 105.4, 99.8, 99.2, 98.3, 98.2, 95.6, 88.1, 86.8, 74.9, 74.8, 74.2, 74.0, 73.9, 73.8, 73.3, 73.2, 72.5, 71.4, 71.3, 70.9, 69.1, 69.1, 68.9, 68.0, 67.3, 62.8, 62.3, 56.9, 53.3, 45.6, 23.4, 21.1, 20.8 (2C), 20.6; $^{19}$F NMR (376 MHz, CDCl$_3$): δ −138.6, −215.7; HRMS (ESI-TOF) m/e: Calcd for C$_{97}$H$_{103}$Cl$_3$F$_2$N$_2$O$_{30}$Na [M+Na]$^+$: 1941.5521 found 1941.5521.

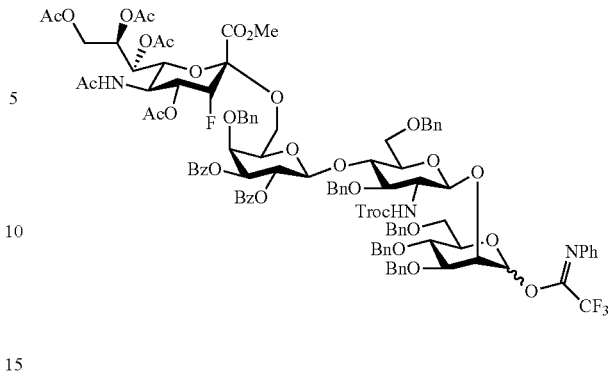

(N-Phenyl)-2,2,2-trifluoroacetimidate [methyl 5-acetamido-4,7,8,9-tetra-O-acetyl-3,5-dideoxy-3-fluoro-D-erythro-α-L-manno-non-2-ulopyranosonate]-(2→6)-[2,3-di-O-benzoyl-4-O-benzyl-1-β-D-galactopyranosyl]-(1→4)-[3,6-di-O-benzyl-2-deoxy-2-(2,2,2-trichloroethoxy)carbonylamino-β-D-glucopyranosyl]-(1→2)-3,4,6-tri-O-benzyl-D-mannopyranoside 12. To a well-stirred solution of hemicetal 10 (395 mg, 0.21 mmol, 1 equiv.) in anhydrous CH$_2$Cl$_2$ (12 mL) was added Cs$_2$CO$_3$ (83.2 mg, 0.26 mmol, 2 equiv.) and 2,2,2-trifluoro-N-phenyl-acetimidoyl chloride (41 μL, 0.26 mmol, 2 equiv.) at 0° C. with stirring, and then the mixture was warmed up to room temperature and stirred for 3 h. The reaction mixture was diluted with CH$_2$Cl$_2$ (10 mL), filtered through a pad of Celite, and concentrated. The obtained residue was purified by silica gel column chromatography using acetone/hexane (1:2) as eluent to give compound 12 as a white foam (150 mg, 56%); anomeric mixture (α:β=1:1). R$_f$=0.55 (silica gel, acetone:hexane=1:1); $^1$H NMR (600 MHz, CDCl$_3$): δ 7.93-7.88 (m, 4H, Ar—H), 7.49-7.45 (m, 2H, Ar—H), 7.40-7.12 (m, 38H, Ar—H), 6.75-6.71 (m, 1H, Ar—H), 5.82-5.78 (m, 1H), 5.46-5.42 (m, 1H), 5.36-5.30 (m, 3H), 5.24-5.16 (m, 1H), 5.08-4.81 (m, 5H, 0.5man-C1-H$_α$, 2C1-H$_β$), 4.78-4.74 (m, 1H), 4.69-4.41 (m, 9H, 0.5man-C1-H$_β$), 4.33-4.06 (m, 7H), 3.95-3.82 (m, 5H), 3.69-3.36 (m, 10H), 2.16-2.10 (m, 9H, -3CH$_3$), 2.01-1.99 (m, 3H, —CH$_3$), 1.92 (s, 3H, —CH$_3$); $^{13}$C NMR (150 MHz, CDCl$_3$): δ 170.7, 170.7, 170.7, 170.7, 170.4, 170.2, 169.9, 169.9, 165.6, 165.6, 165.4, 165.2, 165.1, 154.1, 153.9, 143.3, 143.1, 138.7, 138.5, 138.3, 138.2, 138.2, 138.1, 138.0, 138.0, 137.8, 137.7, 133.2, 133.1, 133.1, 129.8, 129.6, 129.4, 129.3, 129.0, 128.7, 128.4, 128.4, 128.3, 128.3, 128.3, 128.2, 128.2, 128.1, 128.1, 128.1, 128.0, 127.9, 127.7, 127.7, 127.6, 127.5, 127.5, 127.5, 127.4, 127.3, 119.4, 119.2, 102.3, 100.2, 100.0, 98.3, 98.2, 95.6, 95.5, 88.0, 86.7, 80.0, 79.3, 75.9, 75.0, 74.7, 74.7, 74.5, 74.3, 74.2, 73.8, 73.8, 73.5, 73.3, 73.2, 73.1, 72.8, 72.4, 72.3, 71.5, 71.4, 71.1, 71.0, 70.9, 70.1, 69.8, 69.3, 69.1, 68.2, 67.2, 67.2, 62.8, 62.3, 62.2, 53.3, 53.2, 45.5, 23.3, 21.0, 21.0, 20.7, 20.7, 20.6; $^{19}$F NMR (376 MHz, CDCl$_3$): δ −65.2, −65.4, −65.5, −65.6, −65.6, −65.7, −215.6, −215.7; HRMS (ESI-TOF) m/e: Calcd for C$_{105}$H$_{108}$Cl$_3$F$_4$N$_3$O$_{31}$Na [M+Na]$^+$: 2110.5860 found 2110.5865.

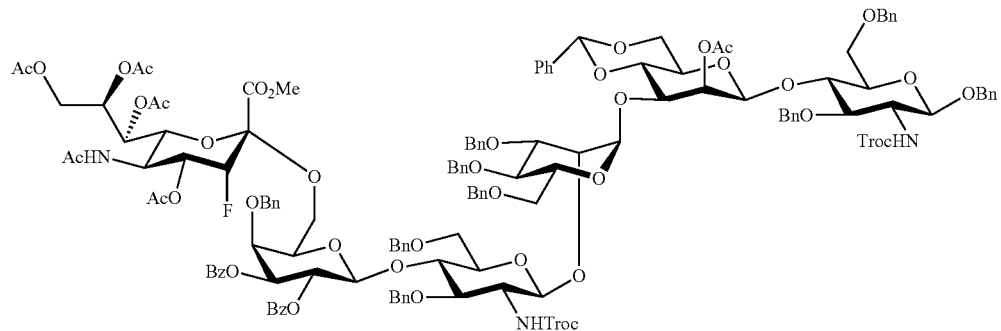

Benzyl [methyl 5-acetamido-4,7,8,9-tetra-O-acetyl-3,5-dideoxy-3-fluoro-D-erythro-α-L-manno-non-2-ulopyranosonate]-(2→6)-[2,3-di-O-benzoyl-4-O-benzyl-1-β-D-galactopyranosyl]-(1→4)-[3,6-di-O-benzyl-2-deoxy-2-(2,2,2-trichloroethoxy)carbonylamino-β-D-glucopyranosyl]-(1→2)-[3,4,6-tri-O-benzyl-α-D-mannopyranosyl]-(1→3)-[2-O-acetyl-4,6-O-benzylidene-β-D-mannopyranosyl]-(1→4)-3,6-di-O-benzyl-2-deoxy-2-(2,2,2-trichloroethoxy)carbonylamino-β-D-glucopyranoside 14. A mixture AgOTf (194 mg, 0.75 mmol, 6 equiv. with respect to acceptor), bis Cp$_2$HfCl$_2$ (167 mg, 0.44 mmol, 3.5 equiv. with respect to acceptor), and freshly activated 4 Å MS (1.50 g) in anhydrous toluene (15 mL) was stirred at room temperature under argon for 1 h. Then, the reaction mixture was cooled to −20° C. and treated with a solution of donor 11 (290 mg, 0.15 mmol, 1.2 equiv.) and acceptor 13 (115 mg, 0.13 mmol, 1 equiv.) in anhydrous toluene (8 mL). The reaction mixture was stirred at 0° C. until TLC indicated the disappearance of starting material (3 hrs). Upon completion of the reaction, the reaction mixture was quenched with Et$_3$N (0.25 mL), diluted with EtOAc (25 mL), and filtered through a pad of Celite. The filtrate was washed twice with satd. aq. NaHCO$_3$ (10 mL) and brine (6 mL), and the organic phase was dried over MgSO$_4$, filtered, and concentrated. The obtained residue was purified by silica gel column chromatography using acetone/toluene (1:2) as eluent to give compound 14 as a white powder (299 mg, 85%).

One-pot Synthesis: A mixture of acceptor 18 (40.0 mg, 0.037 mmol, 1 equiv.), donor 4 (60.1 mg, 0.056 mmol, 1.5 equiv.) and activated pulverized 4 Å MS (0.25 g) in anhydrous CH$_2$Cl$_2$ (1.25 mL) was stirred under argon for 1 h. Then, the reaction mixture was cooled to −40° C. and NIS (12.6 mg, 0.056 mmol, 1.5 equiv.) was added, followed by TfOH (0.5 M in Et$_2$O, 22.3 μL, 0.011 mmol, 0.3 equiv.) and the mixture was then allowed to stir to −20° C. for 2 h. Next, upon disappearance of starting materials (monitored by TLC), the reaction mixture was treated sequentially with acceptor 13 (34.2 mg, 0.037 mmol, 1 equiv.), NIS (16.8 mg, 0.075 mmol, 2 equiv.) and TfOH (0.5 M in Et$_2$O, 22.3 μL, 0.011 mmol, 0.3 equiv.) in anhydrous CH$_2$Cl$_2$ (1.25 mL) with stirring for 10 min under argon. Upon addition of all the reagents, the mixture was allowed to warm up to −10° C. and continued to stir until TLC indicated the disappearance of starting materials (1 h). Upon completion, the reaction was quenched with Et$_3$N (0.4 mL) and filtered through a pad of Celite. The filtrate was diluted with CH$_2$Cl$_2$ (10 mL), washed with 20% aq. Na$_2$S$_2$O$_3$ (3 mL), satd. aq. NaHCO$_3$ (2 mL) and brine (2 mL). The separated organic layer was dried over MgSO$_4$, filtered and concentrated in vacuo. The obtained residue was purified by silica gel column chromatography using acetone/toluene (1:2) as eluent, followed by a second column chromatography using acetone/hexane (3:4) as eluent to give compound 14 as a white powder (27 mg, 26%). $R_f$=0.43 (silica gel, acetone:toluene=3:5); $^1$H NMR (600 MHz, CDCl$_3$): δ 7.96-7.95 (m, 2H, Ar—H), 7.91-7.90 (m, 2H, Ar—H), 7.51-7.47 (m, 2H, Ar—H), 7.36-7.26 (m, 35H, Ar—H), 7.23-7.10 (m, 19H, Ar—H), 5.84 (dd, J=10.2, 7.8 Hz, 1H), 5.45-5.42 (m, 1H), 5.34-5.27 (m, 4H), 5.21-5.15 (m, 2H), 5.04-4.94 (m, 4H, C1-H$_α$, C1-H$_β$), 4.87-4.78 (m, 4H), 4.71-4.50 (m, 14H, 2C1-H$_β$), 4.46-4.34 (m, 5H), 4.31-4.21 (m, 4H), 4.16 (dd, J=12.6, 5.4 Hz, 1H), 4.13-4.06 (m, 2H), 3.98-3.95 (m, 4H, C1-H$_β$), 3.84-3.57 (m, 17H), 3.51-3.41 (m, 4H), 3.36-3.35 (m, 2H), 3.15 (br, 1H), 2.93 (br, 1H), 2.68-2.67 (m, 1H), 2.12 (s, 3H, —CH$_3$), 2.11 (s, 3H, —CH$_3$), 2.09 (s, 3H, —CH$_3$), 1.99 (s, 3H, —CH$_3$), 1.91 (s, 3H, —CH$_3$), 1.85 (s, 3H, —CH$_3$); $^{13}$C NMR (150 MHz, CDCl$_3$): δ 170.8, 170.7, 170.4, 170.2, 169.7, 169.4, 165.6, 165.4, 165.2, 153.7, 153.6, 138.9, 138.7, 138.4, 138.3, 137.9, 137.1, 133.2, 129.8, 129.7, 129.5, 129.1, 128.9, 128.6, 128.5, 128.4, 128.4, 128.3, 128.3, 128.2, 128.1, 128.1, 128.0, 128.0, 127.9, 127.9, 127.9, 127.8, 127.8, 127.6, 127.6, 127.6, 127.5, 127.4, 127.4, 127.3, 127.2, 126.3, 102.1, 100.1, 99.0, 98.7, 98.6, 95.8, 95.5, 88.2, 86.9, 78.8, 78.4, 74.8, 74.5, 74.3, 74.2, 73.9, 73.8, 73.3, 72.9, 72.3, 71.9, 71.4, 71.1, 70.7, 70.3, 69.2, 69.1, 69.0, 68.4, 68.3, 67.9, 67.2, 66.2, 63.2, 62.3, 57.4, 56.8, 53.3, 45.5, 23.3, 21.0, 20.8, 20.7, 20.6, 20.6; $^{19}$F NMR (376 MHz, CDCl$_3$): δ −215.6; HRMS (ESI-TOF) m/e: Calcd for C$_{142}$H$_{150}$Cl$_6$FN$_3$O$_{43}$Na$_2$ [M+2Na]$^{2+}$: 1429.8771 found 1429.8864.

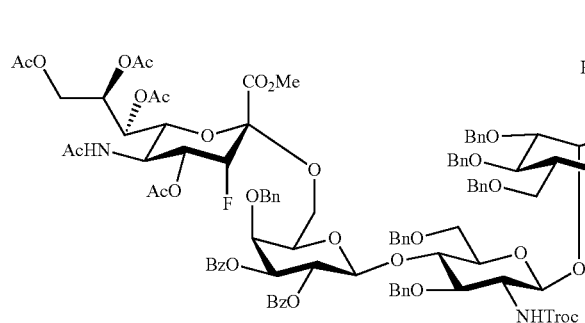
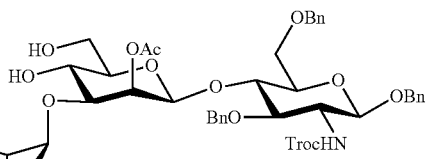

Benzyl [methyl 5-acetamido-4,7,8,9-tetra-O-acetyl-3,5-dideoxy-3-fluoro-D-erythro-α-L-manno-non-2-ulopyranosonate]-(2→6)-[2,3-di-O-benzoyl-4-O-benzyl-1-β-D-galactopyranosyl]-(1→4)-[3,6-di-O-benzyl-2-deoxy-2-(2,2,2-trichloroethoxy)carbonylamino-β-D-glucopyranosyl]-(1→2)-[3,4,6-tri-O-benzyl-α-D-mannopyranosyl]-(1→3)-[2-O-acetyl-β-D-mannopyranosyl]-(1→4)-3,6-di-O-benzyl-2-deoxy-2-(2,2,2-trichloroethoxy)carbonylamino-β-D-glucopyranoside 15. To a stirred solution of starting material 14 (318 mg, 0.11 mmol, 1 equiv.) in acetonitrile (12 mL) was added p-TsOH·H$_2$O (21.5 mg, 0.11 mmol, 1 equiv.). The reaction mixture was vigorously stirred until TLC indicated the disappearance of starting material (6 hrs). Upon completion, the reaction mixture was quenched with Et$_3$N (0.3 mL) and concentrated under high vacuum. The obtained residue was purified by silica gel column chromatography using acetone/toluene (3:5) as eluent to give compound 15 as a white powder (231 mg, 75%). R$_f$=0.25 (silica gel, acetone: toluene=1:2); $^1$H NMR (600 MHz, CDCl$_3$): δ 7.88-7.87 (m, 4H, Ar—H), 7.46 (dd, J=7.2, 7.2 Hz, 1H, Ar—H), 7.43 (dd, J=7.2, 7.2 Hz, 1H, Ar—H), 7.33-7.13 (m, 47H, Ar—H), 7.09-7.08 (m, 2H, Ar—H), 6.01 (br, 1H), 5.76 (dd, J=10.2, 7.8 Hz, 1H), 5.46-5.43 (m, 1H), 5.38 (d, J=8.4 Hz, 1H), 5.31-5.29 (m, 3H), 5.19-5.13 (m, 2H, C1-H$_α$), 5.05-4.96 (m, 3H, C1-H$_β$), 4.89-4.79 (m, 4H, C1-H$_β$), 4.69-4.60 (m, 8H, C1-H$_β$), 4.57-4.49 (m, 8H, C1-H$_β$), 4.45 (d, J=12.0 Hz, 1H), 4.40-4.36 (m, 2H), 4.31 (dd, J=12.6, 2.4 Hz, 1H), 4.24-4.16 (m, 4H), 4.12-4.09 (m, 2H), 4.02 (br, 1H), 3.98-3.93 (m, 2H), 3.91-3.86 (m, 2H), 3.80 (dd, J=7.8, 6.0 Hz, 1H), 3.76-3.69 (m, 6H), 3.66-3.37 (m, 18H), 2.96-2.93 (m, 1H), 2.13 (s, 3H, —CH$_3$), 2.11 (s, 3H, —CH$_3$), 2.09 (s, 3H, —CH$_3$), 1.98 (s, 3H, —CH$_3$), 1.93 (s, 3H, —CH$_3$), 1.90 (s, 3H, —CH$_3$); $^{13}$C NMR (150 MHz, CDCl$_3$): δ 170.8, 170.7, 170.4, 170.3, 170.2, 169.8, 165.6, 165.5, 165.3, 154.3, 153.8, 138.6, 138.4, 138.3, 138.1, 138.0, 137.8, 137.2, 133.3, 133.1, 129.8, 129.6, 129.4, 129.0, 128.5, 128.4, 128.3, 128.2, 128.2, 127.9, 127.9, 127.8, 127.7, 127.6, 127.5, 127.5, 127.4, 127.4, 127.3, 100.1, 99.1, 98.3, 98.2, 98.1, 95.7, 95.5, 88.2, 86.9, 78.6, 78.2, 75.4, 75.1, 74.8, 74.7, 74.4, 74.2, 74.1, 73.8, 73.3, 73.2, 72.6, 71.9, 71.8, 71.5, 71.4, 70.9, 70.6, 69.5, 62.3, 57.2, 56.8, 53.8, 53.3, 45.4, 23.3, 21.1, 21.0, 20.7 (2C), 20.7; $^{19}$F NMR (376 MHz, CDCl$_3$): δ −215.6; HRMS (ESI-TOF) m/e: Calcd for C$_{135}$H$_{146}$Cl$_6$FN$_3$O$_{43}$Na [M+Na]$^+$: 2748.7337 found 2748.7373.

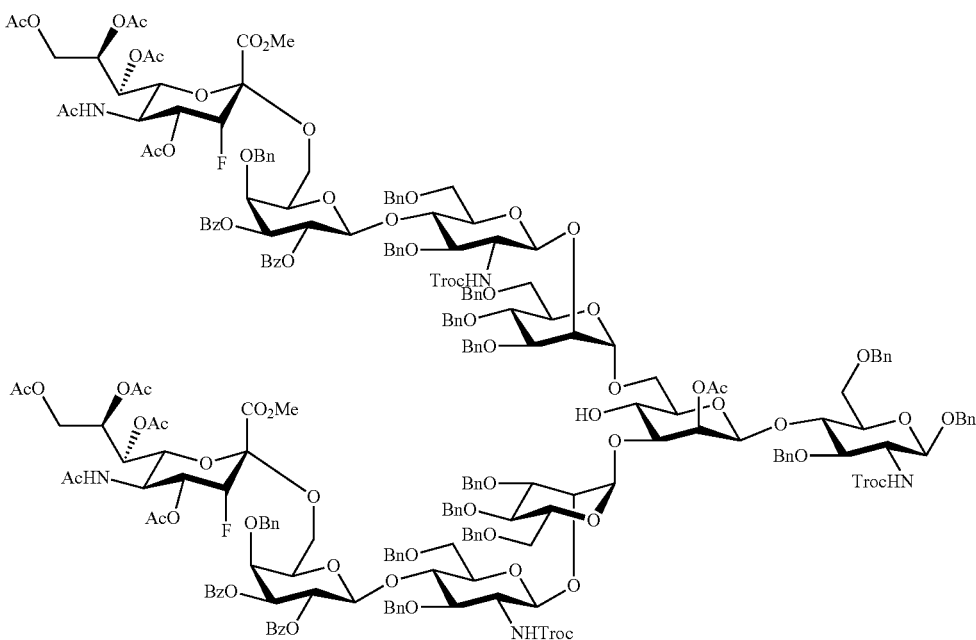

Benzyl [methyl 5-acetamido-4,7,8,9-tetra-O-acetyl-3,5-dideoxy-3-fluoro-D-erythro-α-L-manno-non-2-ulopyranosonate-(2→6)-2,3-di-O-benzoyl-4-O-benzyl-1-β-D-galactopyranosyl-(1→4)-3,6-di-O-benzyl-2-deoxy-2-(2,2,2-trichloroethoxy)carbonylamino-β-D-glucopyranosyl-(1→2)-3,4,6-tri-O-benzyl-α-D-mannopyranosyl-(1→3)]-[methyl 5-acetamido-4,7,8,9-tetra-O-acetyl-3,5-dideoxy-3-fluoro-D-erythro-α-L-manno-non-2-ulopyranosonate-(2→6)-2,3-di-O-benzoyl-4-O-benzyl-1-β-D-galactopyranosyl-(1→4)-3,6-di-O-benzyl-2-deoxy-2-(2,2,2-trichloroethoxy)carbonylamino-β-D-glucopyranosyl-(1→2)-3,4,6-tri-O-benzyl-α-D-mannopyranosyl-(1→6)]-[2-O-acetyl-f-D-mannopyranosyl]-(1→4)-3,6-di-O-benzyl-2-deoxy-2-(2,2,2-trichloroethoxy)carbonylamino-β-D-glucopyranoside 16.

From fluoride donor: A mixture of AgOTf (142 mg, 0.55 mmol, 8 equiv. with respect to acceptor), Cp$_2$HfCl$_2$ (105 mg, 0.28 mmol, 4 equiv. with respect to acceptor), and freshly activated 4 Å MS (1 g) in anhydrous toluene (10 mL) was stirred at room temperature under argon atmosphere for 1 h. Then, the reaction mixture was cooled to −40° C. and a solution of donor 11 (232 mg, 0.12 mmol, 1.75 equiv.) and acceptor 15 (188 mg, 0.069 mmol, 1 equiv.) in anhydrous toluene (1 mL) was added. Stirring was continued at −15° C. for 3 h. The reaction mixture was quenched with Et$_3$N (0.20 mL), diluted with EtOAc (20 mL), and filtered through a pad of Celite. The filtrate was washed twice with satd. aq. NaHCO$_3$ (8 mL) and brine (4 mL). The organic phase was dried over MgSO$_4$, filtered and concentrated in vacuo. The obtained residue was purified by silica gel column chromatography using acetone/toluene (2:3) as eluent to give compound 16 as a white powder (223 mg, 70%) along with the recovered 15 (23.0 mg, 80% brsm).

From trifluoroacetimidate donor: A mixture of acceptor 15 (32.0 mg, 0.012 mmol, 1 equiv.), donor 12 (42.9 mg, 0.021 mmol, 1.75 equiv.) and activated pulverized 4 Å MS (200 mg) in anhydrous CH$_2$Cl$_2$ (2 mL) was stirred under argon for 30 min. Then, the reaction mixture was cooled to −60° C. and treated with TfOH (0.5 M in Et$_2$O, 5.86 μL, 2.93 μmol, 0.25 equiv. with respect to acceptor). After stirring at −20° C. for 3 h. the reaction mixture was quenched with Et$_3$N (0.10 mL), diluted with CH$_2$Cl$_2$ (10 mL), and filtered through a pad of Celite. The filtrate was washed twice with satd. aq. NaHCO$_3$ (4 mL) and brine (3 mL). The organic phase was dried over MgSO$_4$, filtered, and concentrated. The obtained residue was purified by silica gel column chromatography using acetone/toluene (2:3) as eluent to give compound 16 as a white powder (18.0 mg, 33%) along with the recovered acceptor (12.6 mg, 55% brsm). R$_f$=0.17 (silica gel, acetone:toluene=1:2); $^1$H NMR (600 MHz, CDCl$_3$): δ 7.91-7.86 (m, 8H, Ar—H), 7.48-7.42 (m, 4H, Ar—H), 7.33-7.11 (m, 83H, Ar—H), 5.81-5.75 (m, 2H), 5.43-5.38 (m, 3H), 5.31-5.07 (m, 11H, 2C1-H$_α$), 5.03-4.78 (m, 9H, 2C1-H$_β$), 4.75-4.08 (m, 48H, 4C1-H$_β$), 4.05-3.89 (m, 7H), 3.87-2.99 (m, 40H), 2.13-2.12 (m, 6H, -2CH$_3$), 2.10-2.07 (m, 15H, -5CH$_3$), 1.99-1.97 (s, 6H, -2CH$_3$), 1.90-1.88 (m, 6H, -2CH$_3$); $^{13}$C NMR (150 MHz, CDCl$_3$): δ 170.7, 170.6, 170.6, 170.4, 170.2, 169.8, 169.7, 169.6, 165.6, 165.5, 165.4, 165.4, 165.1, 154.0, 153.6, 139.1, 138.8, 138.4, 138.3, 138.1, 138.0, 137.7, 133.2, 133.1, 129.8, 129.8, 129.7, 129.6, 129.6, 129.5, 129.5, 129.1, 129.1, 128.4, 128.4, 128.3, 128.2, 128.2, 128.0, 128.0, 127.8, 127.8, 127.8, 127.7, 127.7, 127.5, 127.4, 127.4, 127.3, 127.2, 127.1, 100.1, 99.8, 98.8, 98.4, 98.2, 95.7, 88.1, 86.8, 78.3, 77.8, 75.3, 74.7, 74.5, 74.4, 74.3, 74.2, 74.0, 73.9, 73.4, 73.3, 73.3, 73.2, 73.1, 73.0, 72.9, 72.5, 72.4, 72.0, 71.9, 71.5, 71.0, 71.0, 70.9, 70.9, 70.7, 69.5, 69.4, 69.2, 69.1, 69.0, 69.0, 68.5, 68.1, 68.1, 68.0, 67.2, 62.9, 62.2, 57.5, 57.2, 53.8, 53.2, 53.2, 45.5, 45.3, 23.3, 21.0, 21.0, 20.8, 20.7, 20.7, 20.6; $^{19}$F NMR (376 MHz, CDCl$_3$): δ −215.6 (2F); HRMS (ESI-TOF) m/e: Calcd for C$_{232}$H$_{255}$Cl$_9$F$_2$N$_6$O$_{74}$ [M+H$_3$O+NH$_4$]$^{2+}$: 2330.6770 found 2330.6724.

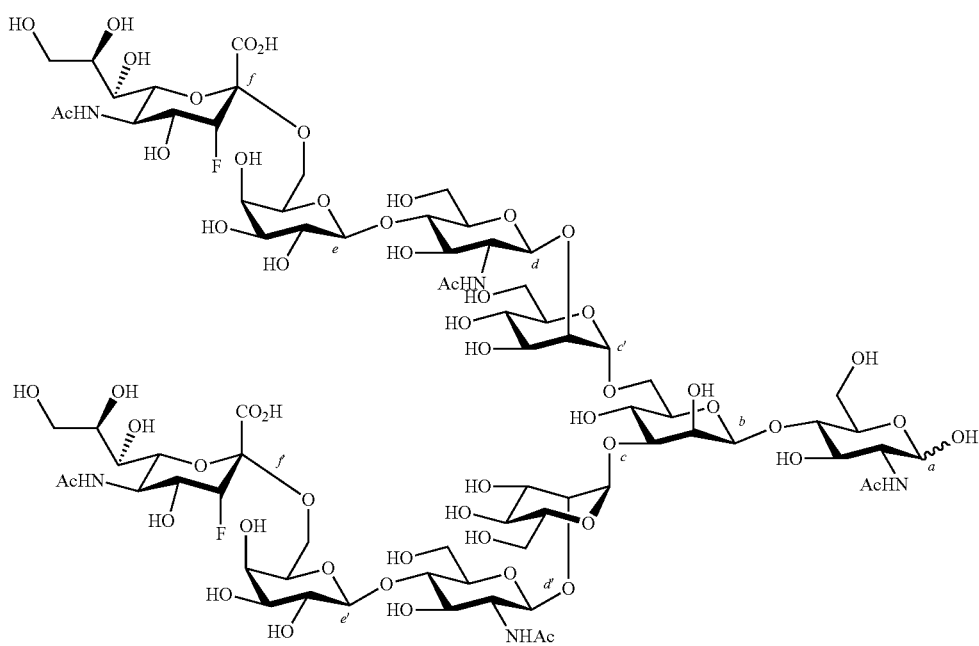

[5-Acetamido-3,5-dideoxy-3-fluoro-D-erythro-α-L-manno-non-2-ulopyranosonate-(2→6)-β-D-galactopyranosyl-(1→4)-2-acetamido-2-deoxy-β-D-glucopyranosyl-(1→2)-α-D-mannopyranosyl-(1→3)]-[5-acetamido-3,5-dideoxy-3-fluoro-D-erythro-α-L-manno-non-2-ulopyranosonate-(2→6)-β-D-galactopyranosyl-(1→4)-2-acetamido-2-deoxy-β-D-glucopyranosyl-(1→2)-α-D-mannopyranosyl-(1→6)]-[β-D-mannopyranosyl]-(1→4)-2-acetamido-2-deoxy-D-glucopyranoside 17. A solution of protected glycan 16 (103 mg, 0.022 mmol, 1 equiv.) and LiOH (51.5 mg, 50% by S.M. wt) in a mixture of 1,4-dioxane/H$_2$O (3 mL, 4:1=v/v) was stirred at 90° C. for 16 h. The reaction mixture was concentrated under high vacuum and subjected to the acetylation conditions (pyridine (2.5 mL), Ac$_2$O (1.5 mL), r.t., 16 h). After the solvent was removed, the crude residue was purified by LiChroprep® RP-18 reverse-phase column chromatography using H$_2$O/MeOH (1:5) as eluent. The product was deacetylated by stirring with NaOMe in MeOH (3 mL, 0.5 M) for 16 h. The reaction mixture was neutralized with IR-120, filtered, and concentrated in vacuo. The residue was purified by LiChroprep® RP-18 reverse-phase column chromatography using H$_2$O/MeOH (1:4) as eluent. The crude product of deacetylation was dissolved in a mixture of MeOH/H$_2$O/HCOOH (3 mL, 6:3:1=v/v/v) and treated with Pd(OH)$_2$ (51.5 mg, 50% by S.M. wt) for 20 h. The reaction mixture was filtered through a pad of Celite and concentrated in vacuo. The residue was purified by (BIO-RAD) Biogel P-2 column chromatography (eluted with water), followed by purification with LiChroprep® RP-18 reverse-phase column chromatography (eluted with water) to give compound 17 as a white powder (18.3 mg, 40%) of anomeric mixture (α:β=0.65:0.35). $^1$H NMR (600 MHz, D$_2$O): δ 5.23 (d, J=3.0 Hz, 0.65H, a-C1-H$_\alpha$), 5.14 (d, J=52.8 Hz, 2H, sia-C3-H), 5.14 (br, 1H, c-C1-H$_\alpha$), 4.96 (br, 1H, c'-C1-H$_\alpha$), 4.79 (br, 1H, b-C1-H$_\beta$), 4.73 (br, 0.35H, a-C1-H$_\beta$), 4.60 (d, J=7.8 Hz, 2H, dd'-C1-H$_\beta$), 4.48 (d, J=7.8 Hz, 2H, ee'-C1-H$_\beta$), 4.28-4.21 (m, 4H), 4.13 (br, 1H), 4.00-3.51 (m, 57H), 2.09-2.08 (m, 9H, -3CH$_3$), 2.05 (br, 6H, -2CH$_3$); $^{13}$C NMR (150 MHz, D$_2$O): δ 174.5, 174.2, 174.1, 102.7, 102.6, 100.0, 99.1, 98.9, 98.9, 98.7, 98.6, 96.6, 94.4, 91.0, 90.0, 89.8, 80.0, 79.7, 79.3, 78.9, 76.0, 75.8, 74.1, 74.0, 73.9, 73.1, 72.9, 72.7, 72.4, 71.9, 71.9, 71.6, 71.5, 71.1, 70.3, 69.8, 69.4, 69.2, 69.1, 69.0, 68.7, 68.0, 67.8, 66.9, 66.8, 65.4, 65.2, 63.6, 62.2, 61.2, 61.2, 59.7, 59.6, 55.6, 54.4, 53.1, 46.3, 21.9, 21.6; $^{19}$F NMR (376 MHz, D$_2$O): δ −217.4, −217.4; HRMS (ESI-TOF) m/e: Calcd for C$_{76}$H$_{121}$F$_2$N$_5$O$_{57}$ [M-2H]$^{-2}$:1026.8351 found 1026.8299.

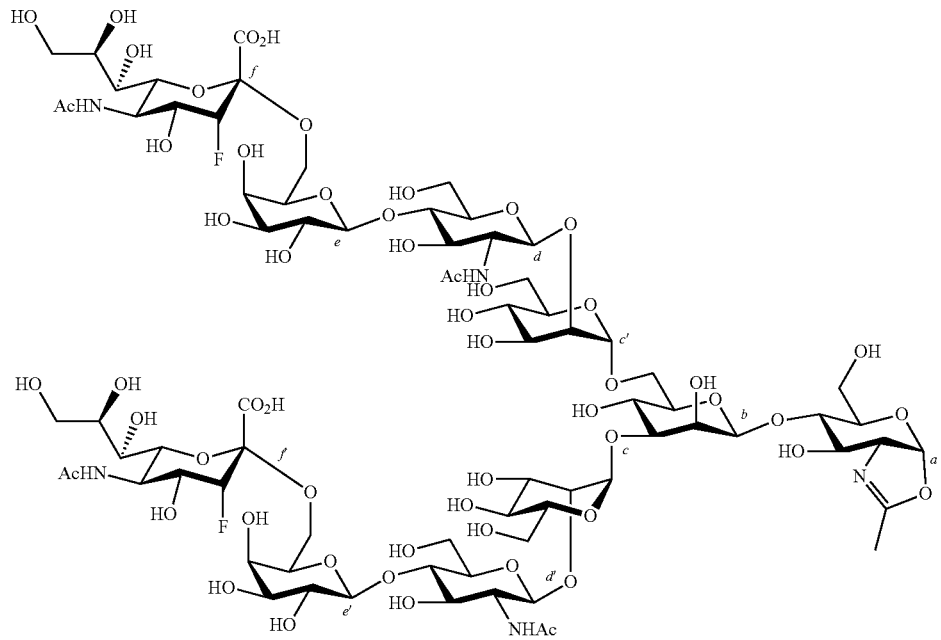

[5-Acetamido-3,5-dideoxy-3-fluoro-D-erythro-α-L-manno-non-2-ulopyranosonate-(2→6)-β-D-galactopyranosyl-(1→4)-2-acetamido-2-deoxy-β-D-glucopyranosyl-(1→2)-α-D-mannopyranosyl-(1→3)]-[5-acetamido-3,5-dideoxy-3-fluoro-D-erythro-α-L-manno-non-2-ulopyranosonate-(2→6)-β-D-galactopyranosyl-(1→4)-2-acetamido-2-deoxy-β-D-glucopyranosyl-(1→2)-α-D-mannopyranosyl-(1→6)]-[β-D-mannopyranosyl]-(1→4)-(2-acetamido-1,2-dideoxy-D-glucopyrano)-[2,1-d]-2-methyloxazoline S1. Representative synthesis of glycan oxazoline. A solution of glycan 17 (14.5 mg, 7.05 μmol, 1 equiv.), 2-Chloro-1,3-dimethyl-1H-benzimidazol-3-ium chloride (CDMBI) (12.2 mg, 0.056 mmol, 8 equiv.) and Et$_3$N (19.9 μL) in water (121.1 μL) was stirred at 4° C. for 1 h. The reaction mixture was subjected to gel filtration chromatography on a Sephadex G-25 column and eluted with 0.05% aq. Et$_3$N. The fractions containing the glycan oxazoline product were combined and lyophilized to give the desired product S1 as a white powder (12.6 mg, yield 87%). $^1$H NMR (600 MHz, D$_2$O+0.05% Et$_3$N): δ 6.09 (d, J=7.2 Hz, 1H, oxa-C1-H$_α$), 5.12 (d, J=52.2 Hz, 2H, sia-C3-H), 5.11 (br, 1H, c-C1-H$_α$), 4.95 (br, 1H, c'-C1-H$_α$), 4.74 (br, 1H, b-C1-H$_β$), 4.60-4.57 (m, 2H, dd'-C1-H$_β$), 4.46-4.45 (m, 2H, ee'-C1-H$_β$), 4.39 (br, 1H), 4.22-4.15 (m, 5H), 3.98-3.49 (m, 55H), 3.43-3.40 (m, 1H), 2.07-2.02 (m, 15H, -5CH$_3$); $^{13}$C NMR (150 MHz, D$_2$O+0.05% Et$_3$N): δ 174.9, 174.7, 174.7, 170.7, 170.7, 168.5, 103.1, 103.1, 101.4, 99.9, 99.5, 99.4, 99.2, 99.1, 99.0, 96.5, 91.4, 90.2, 80.4, 79.4, 77.9, 76.4, 76.0, 74.6, 74.2, 73.4, 73.4, 72.8, 72.4, 72.3, 72.0, 71.9, 71.5, 70.8, 70.7, 70.2, 69.6, 69.5, 69.4, 69.1, 68.5, 68.2, 67.2, 65.8, 65.7, 65.1, 64.1, 62.6, 61.6, 61.6, 60.1, 54.9, 46.7, 22.4, 22.0, 12.9; $^{19}$F NMR (470 MHz, D$_2$O+0.05% Et$_3$N): δ −217.3 (d, J$_{FH}$=51.3 Hz), −217.3 (d, J$_{FH}$=51.3 Hz); HRMS (ESI-TOF) m/e: Calcd for C$_{76}$H$_{120}$F$_2$N$_5$O$_{56}$ [M−H]$^-$: 2036.6658 found 2036.6672.

Scheme S1.

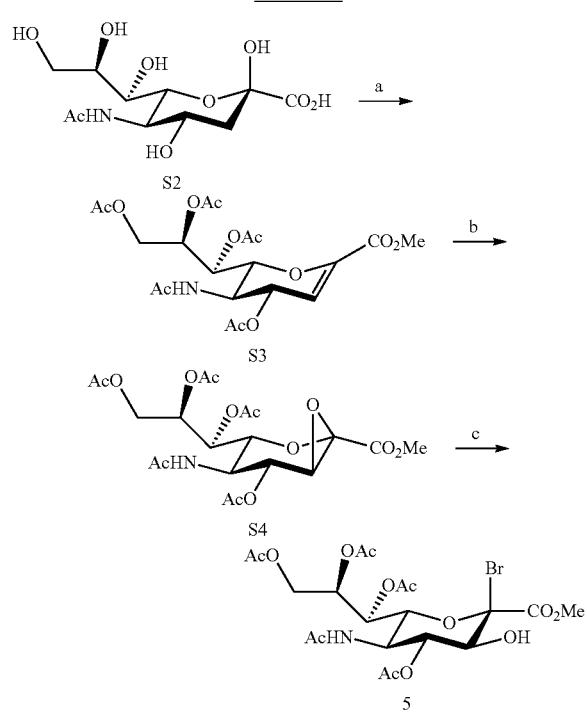

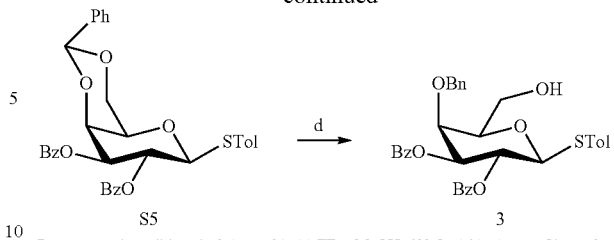

Reagents and conditions in Scheme S1: (a) TFA, MeOH, 60° C., 16 h, then AcCl, r.t., 2 d, then Na$_2$HPO$_4$, CH$_3$CN, reflux, 20 h, 92%. (b) ref. 3, 80% (three steps). (c) TiBr$_4$, dichloroethane, r.t., 10 min., 92%. (d) BH$_3$, Cu(OTf)$_2$, THF, r.t., 8 h, 96%.

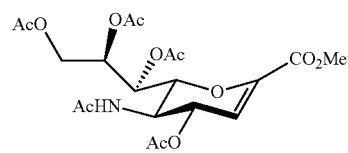

Methyl 5-acetamido-4,7,8,9-tetra-O-acetyl-3,5-dideoxy-2,6-anhydro-D-glycero-D-galacto-non-2-enonate S3.[19] To a stirred solution of compound S2 (20 g, 64.7 mmol, 1 equiv.) in MeOH (600 mL) was added TfOH (4.95 mL, 64.7 mmol, 1 equiv.). The reaction mixture was allowed to stir at 60° C. for 16 h. The solvent was removed by rotary evaporation under reduced pressure and co-evaporated with toluene twice to remove traces of water. The obtained residue was dissolved in AcCl (200 mL) at 0° C. in a round bottom flask, sealed and stirred to room temperature for 2 days. Upon removal of solvent, the obtained residue was diluted with anhydrous acetonitrile (200 mL) and then Na$_2$HPO$_4$ (19.6 g, 155 mmol, 2.4 equiv.) was added under argon. The reaction mixture was vigorously stirred at 90° C. until TLC indicated the disappearance of starting material (16 hrs). The solution was filtered through a pad of Celite, dried over MgSO$_4$, and concentrated in vacuo. The obtained residue was purified by silica gel column chromatography using EtOAc/hexane (4:1) as eluent to give compound S3 as a brown foam (28.2 g, 92%). Spectroscopic data was agreed with reported in the literature previously.[19] R$_f$=0.30 (silica gel, EtOAc); $^1$H NMR (600 MHz, CDCl$_3$): δ 5.95 (d, J=3.0 Hz, 1H), 5.81 (d, J=9.0 Hz, 1H), 5.47-5.44 (m, 2H), 5.32-5.30 (m, 1H), 4.59 (dd, J=12.0, 3.0 Hz, 1H), 4.38-4.33 (m, 2H), 4.15 (d, J=12.0, 7.2 Hz, 1H), 3.76 (s, 3H, —CH$_3$), 2.08 (s, 3H, —CH$_3$), 2.03 (s, 3H, —CH$_3$), 2.02 (s, 3H, —CH$_3$), 2.01 (s, 3H, —CH$_3$), 1.88 (s, 3H, —CH$_3$); $^{13}$C NMR (150 MHz, CDCl$_3$): δ 170.7, 170.5, 170.1, 170.1, 170.0, 161.6, 145.0, 107.9, 70.6, 67.8, 67.6, 61.9, 52.5, 46.5, 23.1, 20.8, 20.7, 20.7; HRMS (ESI-TOF) m/e: Calcd for C$_{20}$H$_{27}$NO$_{12}$Na [M+Na]$^+$: 496.1425 found 496.1435.

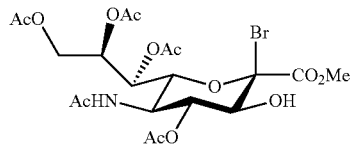

Methyl 5-acetamido-4,7,8,9-tetra-O-acetyl-2-bromo-2,5-dideoxy-D-erythro-α-L-gluco-non-2-ulopyranosonate 3.[20] The synthesis of the epoxide S4 was performed from sialic acid using reported procedures.[21] To a stirred solution of epoxide compound S4 (1.10 g, 2.25 mmol, 1 equiv.) in anhydrous 1,2-dichloroethane (18 mL), was added TiBr$_4$ (0.91 g, 2.47 mmol, 1.1 equiv.) under argon for 10 min. The solvent was removed by rotary evaporon under high vacuum. The obtained residue was diluted with EtOAc (30 mL), washed with saturated aq. Na$_2$SO$_4$ (10 mL), 5% aq. NaHCO$_3$ (10 mL), and then brine (5 mL). The separated organic layer was dried over MgSO$_4$, and concentrated in vacuo and the obtained residue was purified by silica gel column chromatography using acetone/hexane (2:1) as eluent to give compound 3 as a white powder (1.18 g, 92%). Spectroscopic data and protocol were identical to that reported previously.[20] R$_f$=0.23 (silica gel, acetone:toluene=1:1); $^1$H NMR (600 MHz, CDCl$_3$): δ 5.99 (d, J=7.2 Hz, 1H), 5.42 (dd, J=7.2, 1.2 Hz, 1H), 5.21-5.18 (m, 1H), 5.10 (ddd, J=6.0, 6.0, 2.4 Hz, 1H), 4.38 (dd, J=12.6, 2.4 Hz, 1H), 4.32-4.30 (m, 2H), 3.99 (dd, J=12.6, 6.0 Hz, 1H), 3.86 (s, 3H, —CH$_3$), 3.78 (d, J=9.0 Hz, 1H), 3.66 (br, 1H, —OH), 2.07 (s, 3H, —CH$_3$), 2.06 (s, 3H, —CH$_3$), 2.05 (s, 3H, —CH$_3$), 2.01 (s, 3H, —CH$_3$), 1.84 (s, 3H, —CH$_3$); $^{13}$C NMR (150 MHz, CDCl$_3$): δ 171.4, 170.6, 170.3, 169.8, 169.7, 167.0, 98.0, 75.0, 72.8, 72.2, 69.9, 66.5, 61.9, 54.0, 47.2, 22.9, 21.0, 20.7, 20.6; HRMS (ESI-TOF) m/e: Calcd for C$_{20}$H$_{29}$BrNO$_{13}$ [M+H]$^+$: 570.0817 found 570.0822.

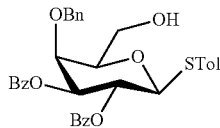

p-Tolyl 2,3-di-O-benzoyl-4-O-benzyl-1-thio-β-D-galactopyranoside 5.[22] To a stirred solution of starting material S523 (4.00 g, 6.86 mmol, 1 equiv.) in BH$_3$-THF complex (1 M in THF, 34.3 mL, 34.3 mmol, 5 equiv.) was added Cu(OTf)$_2$ (124 mg, 0.34 mmol, 0.05 equiv.) and the reaction mixture was stirred at room temperature for 8 h. Upon completion, the reaction was carefully neutralized with TEA (0.96 mL, 6.86 mmol, 1 equiv.) at 0° C., then diluted with MeOH (15 mL). After removal of solvent in vacuo, the obtained residue was purified by silica gel column chromatography using EtOAc/hexane (1:2) as an eluent to give compound 5 as a white powder (3.85 g, 96%). Spectroscopic data agreed with those reported in the literature previously.[22] R$_f$=0.45 (silica gel, EtOAc:hexane=1:1); $^1$H NMR (600 MHz, CDCl$_3$): δ 7.97-7.94 (m, 4H, Ar—H), 7.51-7.48 (m, 2H, Ar—H), 7.38-7.34 (m, 6H, Ar—H), 7.27-7.21 (m, 5H, Ar—H), 5.85 (dd, J=10.2, 10.2 Hz, 1H), 5.36 (dd, J=9.6, 3.0 Hz, 1H), 4.87 (d, J=9.6 Hz, 1H, C1-H$_β$), 4.74 (d, J=12.0 Hz, 1H), 4.47 (d, J=12.0 Hz, 1H), 4.16 (d, J=2.4 Hz, 1H), 3.91 (d, J=11.4, 7.2 Hz, 1H), 3.76 (dd, J=6.0, 6.0 Hz, 1H), 3.61 (dd, J=11.4, 5.4 Hz, 1H), 2.30 (s, 3H, —CH$_3$), 1.83 (br, 1H); $^{13}$C NMR (150 MHz, CDCl$_3$): δ 165.9, 165.2, 138.1, 137.4, 133.4, 133.1, 133.0, 129.8, 129.7, 129.6, 129.5, 128.9, 128.7, 128.5, 128.4, 128.3, 128.1, 127.9, 86.8, 79.0, 76.0, 74.6, 73.7, 68.5, 61.9, 21.1; HRMS (ESI-TOF) m/e: Calcd for C$_{34}$H$_{32}$O$_7$SNa [M+Na]$^+$: 607.1761 found 607.1770.

Scheme S2

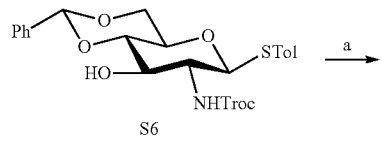

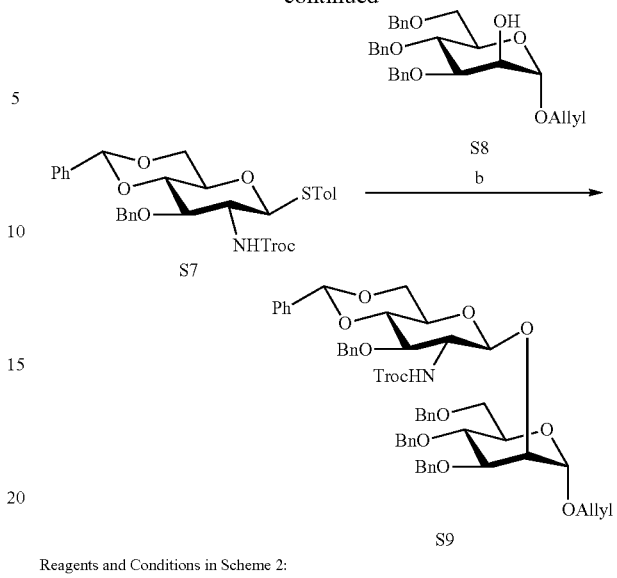

Reagents and Conditions in Scheme 2:
(a) TESOTf, BnCHO, TESH, toluene, THF, 2 h, -20° C., 90%.
(b) NIS, TfOH, 4 Å MS, -40° C., 1.5 h, CH$_2$Cl$_2$, 75%.
(c) NaBH$_3$CN, HCl/ether, AW-300 THF, 0° C. to r.t., 16 h, 85%.

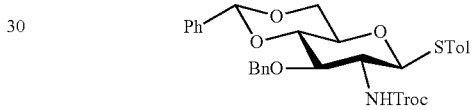

p-Tolyl 3-O-benzyl-4,6-O-benzylidene-2-deoxy-1-thio-2-(2,2,2-trichloroethoxy) carbamoylamino-β-D-glucopyranoside S7. To a stirred solution of starting material S6[24] (5.17 g, 9.42 mmol, 1 equiv.) in a mixture of THF/toluene (45 mL, 1:2=v/v) was added TESOTf (4.26 mL, 18.8 mmol, 2 equiv.) at -20° C. under argon. After stirring for 45 min at -20° C., benzaldehyde (4.79 mL, 47.1 mmol, 5 equiv.) and triethylsilane (2.26 mL, 14.1 mmol, 1.5 equiv.) were added dropwise to the mixture with stirring. After 2 h at -20° C., TLC indicated the disappearance of starting material and the reaction was quenched with satd. aq. Na$_2$CO$_3$, diluted with EtOAc (100 mL) and washed with satd. aq. Na$_2$CO$_3$ (30 mL), and brine. The combined organic layers were dried over MgSO$_4$, filtered and concentrated in vacuo. The resulting residue was purified by silica gel column chromatography first using CH$_2$Cl$_2$/toluene (1:4) then EtOAc/toluene (1:10) as eluent to give compound S7 as a white solid (5.40 g, 90%). R$_f$=0.50 (silica gel, EtOAc:toluene=1:25); $^1$H NMR (600 MHz, Acetone-d6): δ 7.52-7.50 (m, 2H, Ar—H), 7.42-7.36 (m, 4H, Ar—H), 7.32-7.31 (m, 2H, Ar—H), 7.29-7.22 (m, 4H, Ar—H), 7.18-7.15 (m, 2H, Ar—H), 5.72 (s, 1H, Ph-CH), 5.03 (d, J=10.8 Hz, 1H, C1-H$_β$), 4.90-4.82 (m, 3H), 4.74 (d, J=12.0 Hz, 1H), 4.30 (dd, J=10.2, 5.4 Hz, 1H), 3.95 (dd, J=9.6, 9.0 Hz, 1H), 3.84-3.71 (m, 3H), 3.56 (ddd, J=9.6, 9.6, 4.8 Hz, 1H), 2.83 (s, 2H), 2.32 (s, 3H, —CH$_3$); $^{13}$C NMR (150 MHz, Acetone-d6): δ 155.3, 139.8, 139.4, 138.6, 133.3, 130.7, 130.5, 129.8, 129.6, 129.1, 129.0, 129.0, 128.5, 128.2, 127.1, 101.8, 97.1, 88.6, 82.7, 80.8, 75.0, 75.0, 71.2, 69.1, 57.4, 21.1; HRMS (ESI-TOF) m/e: Calcd for C$_{30}$H$_{30}$Cl$_3$NO$_6$SNa [M+Na]$^+$: 660.0752 found 660.0749.

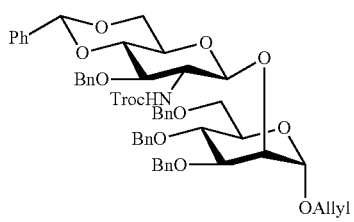

Allyl [3-O-benzyl-4,6-O-benzylidene-2-deoxy-2-(2,2,2-trichloroethoxy)carbonylamino-β-D-glucopyranosyl]-(1→2)-3,4,6-tri-O-benzyl-α-D-mannopyranoside S9. A mixture of acceptor S8[25] (523 mg, 0.94 mmol, 1 equiv.), donor S7 (900 mg, 1.41 mmol, 1.5 equiv.) and activated pulverized 4 Å MS (2.00 g) in anhydrous $CH_2Cl_2$ (20 mL) was stirred under argon for 1 h. Then, the reaction mixture was cooled to −40° C. and treated with NIS (423 mg, 1.88 mmol, 2 equiv.) and TfOH (0.5 M in $Et_2O$, 0.47 mL, 0.23 mmol, 0.25 equiv.). After stirring at that temperature for 1.5 h, the TLC analysis indicated disappearance of starting materials and the reaction mixture was quenched with $Et_3N$ (0.2 mL), and filtered through a pad of Celite. The filtrate was diluted with $CH_2Cl_2$ (20 mL), washed with 20% aq. $Na_2S_2O_3$ (5 mL), satd. aq. $NaHCO_3$ (10 mL) and brine (5 mL). The separated organic layer was dried over $MgSO_4$ and concentrated in vacuo. The obtained residue was purified by silica gel column chromatography using EtOAc/toluene (1:10) as eluent to give compound S9 as a white foam (710 mg, 75%). $R_f$=0.36 (silica gel, EtOAc:toluene=1:10); $^1H$ NMR (600 MHz, $CDCl_3$): δ 7.50-7.48 (m, 2H, Ar—H), 7.39-7.36 (m, 6H, Ar—H), 7.33-7.25 (m, 15H, Ar—H), 7.23-7.22 (m, 2H, Ar—H), 5.84 (ddd, J=16.2, 10.8, 5.4 Hz, 1H), 5.55 (s, 1H, Ph-CH), 5.26 (d, J=1.2 Hz, 1H), 5.23-5.20 (m, 1H), 5.16 (dd, J=10.8, 1.2 Hz, 1H), 5.01 (d, J=7.8 Hz, 1H, C1-H$_β$), 4.90 (d, J=10.8 Hz, 1H), 4.83 (d, J=11.4 Hz, 1H), 4.75-4.62 (m, 6H, C1-H$_α$), 4.55-4.51 (m, 3H), 4.33-4.29 (m, 2H), 4.13-4.10 (m, 1H), 4.08 (dd, J=2.4, 2.4 Hz, 1H), 4.00-3.97 (m, 1H), 3.94 (dd, J=9.6, 3.0 Hz, 1H), 3.89 (dd, J=13.2, 6.0 Hz, 1H), 3.82-3.78 (m, 2H), 3.72-3.66 (m, 3H), 3.50-3.46 (m, 1H), 3.12 (d, J=6.0 Hz, 1H); $^{13}C$ NMR (150 MHz, $CDCl_3$): δ 153.8, 138.6, 138.5, 138.3, 138.1, 137.3, 133.7, 129.0, 128.4, 128.3, 128.2, 128.1, 128.0, 127.8, 127.6, 127.6, 127.4, 126.0, 117.2, 101.2, 98.9, 96.9, 95.5, 82.4, 78.5, 75.6, 75.2, 74.6, 74.4, 74.2, 73.3, 72.2, 72.2, 69.2, 68.6, 68.0, 66.1, 58.1; HRMS (ESI-TOF) m/e: Calcd for $C_{53}H_{56}Cl_3NO_{12}Na$ [M+Na]$^+$: 1026.2760 found 1026.2780.

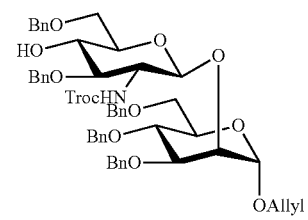

Allyl [3,6-di-O-benzyl-2-deoxy-2-(2,2,2-trichloroethoxy)carbonylamino-8-D-glucopyranosyl]-(1→2)-3,4,6-tri-O-benzyl-α-D-mannopyranoside 8.27 To a stirred solution of starting material S9 (500 mg, 0.50 mmol, 1 equiv.) in anhydrous THF (12 mL) was added activated pulverized AW 300 MS (1.20 g) under argon. Then, the reaction mixture was cooled to 0° C. and $NaCNBH_3$ (313 mg, 4.97 mmol, 10 equiv.) was added, followed by a slow addition of $HCl·Et_2O$ (2 M in $Et_2O$, 2.24 mL, 4.48 mmol, 9 equiv.), and the mixture was continued to stir until TLC indicated the disappearance of starting materials (16 hrs). Upon completion, the reaction mixture was quenched with satd. aq. $NaHCO_3$ (0.5 mL) and filtered through a pad of Celite. The filtrate was diluted with $CH_2Cl_2$ (20 mL) then washed with satd. aq. $NaHCO_3$ (8 mL) and brine (5 mL). The separated organic layer was dried over $MgSO_4$ and concentrated. The obtained residue was purified by silica gel column chromatography using EtOAc/toluene (1:5) as an eluent to give compound 8 as a white foam (425 mg, 85%). The spectroscopic data were consistent with those reported in the literature.[27] $R_f$=0.17 (silica gel, EtOAc:toluene=1:10); $^1H$ NMR (600 MHz, $CDCl_3$): δ 7.36-7.23 (m, 23H, Ar—H), 7.20-7.19 (m, 2H, Ar—H), 5.84 (ddd, J=16.2, 10.2, 6.0 Hz, 1H), 5.35 (br, 1H), 5.21 (dd, J=16.2, 1.2 Hz, 1H), 5.14 (dd, J=10.2, 1.2 Hz, 1H), 4.95 (d, J=7.2 Hz, 1H, C1-H$_β$), 4.88 (d, J=10.8 Hz, 1H), 4.78 (d, J=1.8 Hz, 1H, C1-H$_α$), 4.75 (d, J=11.4 Hz, 1H), 4.70-4.63 (m, 5H), 4.60 (d, J=11.4 Hz, 1H), 4.55-4.49 (m, 4H), 4.14-4.07 (m, 3H), 3.96-3.87 (m, 3H), 3.77 (dd, J=10.8, 4.2 Hz, 1H), 3.73-3.70 (m, 3H), 3.66 (dd, J=10.8, 1.8 Hz, 1H), 3.61 (dd, J=9.6, 8.4 Hz, 1H), 3.54-3.51 (m, 1H), 3.08 (m, 1H), 2.71 (m, 1H, —OH); $^{13}C$ NMR (150 MHz, $CDCl_3$): δ 154.0, 138.5, 138.5, 138.4, 138.1, 137.6, 133.7, 128.5, 128.5, 128.3, 128.3, 128.3, 128.2, 128.0, 128.0, 127.8, 127.7, 127.7, 127.6, 127.6, 127.5, 117.3, 79.2, 78.2, 75.1, 74.6, 74.3, 74.2, 73.8, 73.7, 73.4, 73.3, 72.0, 71.7, 70.9, 69.3, 68.0, 57.5; HRMS (ESI-TOF) m/e: Calcd for $C_{53}H_{58}Cl_3NO_{12}Na$ [M+Na]$^+$: 1028.2917 found 1028.2927.

Scheme S3

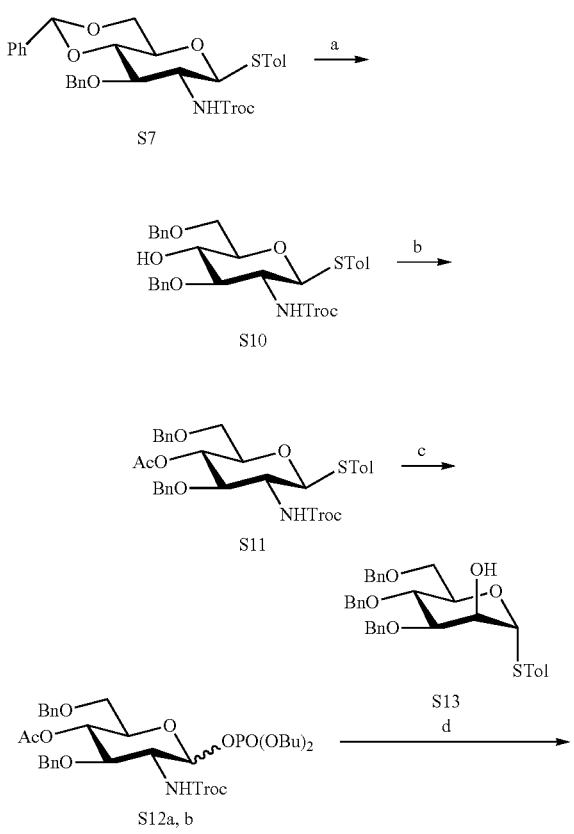

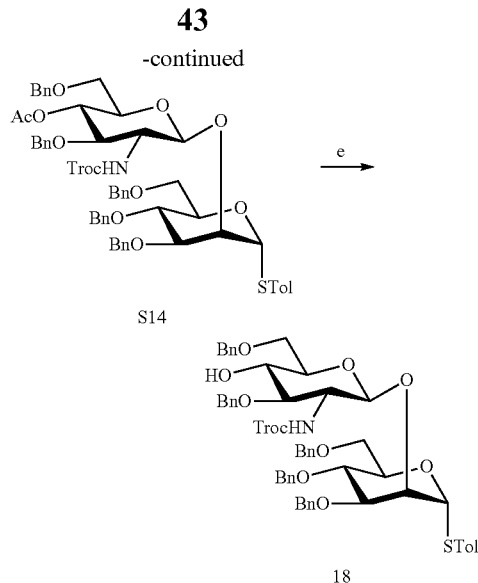

S14

18

Reagents and conditions in Scheme S3: (a) NaBH₃CN, HCl/ether, AW-300, THF, 0° C. to r.t., 16 h, 90%. (b) Ac₂O, pyridine, r.t., 16 h, 98%. (c) NIS, TfOH, HOPO(OBu)₂, 4Å MS, -30° C., 2 h, CH₂Cl₂, 90%. (d) TMSOTf, 4Å MS, -50° C., 1 h, CH₂Cl₂, 87%. (e) NaOMe, MeOH/CH₂Cl₂, 0° C. to r.t., 76%.

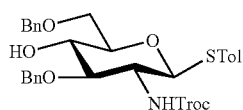

p-Tolyl 3,6-di-O-benzyl-2-deoxy-1-thio-2-(2,2,2-trichloroethoxy)carbamoylamino-β-D-glucopyranoside S10.[28] To a stirred solution of starting material S7 (1.00 g, 1.56 mmol, 1 equiv.) in anhydrous THF (30 mL) was added activated pulverized AW 300 MS (3.00 g) under argon. Then, the reaction mixture was cooled to 0° C. and NaCNBH₃ (0.98 g, 15.6 mmol, 10 equiv.) was added, followed by a slow addition of HCl·Et₂O (2 M in Et₂O, 7.04 mL, 14.1 mmol, 9 equiv.), and the mixture was stirred until TLC indicated the disappearance of starting materials (16 h). Upon completion, the reaction mixture was quenched with satd. aq. NaHCO₃ (0.5 mL) and filtered through a pad of Celite. The filtrate was diluted with CH₂Cl₂ (50 mL) then washed with satd. aq. NaHCO₃ (15 mL) and brine (10 mL). The separated organic layer was dried over MgSO₄ and concentrated. The obtained residue was purified by silica gel column chromatography using EtOAc/hexane/CH₂Cl₂ (1:3:1) as eluent to give compound S10 as a white foam (902 mg, 90%). The spectroscopic data were consistent with those reported in the literature.[28] $R_f$=0.29 (silica gel, EtOAc:hexane=1:3); ¹H NMR (600 MHz, CDCl₃): δ 7.40-7.38 (m, 2H, Ar—H), 7.36-7.27 (m, 10H, Ar—H), 7.04-7.03 (m, 2H, Ar—H), 5.20 (d, J=7.8 Hz, 1H), 4.84 (d, J=10.2 Hz, 1H, C1-H$_β$), 4.77-4.72 (m, 4H), 4.58-4.52 (m, 2H), 3.76 (d, J=4.8 Hz, 2H), 3.71-3.64 (m, 2H), 3.50-3.49 (m, 1H), 3.42-3.38 (m, 1H), 2.90 (br, 1H, —OH), 2.29 (s, 3H, —CH₃); ¹³C NMR (150 MHz, CDCl₃): δ 153.8, 138.1, 138.1, 137.7, 133.0, 129.6, 128.6, 128.5, 128.4, 128.1, 127.9, 127.8, 127.7, 95.5, 86.1, 81.9, 78.0, 74.5, 74.4, 73.6, 72.5, 70.4, 55.9, 21.1; HRMS (ESI-TOF) m/e: Calcd for C₃₀H₃₂Cl₃NO₆SNa [M+Na]⁺: 662.0908 found 662.0919.

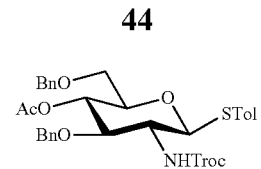

p-Tolyl 4-O-acetyl-3,6-di-O-benzyl-2-deoxy-1-thio-2-(2,2,2-trichloroethoxy)carbamoylamino-β-D-glucopyranoside S11. To a stirring solution of starting material S10 (0.97 g, 1.51 mmol, 1 equiv.) in pyridine (12 mL) was added Ac₂O (6 mL). The reaction mixture was vigorously stirred for 16 h at room temperature, then concentrated in vacuo and purified by silica gel column chromatography using EtOAc/hexane/CH₂Cl₂ (1:4:1) as eluent to give compound S11 as a white powder (1.01 g, 98%). $R_f$=0.47 (silica gel, EtOAc:hexane=1:3); ¹H NMR (600 MHz, CDCl₃): δ 7.41-7.40 (m, 2H, Ar—H), 7.34-7.25 (m, 8H, Ar—H), 7.22-7.21 (m, 2H, Ar—H), 7.03-7.01 (m, 2H, Ar—H), 5.29 (d, J=7.2 Hz, 1H), 5.04 (d, J=10.2 Hz, 1H, C1-H$_β$), 4.98 (dd, J=9.6, 9.6 Hz, 1H), 4.78 (d, J=12.0 Hz, 1H), 4.70 (d, J=12.0 Hz, 1H), 4.62 (d, J=11.4 Hz, 1H), 4.57 (d, J=11.4 Hz, 1H), 4.50 (br, 2H), 4.05 (dd, J=9.6, 9.0 Hz, 1H), 3.65-3.63 (m, 1H), 3.59-3.55 (m, 2H), 3.33 (ddd, J=9.6, 9.6, 9.6 Hz, 1H), 2.29 (s, 3H, —CH₃), 1.87 (s, 3H, —CH₃); ¹³C NMR (150 MHz, CDCl₃): δ 169.8, 153.7, 138.4, 138.0, 137.7, 133.3, 129.8, 128.6, 128.5, 128.4, 128.2, 128.1, 128.1, 127.9, 127.9, 127.7, 95.5, 85.3, 79.4, 77.7, 74.4, 73.6, 71.4, 69.7, 56.5, 21.1, 20.9; HRMS (ESI-TOF) m/e: Calcd for C₃₂H₃₄Cl₃NO₇SNa [M+Na]⁺: 704.1014 found 104.1031.

Dibutyl 4-O-acetyl-3,6-di-O-benzyl-2-deoxy-1-thio-2-(2,2,2-trichloroethoxy) carbamoylamino-α or β-D-glucopyranoside phosphate S12a, b. A mixture of compound S11 (990 mg, 1.45 mmol, 1 eq.), dibutyl phosphate (1.15 mL, 5.80 mmol, 3 eq.) and activated pulverized 4 Å MS (1.80 g) in anhydrous CH₂Cl₂ (18 mL) was stirred under argon for 1 h. Then it was cooled to -30° C. with stirring, and NIS (978 mg, 4.35 mmol, 2 eq.) was added followed by TfOH (0.5 M in Et₂O, 0.87 mL, 0.43 mmol, 0.3 eq.). After 2 h, the TLC analysis indicated disappearance of starting materials and the reaction mixture was quenched by satd. aq. NaHCO₃ (0.5 mL) and filtered through a pad of Celite. The filtrate was diluted with CH₂Cl₂ (50 mL), washed with 20% aq. Na₂S₂O₃ (10 mL), satd. aq. NaHCO₃ (5 mL) and brine (5 mL). The separated organic layer was dried over MgSO₄ and concentrated in vacuo. The obtained residue was purified by silica gel column chromatography using EtOAc/toluene (1:3) as eluent to give compound S12 as a white foam (1.00 g, 90%); anomeric mixture (α:β=1:3). β-anomer S12b: $R_f$=0.32 (silica gel, EtOAc:toluene=1:3); ¹H NMR (600 MHz, CDCl₃): δ 7.30-7.22 (m, 10H, Ar—H), 5.81 (br, 1H), 5.35 (dd, J=7.8, 7.8 Hz, 1H, C1-H$_β$), 5.09 (dd, J=9.6, 9.0 Hz, 1H), 4.74 (d, J=12.0 Hz, 1H), 4.65-4.58 (m, 3H), 4.49-4.44 (m, 2H), 4.06-3.97 (m, 4H), 3.88 (dd, J=9.6, 9.0 Hz, 1H), 3.77-3.74 (m, 1H), 3.69 (ddd, J=9.6, 4.2, 4.2 Hz, 1H), 3.53-3.52 (m, 2H), 1.83 (s, 3H, —CH₃), 1.61-1.54 (m, 4H), 1.36-1.31 (m, 4H), 0.93-0.85 (m, 6H); ¹³C NMR (150 MHz, CDCl₃): δ 169.5, 154.2, 137.6, 137.6, 128.5, 128.4, 128.3, 127.9, 127.9, 127.7, 127.7, 96.5, 95.3, 78.3, 74.5, 73.9, 73.6, 73.5, 70.6, 69.2, 68.1, 68.1, 68.1, 68.0, 57.2, 57.2, 32.1, 32.0, 32.0, 20.7, 18.6, 18.6, 13.5; HRMS (ESI-TOF) m/e: Calcd for $C_{33}H_{45}Cl_3NO_{11}PNa$ [M+Na]$^+$: 790.1688 found 790.1685. α-anomer S12a: $R_f$=0.44 (silica gel, EtOAc:toluene=1:3); $^1$H NMR (600 MHz, CDCl$_3$): δ 7.31-7.22 (m, 10H, Ar—H), 5.67 (dd, J=6.0, 3.6 Hz, 1H, C1-H$_\alpha$), 5.21-5.16 (m, 2H), 4.75 (d, J=12.0 Hz, 1H), 4.62-4.56 (m, 3H), 4.49-4.44 (m, 2H), 4.11-3.99 (m, 6H), 3.77 (dd, J=10.2, 9.6 Hz, 1H), 3.50-3.49 (m, 2H), 1.89 (s, 3H, —CH$_3$), 1.60-1.55 (m, 4H), 1.35-1.31 (m, 4H), 0.92-0.86 (m, 6H); $^{13}$C NMR (150 MHz, CDCl$_3$): δ 169.3, 154.0, 137.4, 137.4, 128.4, 128.2, 127.8, 127.8, 127.8, 127.6, 127.6, 127.6, 96.4, 96.3, 95.2, 76.4, 74.6, 73.6, 73.5, 71.1, 70.1, 68.6, 68.1, 68.0, 68.0, 67.9, 54.4, 54.3, 32.1, 32.0, 20.7, 18.5, 18.5, 13.5; HRMS (ESI-TOF) m/e: Calcd for $C_{33}H_{45}Cl_3NO_{11}PNa$ [M+Na]$^+$: 790.1688 found 790.1688.

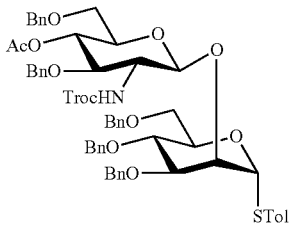

p-Tolyl [4-O-acetyl-3,6-di-O-benzyl-2-deoxy-2-(2,2,2-trichloroethoxy)carbonylamino-β-D-glucopyranosyl]-(1→2)-3,4,6-tri-O-benzyl-1-thio-α-D-mannopyranoside S14. A mixture of acceptor S1329 (407 mg, 0.73 mmol, 1 equiv.) and donor S12 (900 mg, 1.17 mmol, 1.6 equiv.) and activated pulverized 4 Å molecular sieves (200 mg) in anhydrous CH$_2$Cl$_2$ (2 mL) was stirred under argon for 30 min. Then it was cooled to –50° C. followed by addition of TMSOTf (0.21 mL, 1.17 μmol, 1.6 equiv. with respect to acceptor) with stirring until TLC analysis indicated disappearance of starting materials (1 h). The reaction mixture was quenched with Et$_3$N (0.30 mL), diluted with CH$_2$Cl$_2$ (20 mL), and filtered through a pad of Celite. The filtrate was washed twice with satd aq. NaHCO$_3$ (8 mL) and brine (4 mL). The organic phase was dried over MgSO$_4$, filtered, and concentrated in vacuo. The obtained residue was purified by silica gel column chromatography using EtOAc/hexane (1:3) as eluent to give compound S14 as a white powder (710 mg, 87%). $R_f$=0.26 (silica gel, EtOAc:hexane=1:3); $^1$H NMR (600 MHz, CDCl$_3$): δ 7.37-7.36 (m, 2H, Ar—H), 7.33-7.14 (m, 25H, Ar—H), 7.05-7.03 (m, 2H, Ar—H), 5.33 (d, J=1.8 Hz, 1H, C1-H$_\alpha$), 5.26 (d, J=4.8 Hz, 1H), 5.07 (d, J=9.0 Hz, 1H, C1-H$_\beta$), 4.93-4.90 (m, 2H), 4.77 (d, J=11.4 Hz, 1H), 4.60-4.52 (m, 5H), 4.46-4.34 (m, 5H), 4.27 (dd, J=8.4, 8.4 Hz, 1H), 4.19 (dd, J=9.6, 2.4 Hz, 1H), 4.15 (d, J=12.0 Hz, 1H), 4.07 (dd, J=9.6, 9.0 Hz, 1H), 3.84-3.81 (m, 2H), 3.64-3.63 (m, 2H), 3.57 (dd, J=10.8, 6.0 Hz, 1H), 3.51 (dd, J=11.4, 3.0 Hz, 1H), 3.01 (dd, J=6.6 Hz, 1H), 2.28 (s, 3H, —CH$_3$), 1.82 (s, 3H, —CH$_3$); $^{13}$C NMR (150 MHz, CDCl$_3$): δ 169.7, 154.2, 138.5, 138.3, 138.0, 137.8, 137.7, 137.6, 132.5, 130.3, 129.8, 129.7, 129.0, 128.4, 128.4, 128.3, 128.2, 128.2, 128.2, 128.2, 127.9, 127.8, 127.8, 127.7, 127.7, 127.6, 127.6, 127.6, 127.4, 125.2, 97.1, 95.4, 86.2, 78.3, 75.2, 75.1, 74.5, 74.1, 74.0, 73.6, 73.4, 73.1, 72.5, 71.7, 71.3, 70.0, 69.2, 58.1, 21.1, 20.8; HRMS (ESI-TOF) m/e: Calcd for $C_{59}H_{62}Cl_3NO_{12}SNa$ [M+Na]$^+$: 1136.2950 found 1136.2978.

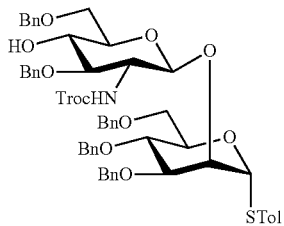

p-Tolyl [3,6-di-O-benzyl-2-deoxy-2-(2,2,2-trichloroethoxy)carbonylamino-β-D-glucopyranosyl]-(1→2)-3,4,6-tri-O-benzyl-1-thio-α-D-mannopyranoside 18. To a well-stirred solution of compound S14 (203 mg, 0.18 mmol, 1 equiv.) in a mixture of CH$_2$Cl$_2$/MeOH (10 mL, 1:1=v/v) was added NaOMe (2.95 mg, 0.055 mmol, 0.3 equiv.) at 0° C. After 20 min, the ice bath was removed and the reaction mixture was warmed up to room temperature with stirring until TLC analysis indicated the disappearance of starting materials (4 hrs). Upon completion, the reaction mixture was neutralized with IR-120, filtered, and concentrated in vacuo. The obtained residue was purified by silica gel column chromatography using EtOAc/hexane (1:2) as eluent to give compound 18 as a white foam (149 mg, 76%). $R_f$=0.14 (silica gel, EtOAc:hexane=1:3); $^1$H NMR (600 MHz, CDCl$_3$): δ 7.39-7.37 (m, 2H, Ar—H), 7.34-7.24 (m, 25H, Ar—H), 7.06-7.05 (m, 2H, Ar—H), 5.33 (d, J=1.8 Hz, 1H, C1-H$_\alpha$), 5.24 (d, J=4.8 Hz, 1H), 5.00 (d, J=7.8 Hz, 1H, C1-H$_\beta$), 4.93 (d, J=10.8 Hz, 1H), 4.78 (d, J=11.4 Hz, 1H), 4.69-4.64 (m, 2H), 4.61 (d, J=11.4 Hz, 2H), 4.57-4.51 (m, 4H), 4.43 (d, J=11.4 Hz, 1H), 4.34 (dd, J=2.4, 2.4 Hz, 1H), 4.22-4.20 (m, 2H), 4.07-4.04 (m, 2H), 3.84-3.82 (m, 2H), 3.77-3.72 (m, 2H), 3.67-3.65 (m, 1H), 3.59-3.54 (m, 2H), 3.01 (d, J=7.2 Hz, 1H), 2.68 (br, 1H, —OH), 2.30 (s, 3H, —CH$_3$); $^{13}$C NMR (150 MHz, CDCl$_3$): δ 154.2, 138.5, 138.4, 138.3, 137.9, 137.7, 137.6, 132.5, 130.3, 129.8, 128.5, 128.5, 128.4, 128.3, 128.1, 128.0, 127.9, 127.8, 127.8, 127.7, 127.6, 127.6, 127.5, 97.5, 95.4, 86.2, 79.1, 78.4, 75.3, 75.2, 74.6, 74.4, 74.2, 73.8, 73.8, 73.2, 73.1, 72.5, 71.4, 70.9, 69.3, 57.8, 21.1; HRMS (ESI-TOF) m/e: Calcd for $C_{57}H_{60}Cl_3NO_{11}SNa$ [M+Na]$^+$: 1094.2845 found 1094.2881.

Scheme S4

1st Route

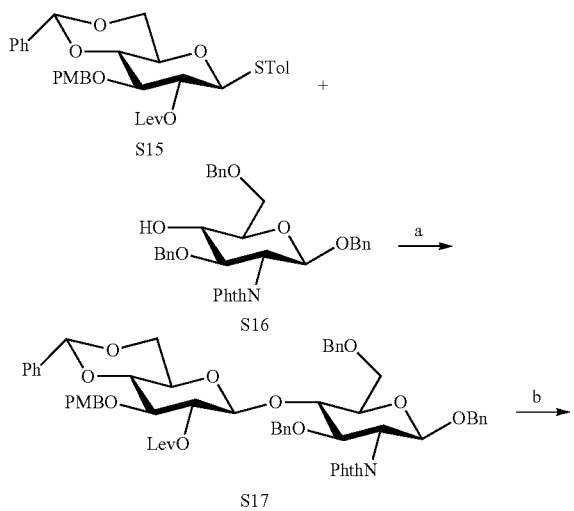

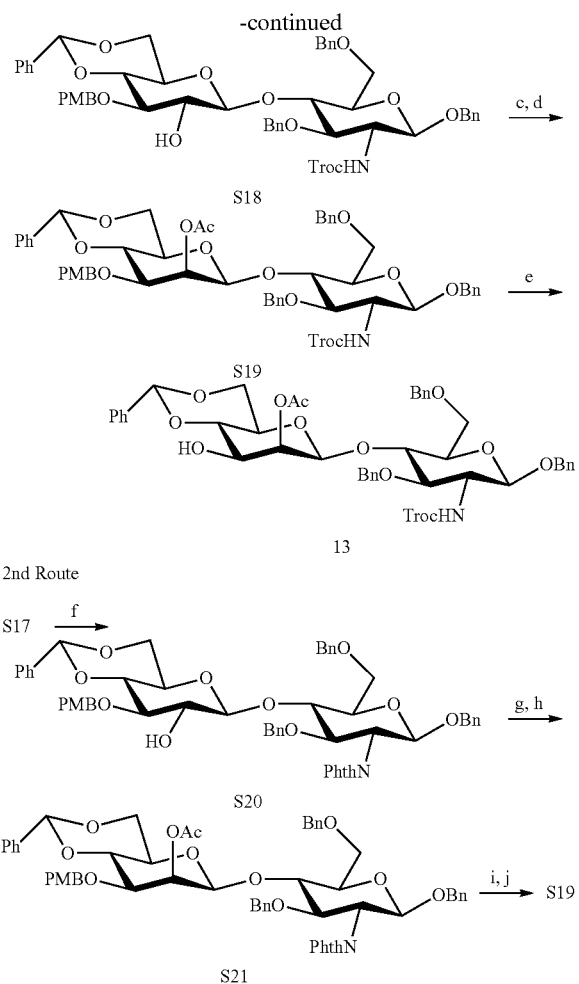

2nd Route

Reagents and conditions in Scheme S4: (a) NIS, TfOH, 4 Å MS, -40° C., 1 h, CH₂Cl₂, 93%. (b) ethylenediamine/BuOH (1:4), 90° C., 2 h, then NaHCO₃, TrocCl, CH₂Cl₂, 0° C., 3 h, 81%. (c) Tf₂O, pyridine, CH₂Cl₂, 0° C., 4 h. (d) Bu₄NOAc, toluene, sonication, r.t., 8 h, then NaHCO₃, TrocCl, CH₂Cl₂, 0° C., 3 h, 61% (2 steps). (e) DDQ, CH₂Cl₂, phosphate buffer (pH = 7), 0° C. to r.t., 3 h, 85%. (f) hydrazine acetate, THF, r.t., 16 h, 92%. (g) Tf₂O, pyridine, CH₂Cl₂, 0° C., 2 h. (h) Bu₄NOAc, toluene, sonication, r.t., 8 h, 93% (2 steps). (i) ethylenediamine/BuOH (1:4), 90° C., 2 h, then NaHCO₃, TrocCl, CH₂Cl₂, 0° C., 3 h. (j) Ac₂O, pyridine, CH₂Cl₂, r.t., 16 h, 83% (2 steps).

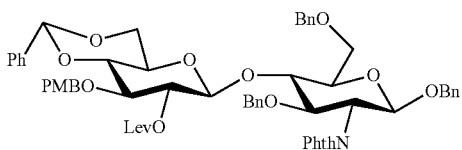

Benzyl [4,6-O-benzylidine-3-O-p-methoxy-benzyl-2-O-levulinoyl-β-D-glucopyranosyl]-(1→4)-3,6-di-O-benzyl-2-deoxy-2-phthalimido-β-D-glucopyranoside S17. A mixture of acceptor S16.[30] A mixture of acceptor S16[30] (1.59 g, 2.74 mmol, 1 equiv.), donor S15[26] (2.11 g, 3.57 mmol, 1.3 equiv.) and activated pulverized 4 Å MS (5.00 g) in anhydrous CH₂Cl₂ (50 mL) was stirred under argon for 1 h. Then, the reaction mixture was cooled to −40° C. and NIS (1.23 g, 0.49 mmol, 2 equiv.) was added, followed by TfOH (0.5 M in Et₂O, 1.37 mL, 0.69 mmol, 0.25 equiv.). The reaction was continued until TLC indicated the disappearance of starting materials (2 h). Upon completion, the reaction mixture was quenched with Et₃N (0.7 mL) and filtered through a pad of Celite. The filtrate was diluted with CH₂Cl₂ (50 mL), washed with 20% aq. Na₂S₂O₃ (15 mL), satd. aq. NaHCO₃ (20 mL), and brine (10 mL). The separated organic layer was dried over MgSO₄ and concentrated in vacuo. The obtained residue was purified by silica gel column chromatography using EtOAc/hexane (2:3) as eluent to give compound S17 as a white foam (2.68 g, 93%). $R_f$=0.43 (silica gel, acetone: toluene=1:6); ¹H NMR (600 MHz, CDCl₃): δ 7.75 (br, 1H, Ar—H), 7.63 (br, 2H, Ar—H), 7.50 (br, 1H, Ar—H), 7.46-7.45 (m, 2H, Ar—H), 7.39-7.32 (m, 7H, Ar—H), 7.29-7.26 (m, 1H, Ar—H), 7.20-7.18 (m, 2H, Ar—H), 7.07-7.05 (m, 1H, Ar—H), 7.02-7.01 (m, 4H, Ar—H), 6.98-6.97 (m, 2H, Ar—H), 6.87-6.83 (m, 5H, Ar—H), 5.44 (s, 1H, Ph-CH), 5.10-5.08 (m, 1H, C1-H$_\beta$), 4.92 (dd, J=9.0, 8.4 Hz, 1H), 4.81-4.71 (m, 4H), 4.58 (d, J=7.8 Hz, 1H, C1-H$_\beta$), 4.56 (d, J=4.2 Hz, 1H), 4.47 (d, J=6.0 Hz, 1H), 4.45 (d, J=6.6 Hz, 1H), 4.36 (d, J=12.6 Hz, 1H), 4.23 (dd, J=10.2, 4.8 Hz, 1H), 4.20-4.19 (m, 2H), 4.09-4.06 (m, 1H), 3.87 (dd, J=11.4, 3.0 Hz, 1H), 3.79-3.78 (m, 1H), 3.78 (s, 3H, —CH₃), 3.59 (dd, J=9.6, 9.0 Hz, 1H), 3.55-3.51 (m, 2H), 3.43 (dd, J=10.2, 10.2 Hz, 1H), 3.17 (ddd, J=9.6, 9.6, 4.8 Hz, 1H), 2.81-2.76 (m, 1H), 2.70-2.65 (m, 1H), 2.50-2.38 (m, 2H), 2.20 (s, 3H, —CH₃); ¹³C NMR (150 MHz, CDCl₃): δ 206.2, 171.1, 159.2, 138.6, 138.1, 137.3, 133.5, 131.6, 130.4, 129.4, 129.0, 128.5, 128.2, 128.1, 127.9, 127.8, 127.7, 127.5, 127.5, 127.0, 126.0, 123.1, 113.6, 101.1, 100.6, 97.4, 81.7, 78.0, 77.9, 76.6, 74.8, 74.5, 73.7, 73.6, 70.7, 68.6, 67.7, 65.8, 55.7, 55.3, 37.7, 29.9, 27.8; HRMS (ESI-TOF) m/e: Calcd for C₆₁H₆₁NO₁₅Na [M+Na]⁺: 1070.3933 found 1070.3933.

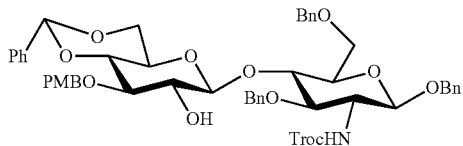

Benzyl [4,6-O-benzylidine-3-O-p-methoxy-benzyl-6-D-glucopyranosyl]-(1→4)-3,6-di-O-benzyl-2-deoxy-2-(2,2,2-trichloroethoxy)carbonylamino-β-D-glucopyranoside S18. A solution of disaccharide S17 (625 mg, 0.596 mmol, 1 equiv.) in ethylene diamine/n-BuOH (7 mL, 2:8=v/v) was stirred at 90° C. for 2 h. The solvent was removed by rotary evaporation under high vacuum and co-evaporated with toluene twice to remove traces of water. The obtained residue was dissolved in anhydrous CH₂Cl₂ (15 mL) and treated with NaHCO₃ (250 mg, 2.98 mmol, 5 equiv.) and 2,2,2-trichloro ethyl chloroformate (0.41 mL, 2.98 mmol, 5 equiv.) at 0° C. under argon for 3 h. Upon completion, the reaction mixture was diluted with CH₂Cl₂ (20 mL), washed with water (20 mL) and brine (10 mL). The organic layer was dried over MgSO₄ and concentrated in vacuo. The obtained residue was purified by silica gel column chromatography using EtOAc/toluene (1:4) as eluent to give compound S18 as a white powder (481 mg, 81%). $R_f$=0.60 (silica gel, EtOAc:toluene=1:2); ¹H NMR (600 MHz, CDCl₃): δ 7.47-7.46 (m, 2H, Ar—H), 7.40-7.25 (m, 20H, Ar—H), 6.86-6.85 (m, 2H, Ar—H), 5.46 (s, 1H, Ph-CH), 5.12 (br, 1H), 4.88-4.85 (m, 3H), 4.71-4.55 (m, 9H, 2C1-H$_\beta$), 4.06-4.03 (m, 2H), 3.99 (dd, J=11.4, 3.6 Hz, 1H), 3.87 (br, 1H), 3.80 (dd, J=11.4, 1.8 Hz, 1H), 3.78 (s, 3H, —CH₃), 3.56 (dd, J=9.6, 9.0 Hz, 1H), 3.52-3.45 (m, 5H), 3.15 (ddd, J=9.6, 9.6, 4.8 Hz, 1H), 3.03 (br, 1H, —OH); ¹³C NMR (150 MHz, CDCl₃): δ 159.3, 153.8, 138.4, 137.7, 137.3, 137.2, 130.4, 129.6, 128.9, 128.4, 128.4, 128.3, 128.2, 128.0, 127.8, 127.8, 127.6, 127.4, 126.0, 113.8, 103.2, 101.1, 99.2, 95.5, 81.3, 79.9, 79.2, 77.7, 74.9, 74.5, 74.3, 74.2, 73.5, 70.7, 68.6, 68.2, 66.2, 57.6, 55.2; HRMS (ESI-TOF) m/e: Calcd for $C_{51}H_{54}Cl_3NO_{13}Na$ [M+Na]$^+$: 1016.2553 found 1016.2554.

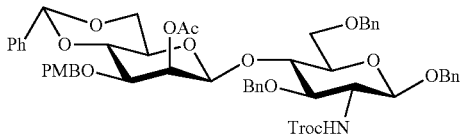

Benzyl [2-O-acetyl-4,6-O-benzylidine-3-O-p-methoxybenzyl-β-D-mannopyranosyl]-(1→4)-3,6-di-O-benzyl-2-deoxy-2-(2,2,2-trichloroethoxy)carbonylamino-β-D-glucopyranoside S19. From S18: To a stirred solution of disaccharide S18 (1.02 g, 1.02 mmol, 1 equiv.) in anhydrous $CH_2Cl_2$ (13 mL) was added anhydrous pyridine (0.58 mL, 7.17 mmol, 7 equiv.), followed by dropwise addition of $Tf_2O$ (0.30 mL, 1.79 mmol, 1.75 equiv.) at 0° C. under argon. The reaction mixture was stirred at 0° C. until TLC indicated the disappearance of starting material (4 hrs). Upon completion, it was diluted with $CH_2Cl_2$ (20 mL), washed with 0.5N HCl (20 mL) and brine (10 mL). The separated organic layer was dried over $MgSO_4$ and concentrated in vacuo. The crude residue was mixed with $Bu_4NOAc$ (927 mg, 3.07 mmol, 3 equiv.) and dissolved in toluene (20 mL). The solvent was removed in vacuo and the residue was co-evaporated with toluene twice; then, redissolved in anhydrous toluene (13 mL) and the mixture was sonicated for 8 h. During this time, we observed a partial deprotection of NHTroc and the reaction mixture was concentrated under high vacuum. The obtained residue was dissolved in $CH_2Cl_2$ (13 mL) and treated with $NaHCO_3$ (430 mg, 5.12 mmol, 5 equiv.) and 2,2,2-trichloro ethyl chloroformate (0.71 mL, 5.12 mmol, 5 equiv.) at 0° C. under argon. After stirring for 3 h, the reaction mixture was diluted with $CH_2Cl_2$ (20 mL), washed with water (20 mL) and brine (10 mL). The separated organic layer was dried over $MgSO_4$ and concentrated in vacuo. The obtained residue was purified by silica gel column chromatography using EtOAc/toluene (1:5) as eluent to give compound S19 as a white powder (650 mg, 61%).

From S21: A solution of disaccharide S21 (1.20 g, 1.21 mmol, 1 equiv.) in ethylene diamine/n-BuOH (15 mL, 2:8=v/v) was stirred at 90° C. for 2 h. After removal of solvent, the crude product was co-evaporated with toluene twice. The obtained residue was dissolved in $CH_2Cl_2$ (30 mL) and treated with $NaHCO_3$ (508 mg, 6.05 mmol, 5 equiv.) and 2,2,2-trichloro ethyl chloroformate (0.83 mL, 6.05 mmol, 5 equiv.) at 0° C. under argon. After 3 h, the reaction mixture was diluted with $CH_2Cl_2$ (45 mL), washed with water (30 mL) and brine (15 mL). The organic layer was dried over $MgSO_4$, concentrated, co-evaporated with toluene twice, and evaporated in vacuo. The obtained residue was subjected directly to the acetylation conditions $Ac_2O$ (7 mL) in pyridine (14 mL), with the temperature slowly warmed up from 0° C. to room temperature in 16 h. The reaction mixture was concentrated under high vacuum and purified by silica gel column chromatography using acetone/toluene (1:5) as eluent to give compound S19 as a white powder (1.04 g, 83%). $R_f$=0.54 (silica gel, EtOAc:toluene=1:3); $^1H$ NMR (600 MHz, CDCl$_3$): δ 7.48-7.46 (m, 2H, Ar—H), 7.39-7.35 (m, 3H, Ar—H), 7.33-7.25 (m, 14H, Ar—H), 7.24-7.21 (m, 3H, Ar—H), 6.84-6.82 (m, 2H, Ar—H), 5.50 (s, 1H, Ph-CH), 5.41 (d, J=3.0 Hz, 1H), 5.09 (br, 1H), 4.92 (d, J=10.8 Hz, 1H), 4.88 (d, J=12.0 Hz, 1H), 4.72-4.62 (m, 5H, 2C1-H$_β$), 4.58-4.56 (m, 3H), 4.47-4.44 (m, 2H), 4.08 (dd, J=10.2, 4.8 Hz, 1H), 4.04 (dd, J=9.0, 8.4 Hz, 1H), 3.87-3.84 (m, 2H), 3.78-3.72 (m, 5H, —CH$_3$), 3.59 (dd, J=10.2, 10.2 Hz, 1H), 3.45-3.43 (m, 1H), 3.38 (ddd, J=8.4, 8.4, 8.4 Hz, 1H), 3.10 (ddd, J=9.6, 9.6, 4.8 Hz, 1H), 2.07 (s, 3H, —CH$_3$); $^{13}C$ NMR (150 MHz, CDCl$_3$): δ 170.3, 159.3, 153.8, 138.4, 137.8, 137.4, 137.1, 129.7, 129.2, 128.9, 128.5, 128.4, 128.3, 128.2, 128.0, 128.0, 127.9, 127.8, 127.7, 126.1, 113.8, 101.4, 99.1, 99.1, 77.8, 75.3, 74.4, 73.5, 71.4, 70.8, 69.1, 68.5, 68.4, 67.0, 57.5, 55.2, 21.0; HRMS (ESI-TOF) m/e: Calcd for $C_{53}H_{56}Cl_3NO_{14}Na$ [M+Na]$^+$: 1058.2658 found 1058.2657.

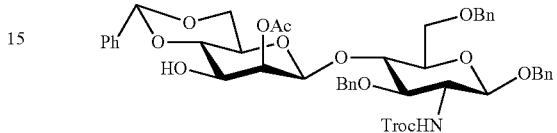

Benzyl [2-O-acetyl-4,6-O-benzylidine-β-D-mannopyranosyl]-(1→4)-3,6-di-O-benzyl-2-deoxy-2-(2,2,2-trichloroethoxy)carbonylamino-β-D-glucopyranoside 13. To a stirring solution of S19 (120 mg, 0.12 mmol, 1 equiv.) in a mixture of $CH_2Cl_2$/phosphate buffer (pH=7) (3 mL, 9:1=v/v) was added 2,3-dichloro-5,6-dicyanobenzoquinone (52.5 mg, 0.23 mmol, 2.2 equiv.) at 0° C. The reaction mixture was vigorously stirred until TLC indicated the disappearance of starting material (3 hrs). Upon completion, the reaction mixture was diluted with $CH_2Cl_2$ (10 mL), washed with satd. aq. $NaHCO_3$ (8 mL) and brine (4 mL), and the organic phase was dried over $MgSO_4$, filtered and concentrated. The obtained residue was purified by silica gel column chromatography using EtOAc/toluene (1:4) as eluent to give compound 13 as a white powder (90 mg, 85%). $R_f$=0.29 (silica gel, EtOAc:toluene=1:3); $^1H$ NMR (600 MHz, CDCl$_3$): δ 7.45-7.44 (m, 2H, Ar—H), 7.39-7.34 (m, 7H, Ar—H), 7.33-7.26 (m, 11H, Ar—H), 5.47 (s, 1H, Ph-CH), 5.23 (d, J=3.6 Hz, 1H), 5.06 (br, 1H), 4.91 (d, J=11.4 Hz, 1H), 4.87 (d, J=12.0 Hz, 1H), 4.74 (d, J=12.0 Hz, 1H), 4.68-4.61 (m, 4H, 2C1-H$_β$), 4.58-4.56 (m, 2H), 4.48 (d, J=12.0 Hz, 1H), 4.08 (dd, J=10.2, 4.8 Hz, 1H), 4.04 (dd, J=9.0, 9.0 Hz, 1H), 3.83 (br, 1H), 3.78 (dd, J=11.4, 3.0 Hz, 1H), 3.73-3.70 (m, 2H), 3.64 (dd, J=9.6, 3.6 Hz, 1H), 3.56 (dd, J=10.2, 10.2 Hz, 1H), 3.43-3.36 (m, 2H), 3.11 (ddd, J=9.6, 9.6, 4.8 Hz, 1H), 2.21 (d, J=3.6 Hz, 1H), 2.11 (s, 3H, —CH$_3$); $^{13}C$ NMR (150 MHz, CDCl$_3$): δ 170.5, 153.8, 138.5, 137.8, 137.1, 137.0, 129.3, 128.6, 128.6, 128.4, 128.4, 128.3, 128.1, 128.0, 128.0, 127.9, 127.8, 127.7, 126.2, 102.1, 99.1, 99.0, 78.5, 78.2, 74.4, 74.4, 73.6, 71.2, 70.8, 69.7, 68.4, 68.4, 66.7, 57.5; HRMS (ESI-TOF) m/e: Calcd for $C_{45}H_{49}Cl_3NO_{13}$ [M+H]$^+$: 916.2264 found 916.2252.

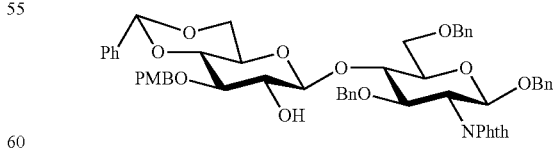

Benzyl [4,6-O-benzylidine-3-O-p-methoxy-benzyl-β-D-glucopyranosyl]-(1→4)-3,6-di-O-benzyl-2-deoxy-2-phthalimido-β-D-glucopyranoside S20. To a stirring solution of starting material S17 (2.48 g, 2.37 mmol, 1 equiv.) in anhydrous THF (55 mL) was added hydrazine acetate (327 mg, 3.55 mmol, 1.5 equiv.) at room temperature under argon. The reaction mixture was vigorously stirred until TLC indicated the disappearance of starting material (16 hrs). Upon completion, the reaction mixture was diluted with EtOAc (150 mL), washed with water (60 mL) and brine (30 mL). The organic phase was dried over MgSO$_4$, filtered, and concentrated in vacuo. The obtained residue was purified by silica gel column chromatography using EtOAc/Hexane (1:2) as eluent to give compound S20 as a white foam (2.07 g, 92%). $R_f$=0.54 (silica gel, EtOAc:hexane=1:1); $^1$H NMR (600 MHz, CDCl$_3$): δ 7.79-7.54 (m, 4H, Ar—H), 7.51-7.44 (m, 2H, Ar—H), 7.38-7.33 (m, 7H, Ar—H), 7.30-7.27 (m, 3H, Ar—H), 7.08-7.04 (m, 1H, Ar—H), 7.02-7.01 (m, 4H, Ar—H), 6.98-6.97 (m, 2H, Ar—H), 6.89-6.81 (m, 5H, Ar—H), 5.46 (s, 1H, Ph-CH), 5.09 (d, J=8.4 Hz, 1H, C1-H$_β$), 4.85 (d, J=11.4 Hz, 1H), 4.77 (d, J=12.6 Hz, 1H), 4.75 (d, J=4.2 Hz, 1H), 4.73 (d, J=4.2 Hz, 1H), 4.68 (d, J=11.4 Hz, 1H), 4.62 (d, J=7.2 Hz, 1H, C1-H$_β$), 4.56 (d, J=12.0 Hz, 1H), 4.46 (d, J=12.0 Hz, 1H), 4.38 (d, J=12.0 Hz, 1H), 4.32 (dd, J=10.8, 8.4 Hz, 1H), 4.21 (d, J=10.8, 8.4 Hz, 1H), 4.15-4.10 (m, 2H), 4.04 (dd, J=11.4, 3.0 Hz, 1H), 3.82 (dd, J=11.4, 1.8 Hz, 1H), 3.78 (s, 3H, —CH$_3$), 3.61 (ddd, J=9.6, 3.0, 3.0 Hz, 1H), 3.56 (dd, J=3.0, 3.0 Hz, 1H), 3.52-3.45 (m, 3H), 3.18 (ddd, J=9.6, 9.6, 4.8 Hz, 1H), 2.98 (br, 1H, —OH); $^{13}$C NMR (150 MHz, CDCl$_3$): δ 167.9, 159.3, 138.4, 137.8, 137.3, 137.2, 133.6, 131.6, 130.5, 129.7, 128.9, 128.4, 128.2, 128.1, 128.0, 127.9, 127.8, 127.5, 127.4, 127.1, 126.0, 123.2, 113.8, 103.4, 101.1, 97.5, 81.3, 79.5, 78.8, 77.8, 75.0, 74.7, 74.5, 74.2, 73.6, 70.8, 68.6, 68.2, 66.2, 55.8, 55.3; HRMS (ESI-TOF) m/e: Calcd for C$_{56}$H$_{55}$NO$_{13}$Na [M+Na]$^+$: 972.3565 found 972.3567.

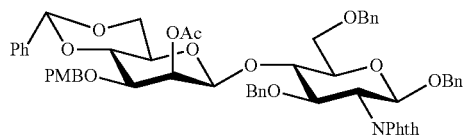

Benzyl [2-O-acetyl-4,6-O-benzylidine-3-O-p-methoxybenzyl-β-D-mannopyranosyl]-(1→4)-3,6-di-O-benzyl-2-deoxy-2-phthalimido-β-D-glucopyranoside S21. To a stirred solution of disaccharide S20 (936 mg, 0.985 mmol, 1 equiv.) in anhydrous CH$_2$Cl$_2$ (12 mL) was added anhydrous pyridine (0.56 mL, 6.90 mmol, 7 equiv.), then trifluoromethanesulfonic anhydride (0.29 mL, 1.72 mmol, 1.75 equiv.) was added dropwise at 0° C. under argon and the mixture was stirred at 0° C. until TLC indicated the disappearance of starting material (2 h). Upon completion, the reaction mixture was diluted with CH$_2$Cl$_2$ (20 mL), washed with 0.5 N HCl (20 mL) and brine (10 mL). The separated organic layer was dried over MgSO$_4$, concentrated in vacuo and the obtained residue was used as is for further reactions. The above-obtained residue was added Bu$_4$NOAc (594 mg, 1.97 mmol, 2 equiv.) and dissolved in toluene (18 mL). The solvent was removed in vacuo and the residue was co-evaporated with toluene twice to remove traces of water. The residue was redissolved in anhydrous toluene (12 mL) and the mixture was sonicated for 8 h. Upon completion, the reaction mixture was diluted with EtOAc (20 mL), washed with water (20 mL) and brine (10 mL). The separated organic layer was dried over MgSO$_4$ and concentrated. The obtained residue was purified by silica gel column chromatography using EtOAc/hexane (1:2) as eluent to give compound S21 as white powder (913 mg, 93%). $R_f$=0.29 (silica gel, EtOAc:hexane=1:2); $^1$H NMR (600 MHz, CDCl$_3$): δ 7.76-7.49 (m, 4H, Ar—H), 7.48-7.46 (m, 2H, Ar—H), 7.39-7.31 (m, 7H, Ar—H), 7.26-7.22 (m, 3H, Ar—H), 7.10-7.06 (m, 1H, Ar—H), 7.04-7.03 (m, 4H, Ar—H), 6.99-6.98 (m, 2H, Ar—H), 6.90-6.84 (m, 5H, Ar—H), 5.49 (s, 1H, Ph-CH), 5.44 (d, J=3.0 Hz, 1H), 5.09 (d, J=7.8 Hz, 1H, C1-H$_β$), 4.82-4.76 (m, 3H), 4.68 (s, 1H, C1-H$_β$), 4.58 (d, J=12.0 Hz, 1H), 4.49-4.44 (m, 3H), 4.38 (d, J=12.6 Hz, 1H), 4.26-4.19 (m, 2H), 4.17-4.11 (m, 2H), 3.86-3.82 (m, 2H), 3.78 (s, 3H, —CH$_3$), 3.78-3.76 (m, 1H), 3.57-3.54 (m, 2H), 3.44 (dd, J=10.2, 3.6 Hz, 1H), 3.13 (ddd, J=9.6, 9.6, 4.8 Hz, 1H), 2.15 (s, 3H, —CH$_3$); $^{13}$C NMR (150 MHz, CDCl$_3$): δ 170.2, 167.8, 159.2, 138.5, 137.8, 137.4, 137.1, 133.6, 131.5, 129.7, 129.2, 128.9, 128.5, 128.1, 128.1, 127.9, 127.9, 127.8, 127.7, 127.6, 127.5, 127.1, 126.0, 123.1, 113.8, 101.4, 99.5, 97.3, 79.1, 77.7, 76.9, 75.4, 74.5, 74.3, 73.5, 71.3, 70.7, 69.1, 68.4, 68.3, 66.9, 55.6, 55.2, 21.0; HRMS (ESI-TOF) m/e: Calcd for C$_{58}$H$_{57}$NO$_{14}$Na [M+Na]$^+$: 1014.3671 found 1014.3699.

Scheme S5

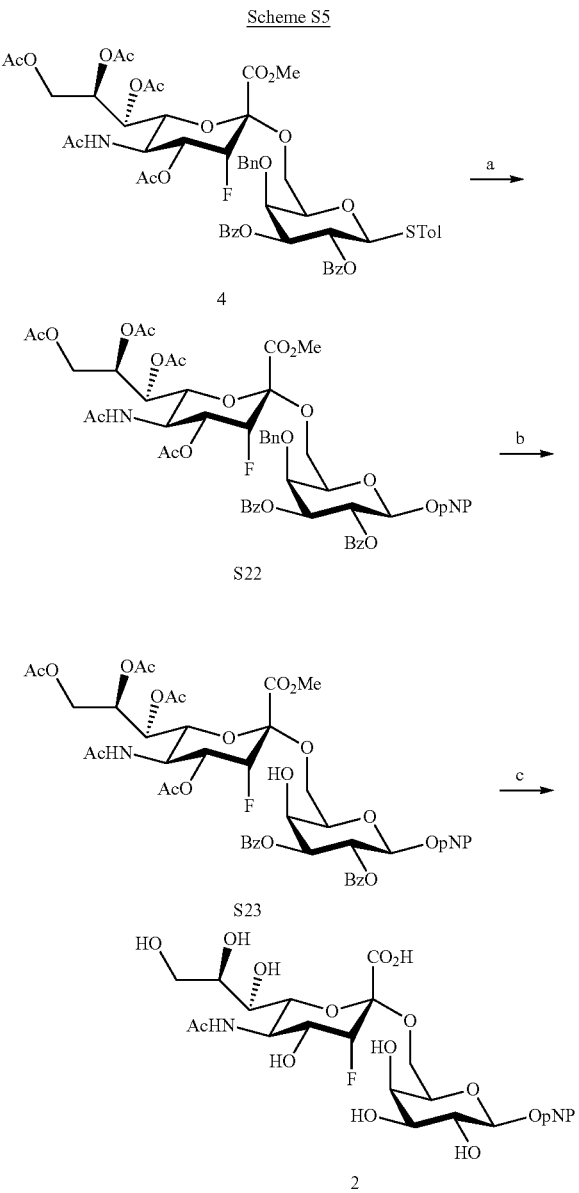

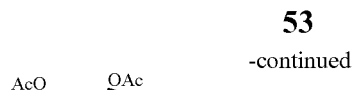
-continued

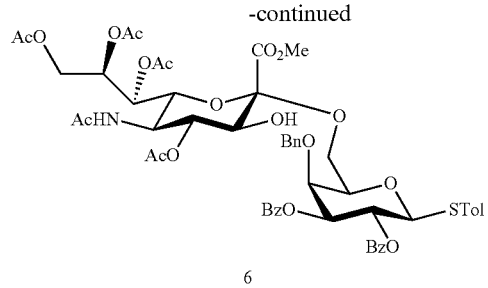

6

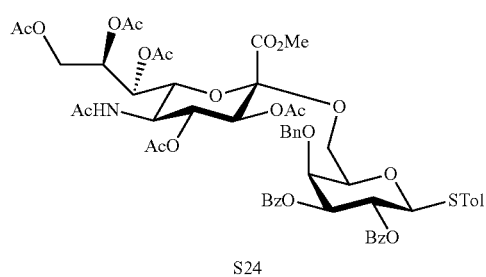

S24

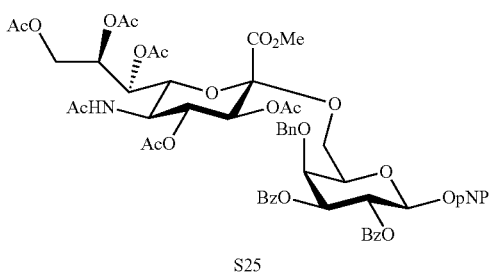

S25

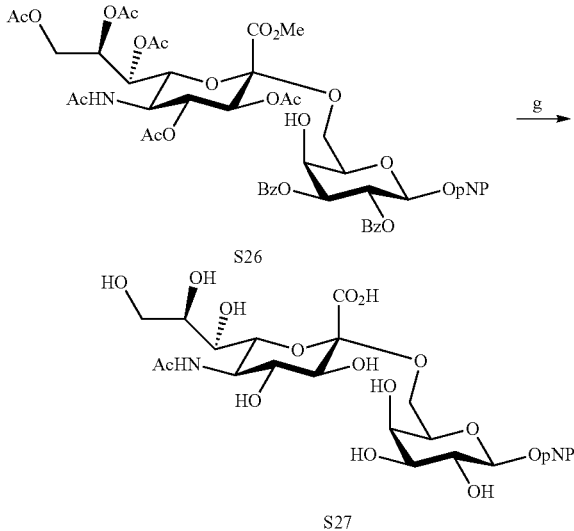

S26

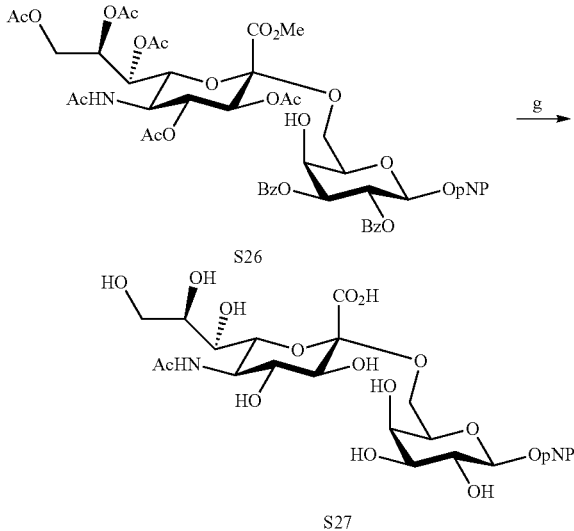

S27

Reagents and conditions in Scheme S5: (a) Br₂, CH₂Cl₂, 0° C., 10 min., then p-nitrophenol, Ag₂O, CH₃CN, 1 h, 73%. (b) NaBrO₃, Na₂S₂O₄, H₂O, EtOAc, r.t., 1.5 h, 93%. (c) LiOH·H₂O, MeOH, r.t., 16 h, 84%. (d) Ac₂O, pyridine, r.t., 16 h, 90%. (e) Br₂, CH₂Cl₂, 0° C., 10 min., then p-nitrophenol, Ag₂O, CH₃CN, 1 h, 74%. (f) NaBrO₃, Na₂S₂O₄, H₂O, EtOAc, r.t., 1.5 h, 97% (g) LiOH·H₂O, MeOH, r.t., 16 h, 94%.

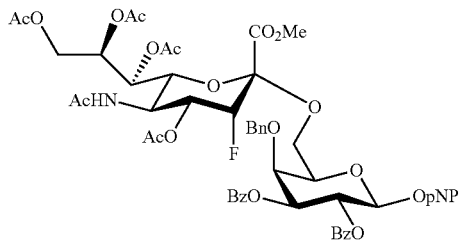

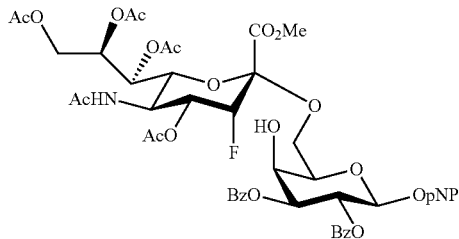

p-Nitrophenyl [methyl 5-acetamido-4,7,8,9-tetra-O-acetyl-3,5-dideoxy-3-fluoro-D-erythro-α-L-manno-non-2-ulopyranosonate]-(2→6)-2,3-di-O-benzoyl-4-O-benzyl-β-D-galactopyranoside S22. To a stirred solution of thioglycoside 4 (115 mg, 0.11 mmol, 1 equiv.) in anhydrous CH₂Cl₂ (2 mL) at 0° C. was added bromine (6.02 µL, 0.12 mmol, 1.1 equiv.). After the reaction mixture was vigorously stirred for 10 min, the solvent was removed in vacuo and the residue was co-evaporated with toluene twice to remove traces of water. Thus obtained residue was dissolved in anhydrous CH₃CN (2 mL) and treated with 4-nitrophenol (25.3 mg, 0.18 mmol, 1.7 equiv.) and Ag₂O (124 mg, 0.53 mmol, 5 equiv.). The reaction mixture was vigorously stirred in the dark under N₂ until TLC indicated the disappearance of starting material (1 h). Upon completion, the reaction mixture was diluted with EtOAc (10 mL) and filtered through a pad of Celite. The filtrate was washed twice with satd. aq. NaHCO₃ (4 mL) and brine (3 mL). The organic phase was dried over MgSO₄, filtered, and concentrated in vacuo. The obtained residue was purified by silica gel column chromatography using acetone/toluene (1:2) as eluent to give compound S22 as a white powder (85 mg, 73%). $R_f$=0.46 (silica gel, acetone:toluene=2:3); $^1$H NMR (600 MHz, CDCl₃): δ 8.13-8.11 (m, 2H, Ar—H), 7.96-7.94 (m, 2H, Ar—H), 7.91-7.89 (m, 2H, Ar—H), 7.49-7.44 (m, 2H, Ar—H), 7.35-7.30 (m, 6H, Ar—H), 7.24-7.22 (m, 2H, Ar—H), 7.20-7.18 (m, 2H, Ar—H), 7.13-7.11 (m, 1H, Ar—H), 6.09 (dd, J=10.2, 7.8 Hz, 1H), 5.65-5.59 (dd, J=10.2, 3.0 Hz, 1H, C1-H$_\beta$), 5.35 (d, J=9.6 Hz, 1H), 5.28 (dd, J=9.6, 1.8 Hz, 1H), 5.19 (dd, J=27.0, 10.8 Hz, 1H, sia-C4-H), 5.04 (dd, J=51.0, 1.8 Hz, 1H, sia-C3-H), 4.72-4.67 (m, 2H), 4.44 (dd, J=12.6, 3.6 Hz, 1H), 4.40 (d, J=3.0 Hz, 1H), 4.37 (dd, J=8.4, 6.6 Hz, 1H), 4.31 (d, J=10.8 Hz, 1H), 4.18 (ddd, J=4.2, 4.2, 4.2 Hz, 1H), 4.08 (dd, J=12.6, 6.6 Hz, 1H), 3.89-3.80 (m, 5H, —CH₃), 2.26 (s, 6H, -2CH₃), 2.10 (s, 3H, —CH₃), 1.93 (s, 3H, —CH₃), 1.92 (s, 3H, —CH₃); $^{13}$C NMR (150 MHz, CDCl₃): δ 171.1, 170.8, 170.4, 170.3, 170.2, 165.5, 165.5, 165.4, 165.3, 161.8, 142.6, 138.0, 133.2, 133.1, 129.8, 129.7, 129.4, 129.0, 128.4, 128.3, 128.2, 128.1, 128.0, 127.5, 125.6, 116.8, 98.8, 98.7, 98.2, 88.1, 86.8, 75.0, 73.9, 73.7, 73.2, 71.6, 69.7, 69.1, 69.0, 67.3, 67.2, 63.4, 63.3, 53.4, 45.1, 23.3, 21.2, 20.8, 20.7, 20.6; $^{19}$F NMR (376 MHz, CDCl₃): δ −215.5; HRMS (ESI-TOF) m/e: Calcd for $C_{53}H_{55}FN_2O_{22}Na$ [M+Na]⁺: 1113.3123 found 1113.3131.

p-Nitrophenyl [methyl 5-acetamido-4,7,8,9-tetra-O-acetyl-3,5-dideoxy-3-fluoro-D-erythro-α-L-manno-non-2-ulopyranosonate]-(2→6)-2,3-di-O-benzoyl-8-D-galactopyranoside S23. To a stirring solution of compound S22 (63.0 mg, 0.058 mmol, 1 equiv.) in EtOAc (0.8 mL) was added NaBrO$_3$ (85%, 39.2 mg, 0.26 mmol, 4.5 equiv.) in H$_2$O (0.6 mL) followed by a slow addition of Na$_2$S$_2$O$_4$ (40.2 mg, 0.23 mmol, 4 equiv.) in H$_2$O (1.2 mL) at room temperature. The reaction mixture was stirred until TLC indicated the disappearance of the starting material (1.5 h). Upon completion of the reaction, the reaction mixture was diluted with EtOAc (10 mL), washed with 20% aq. Na$_2$S$_2$O$_3$ (5 mL) and brine (3 mL). The organic phase was dried over MgSO$_4$, filtered, and concentrated in vacuo, and the obtained residue was purified by silica gel column chromatography using acetone/toluene (3:5) as eluent to give compound S23 as a white powder (54 mg, 93%). $R_f$=0.40 (silica gel, acetone:toluene=2:3); $^1$H NMR (600 MHz, CDCl$_3$): δ 8.13-8.12 (m, 1H, Ar—H), 7.99-7.98 (m, 2H, Ar—H), 7.95-7.94 (m, 2H, Ar—H), 7.50-7.46 (m, 2H, Ar—H), 7.37-7.32 (m, 4H, Ar—H), 7.19-7.18 (m, 2H, Ar—H), 6.05 (dd, J=10.2, 9.8 Hz, 1H), 5.53 (ddd, J=9.0, 6.0, 3.0 Hz, 1H), 5.49-5.45 (m, 2H, C1-H$_β$), 5.36 (d, J=9.0 Hz, 1H), 5.27 (dd, J=9.0, 1.8 Hz, 1H), 5.19 (dd, J=27.0, 11.4 Hz, 1H, sia-C4-H), 5.05 (dd, J=51.6, 1.8 Hz, 1H, sia-C3-H), 4.47 (d, J=3.0 Hz, 1H), 4.37 (dd, J=12.6, 3.0 Hz, 1H), 4.26 (dd, J=10.8, 1.2 Hz, 1H), 4.18 (dd, J=6.6, 6.6 Hz, 1H), 4.13-4.07 (m, 1H), 4.05 (dd, J=12.6, 6.6 Hz, 1H), 3.99-3.98 (m, 2H), 3.85 (s, 3H, —CH$_3$), 2.99 (br, 1H, —OH), 2.17 (s, 3H, —CH$_3$), 2.08 (s, 3H, —CH$_3$), 2.07 (s, 3H, —CH$_3$), 1.93 (s, 3H, —CH$_3$), 1.88 (s, 3H, —CH$_3$); $^{13}$C NMR (150 MHz, CDCl$_3$): δ 170.9, 170.8, 170.5, 170.3, 165.6, 165.6, 165.3, 161.8, 142.9, 133.4, 133.3, 129.8, 129.7, 129.2, 129.1, 129.0, 128.4, 128.4, 128.2, 125.6, 125.3, 117.1, 99.0, 98.1, 98.0, 88.3, 87.0, 73.9, 73.3, 71.6, 69.2, 69.1, 69.0, 67.9, 67.2, 66.5, 63.6, 62.9, 53.4, 45.1, 23.3, 21.1, 20.7, 20.6, 20.6; $^{19}$F NMR (376 MHz, CDCl$_3$): δ −216.0; HRMS (ESI-TOF) m/e: Calcd for C$_{46}$H$_{50}$FN$_2$O$_{22}$ [M+H]$^+$: 1001.2834 found 1001.2833.

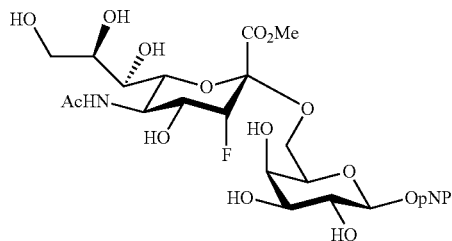

p-Nitrophenyl [methyl 5-acetamido-3,5-dideoxy-3-fluoro-D-erythro-α-L-manno-non-2-ulopyranosonate]-(2→6)-β-D-galactopyranoside 2. To a solution of compound S23 (53 mg, 0.053 mmol, 1 equiv.) in methanol (5 mL) was added LiOH·H$_2$O (22.2 mg, 0.53 mmol, 10 equiv.) in water (1 mL). After stirring for 16 h at room temperature, the reaction mixture was neutralized with IR-120, filtered, and concentrated in vacuo. The obtained residue was purified by (BIO-RAD) Biogel P-2 column chromatography (eluting with water) to give compound 2 (27 mg, 84%). $^1$H NMR (600 MHz, D$_2$O): δ 8.29-8.28 (m, 2H, Ar—H), 7.30-7.29 (m, 2H, Ar—H), 5.21 (dd, J=51.6, 2.4 Hz, 1H, sia-C3-H), 5.18 (d, J=7.8 Hz, 1H, C1-H$_β$), 4.17 (dd, J=9.0, 9.0 Hz, 1H), 4.07-4.00 (m, 3H), 3.91-3.77 (m, 7H), 3.63 (dd, J=12.0, 6.6 Hz, 1H), 3.57 (dd, J=9.0, 1.8 Hz, 1H), 2.04 (s, 3H, —CH$_3$); $^{13}$C NMR (150 MHz, D$_2$O): δ 175.0, 170.8, 161.9, 142.5, 126.1, 116.5, 100.0, 98.9, 98.9, 91.6, 90.3, 73.9, 72.4, 72.4, 71.6, 70.3, 69.7, 69.5, 68.4, 68.1, 63.7, 62.6, 46.8, 46.8, 22.0; $^{19}$F NMR (376 MHz, CDCl$_3$): δ −217.6; HRMS (ESI-TOF) m/e: Calcd for C$_{23}$H$_{32}$FN$_2$O$_{16}$ [M+H]$^+$: 611.1730 found 611.1732.

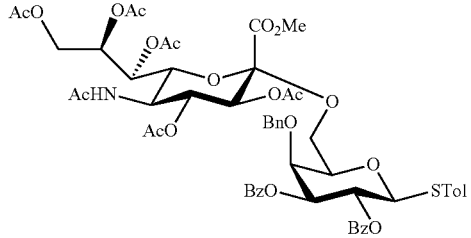

p-Tolyl [methyl 5-acetamido-3,4,7,8,9-penta-O-acetyl-5-deoxy-D-erythro-α-L-gluco-non-2-ulopyranosonate]-(2→6)-2,3-di-O-benzoyl-4-O-benzyl-1-thio-β-D-galactopyranoside S24. To a stirring solution of starting material 6 (174 mg, 0.16 mmol, 1 equiv.) in pyridine (2 mL) was added Ac$_2$O (1 mL). The reaction mixture was vigorously stirred for 16 h at room temperature, then concentrated under high vacuum. The obtained residue was purified by silica gel column chromatography using acetone/toluene (1:2) as eluent to give compound S24 as a white powder (162 mg, 90%). $R_f$=0.49 (silica gel, acetone:toluene=2:3); $^1$H NMR (600 MHz, CDCl$_3$): δ 7.94-7.92 (m, 2H, Ar—H), 7.88-7.87 (m, 2H, Ar—H), 7.48-7.44 (m, 2H, Ar—H), 7.40-7.38 (m, 2H, Ar—H), 7.35-7.27 (m, 6H, Ar—H), 7.23-7.20 (m, 2H, Ar—H), 7.18-7.16 (m, 1H, Ar—H), 7.05-7.03 (m, 2H, Ar—H), 5.80 (dd, J=10.2, 9.6 Hz, 1H), 5.44-5.42 (m, 2H), 5.35-5.29 (m, 3H), 5.25 (dd, J=8.4, 1.8 Hz, 1H), 4.95 (d, J=10.2 Hz, 1H, C1-H$_β$), 4.67-4.61 (m, 3H), 4.33 (ddd, J=10.2, 10.2, 10.2 Hz, 1H), 4.25-4.22 (m, 2H), 4.03-3.97 (m, 3H), 3.92-3.89 (m, 1H), 3.75 (s, 3H, —CH$_3$), 2.29 (s, 3H, —CH$_3$), 2.15 (s, 3H, —CH$_3$), 2.07 (s, 3H, —CH$_3$), 2.00 (s, 3H, —CH$_3$), 1.95 (s, 3H, —CH$_3$), 1.94 (s, 3H, —CH$_3$), 1.89 (s, 3H, —CH$_3$); $^{13}$C NMR (150 MHz, CDCl$_3$): δ 171.0, 170.5, 170.3, 170.0, 169.3, 168.5, 168.0, 165.7, 165.2, 138.4, 137.6, 133.1, 132.9, 132.5, 129.8, 129.7, 129.7, 129.5, 129.2, 129.1, 128.3, 128.2, 128.0, 127.4, 127.2, 98.9, 86.5, 76.9, 75.5, 74.6, 74.3, 72.7, 71.6, 71.5, 68.5, 68.3, 66.9, 62.6, 62.5, 52.7, 48.4, 23.0, 21.1, 20.8, 20.7, 20.6, 20.6, 20.5; HRMS (ESI-TOF) m/e: Calcd for C$_{56}$H$_{61}$NO$_{21}$SNa [M+Na]$^+$: 1138.3349 found 1138.3358.

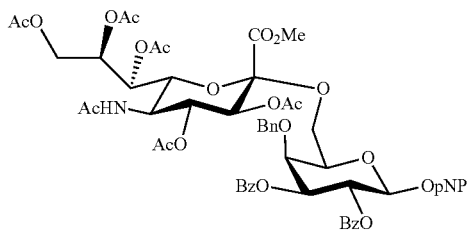

p-Nitrophenyl [methyl 5-acetamido-3,4,7,8,9-penta-O-acetyl-5-deoxy-D-erythro-α-L-gluco-non-2-ulopyranosonate]-(2→6)-2,3-di-O-benzoyl-4-O-benzyl-β-D-galactopyranoside S25. To a stirring solution of thioglycoside S24 (132 mg, 0.12 mmol, 1 equiv.) in anhydrous CH$_2$Cl$_2$ (2.5 mL) at 0° C. was added bromine (6.67 µL, 0.13 mmol, 1.1 equiv.). After vigorously stirring for 10 min, the solvent was removed in vacuo and the residue was co-evaporated with toluene twice to remove traces of water. The obtained residue was dissolved in anhydrous CH$_3$CN (2.5 mL) and treated with 4-nitrophenol (28.0 mg, 0.20 mmol, 1.7 equiv.) and Ag$_2$O (137 mg, 0.59 mmol, 5 equiv.). The reaction mixture was vigorously stirred in the dark under N$_2$ until TLC indicated the disappearance of starting material (1 h). Upon completion of the reaction, the reaction mixture was diluted with EtOAc (12 mL), and filtered through a pad of Celite. The filtrate was washed twice with satd. aq. NaHCO$_3$ (5 mL) and brine (3 mL). The organic phase was dried over MgSO$_4$, filtered, and concentrated in vacuo, and the obtained residue was purified by silica gel column chromatography using acetone/toluene (3:5) as eluent to give compound S25 as a white powder (99 mg, 74%). R$_f$=0.51 (silica gel, acetone:toluene=2:3); $^1$H NMR (600 MHz, CDCl$_3$): δ 8.15-8.13 (m, 2H, Ar—H), 7.95-7.92 (m, 4H, Ar—H), 7.50-7.44 (m, 2H, Ar—H), 7.36-7.31 (m, 6H, Ar—H), 7.24-7.19 (m, 2H, Ar—H), 7.17-7.15 (m, 3H, Ar—H), 6.10 (dd, J=10.2, 7.8 Hz, 1H), 5.54 (dd, J=10.2, 3.0 Hz, 1H), 5.52 (d, J=7.8 Hz, 1H, C1-H$_β$), 5.48 (ddd, J=10.2, 7.2, 3.0 Hz, 1H), 5.39 (d, J=10.2 Hz, 1H), 5.31-5.29 (m, 2H), 5.23 (dd, J=9.6, 1.8 Hz, 1H), 4.73 (dd, J=10.8, 2.4 Hz, 1H), 4.71-4.65 (m, 2H), 4.32-4.30 (m, 3H), 4.19 (dd, J=7.2, 7.2 Hz, 1H), 3.97 (dd, J=12.6, 7.2 Hz, 1H), 3.88-3.86 (m, 2H), 3.83 (s, 3H, —CH$_3$), 2.24 (s, 3H, —CH$_3$), 2.12 (s, 3H, —CH$_3$), 2.01 (s, 3H, —CH$_3$), 1.98 (s, 3H, —CH$_3$), 1.90 (s, 3H, —CH$_3$), 1.88 (s, 3H, —CH$_3$); $^{13}$C NMR (150 MHz, CDCl$_3$): δ 171.0, 170.7 (2C), 170.0, 169.6, 168.5, 168.3, 165.7, 165.3, 161.7, 142.7, 137.9, 133.3, 133.2, 129.9, 129.7, 129.3, 128.9, 128.4, 128.3, 128.2, 128.0, 127.6, 125.7, 116.8, 99.7, 98.4, 75.1, 74.1, 74.0, 73.9, 72.8, 71.6, 71.1, 69.7, 67.6, 67.0, 63.8, 63.3, 52.9, 48.4, 23.0, 20.9, 20.8, 20.7, 20.6; HRMS (ESI-TOF) m/e: Calcd for C$_{55}$H$_{59}$N$_2$O$_{24}$ [M+H]$^+$: 1131.3452 found 1131.3440.

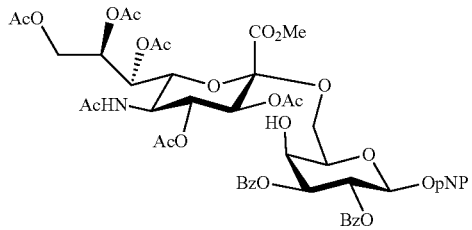

p-Nitrophenyl [methyl 5-acetamido-3,4,7,8,9-penta-O-acetyl-5-deoxy-D-erythro-α-L-gluco-non-2-ulopyranosonate]-(2→6)-2,3-di-O-benzoyl-8-D-galactopyranoside S26. To a stirring solution of compound S25 (91.0 mg, 0.080 mmol, 1 equiv.) in EtOAc (1.2 mL) was added NaBrO$_3$ (54.6 mg, 0.36 mmol, 4.5 equiv.) in H$_2$O (0.9 mL) followed by a slow addition of Na$_2$S$_2$O$_4$ (85%, 56.0 mg, 0.32 mmol, 4 equiv.) in H$_2$O (1.8 mL) at room temperature. The reaction mixture was stirred until TLC indicated the disappearance of the starting material (1.5 h). Upon completion, the reaction mixture was diluted with EtOAc (15 mL), washed with 20% aq. Na$_2$S$_2$O$_3$ (7 mL) and brine (4 mL). The organic phase was dried over MgSO$_4$, filtered, and concentrated in vacuo. The obtained residue was purified by silica gel column chromatography using acetone/toluene (3:5) as eluent to give compound S26 as a white powder (81 mg, 97%). R$_f$=0.23 (silica gel, acetone:toluene=2:3); $^1$H NMR (600 MHz, CDCl$_3$): δ 8.18-8.16 (m, 2H, Ar—H), 8.00-7.99 (m, 2H, Ar—H), 7.94-7.93 (m, 2H, Ar—H), 7.51-7.46 (m, 2H, Ar—H), 7.38-7.32 (m, 4H, Ar—H), 7.15-7.13 (m, 2H, Ar—H), 6.07 (dd, J=10.2, 7.8 Hz, 1H), 5.46-5.34 (m, 5H, C1-H$_β$), 5.30 (d, J=10.2 Hz, 1H), 5.22 (d, J=7.8, 1.8 Hz, 1H), 4.60 (dd, J=10.8, 1.8 Hz, 1H), 4.43 (d, J=3.0 Hz, 1H), 4.33 (dd, J=12.6, 2.4 Hz, 1H), 4.26 (ddd, J=10.2, 10.2, 10.2 Hz, 1H), 4.12 (dd, J=6.6, 6.6 Hz, 1H), 4.05 (dd, J=10.2, 6.6 Hz, 1H), 3.99 (dd, J=10.2, 6.6 Hz, 1H), 3.93 (dd, J=12.6, 7.2 Hz, 1H), 3.83 (s, 3H, —CH$_3$), 3.17 (br, 1H, —OH), 2.14 (s, 3H, —CH$_3$), 2.05 (s, 3H, —CH$_3$), 2.02 (s, 3H, —CH$_3$), 2.00 (s, 3H, —CH$_3$), 1.87 (s, 3H, —CH$_3$), 1.85 (s, 3H, —CH$_3$); $^{13}$C NMR (150 MHz, CDCl$_3$): δ 171.1, 171.0, 170.4, 170.0, 169.9, 168.8, 167.9, 165.8, 165.2, 161.7, 142.9, 133.4, 133.3, 129.9, 129.7, 129.3, 129.1, 128.4, 128.4, 125.8, 116.9, 99.1, 98.9, 74.0, 73.9, 73.0, 71.1, 70.6, 69.2, 68.7, 67.2, 66.5, 63.0, 62.5, 53.0, 48.5, 23.0, 20.8, 20.7, 20.6, 20.6; HRMS (ESI-TOF) m/e: Calcd for C$_{48}$H$_{53}$N$_2$O$_{24}$ [M+H]$^+$: 1041.2983 found 1041.2976.

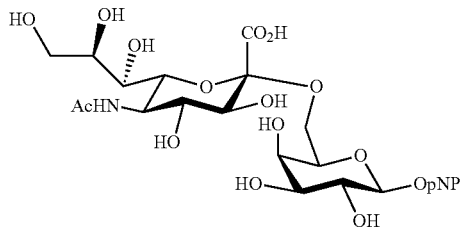

p-Nitrophenyl [5-acetamido-5-deoxy-D-erythro-α-L-gluco-non-2-ulopyranosonate]-(2→6)-β-D-galactopyranoside S27. To a solution of compound S26 (75 mg, 0.072 mmol, 1 equiv.) in methanol (5 mL) was added LiOH·H$_2$O (30 mg, 0.72 mmol, 10 equiv.) in water (1 mL). After stirring for 16 h at room temperature, the reaction mixture was neutralized with IR-120, filtered, and concentrated. The obtained residue was purified by (BIO-RAD) Biogel P-2 column chromatography using water as eluent to give compound S27 (41 mg, 94%). $^1$H NMR (600 MHz, D$_2$O): δ 8.29-8.28 (m, 2H, Ar—H), 7.28-7.27 (m, 2H, Ar—H), 5.20 (d, J=7.2 Hz, C1-H$_β$), 4.09-4.06 (m, 2H), 4.01 (dd, J=10.8, 7.8 Hz, 1H), 3.92-3.79 (m, 6H), 3.71 (d, J=10.8 Hz, 1H), 3.64-3.60 (m, 2H), 3.53 (d, J=9.6 Hz, 1H), 3.49 (d, J=9.6 Hz, 1H), 2.02 (s, 3H, —CH$_3$); $^{13}$C NMR (150 MHz, D$_2$O): δ 174.8, 173.0, 161.9, 142.5, 126.1, 116.4, 99.9, 98.1, 76.1, 73.9, 73.5, 72.4, 72.2, 71.5, 70.3, 68.4, 68.0, 63.0, 62.6, 50.7, 21.9; HRMS (ESI-TOF) m/e: Calcd for C$_{23}$H$_{33}$N$_2$O$_{17}$ [M+H]$^+$: 609.1774 found 609.1774.

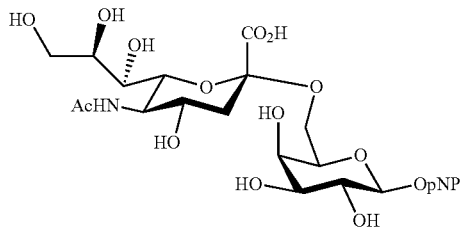

p-Nitrophenyl [5-acetamido-5-deoxy-D-glycero-α-D-galacto-non-2-ulopyranosylonate]-(2→6)-β-D-galactopyranoside 1. Neu5Ac-α2,6-Gal-pNP: Neu5Ac-α2,6-Gal-pNP was synthesized by mixing pNP-β-Gal (1.0 mmol), sialic acid (1.2 mmol), cytidine triphosphate (1.2 mmol), CMP-sialic acid synthetases (CSS, 12 U), pyrophosphatase (PPA, 1U) and α-2,6-sialyltransferase (SiaT, 15U) in 15 mL Tris buffer (pH 7.0) with 5 mM MgCl$_2$ and 5 mM MnCl$_2$. After removal of the proteins by heating and centrifugation, the product was purified by (BIO-RAD) Biogel P-2 column chromatography using water as eluent. The fractions containing Neu5Ac-α2,6-Gal-pNP were collected, and lyophilized to give compound 1 (50%). $^1$H NMR (600 MHz, D$_2$O): δ 8.33-8.32 (m, 2H, Ar—H), 7.31-7.29 (m, 2H, Ar—H), 5.23 (d, J=7.8 Hz, C1-H$_β$), 4.06-4.04 (m, 2H), 3.99 (dd, J=10.2, 8.4 Hz, 1H), 3.90-3.86 (m, 3H), 3.83 (dd, J=10.2, 3.6 Hz, 1H), 3.80-3.76 (m, 1H), 3.73-3.69 (m, 3H), 3.65-3.62 (m, 2H), 3.57 (d, J=8.4 Hz, 1H), 2.79 (dd, J=12.6, 4.8 Hz, 1H), 2.04 (s, 3H, —CH$_3$), 1.68 (dd, J=12.6, 12.0 Hz, 1H); $^{13}$C NMR (150 MHz, D$_2$O): δ 174.6, 173.1, 161.4, 142.1, 125.7, 116.0, 99.8, 99.4, 73.6, 72.1, 71.9, 71.3, 69.8, 68.0, 67.7, 67.7, 62.5, 62.2, 51.4, 39.8, 21.6; HRMS (ESI-TOF) m/e: Calcd for $C_{23}H_{33}N_2O_{16}$ [M+H]$^+$: 593.1825 found 593.1825.

Example 2: Stability Against Sialidase-Catalyzed Hydrolysis and Analysis of Sialidase Inhibition[31]

Materials:

β-Galactosidase of *Aspergillus oryzae* (G5160) and sialidases from *Vibrio cholerae* (11080725001) and *Clostridium perfringens* (11585886001) were received from Sigma Aldrich.

Enzymatic Assays for Sialidases:

The assays were carried out at 37° C. in duplicates in 96-well plates in a final volume of 50 μL containing a substrate (0-20 mM), and β-galactosidase (100 mU). The assay conditions for the two sialidases were as follows: *C. perfringens* (1 mU), sodium acetate buffer (50 mM) pH 5.0 and CaCl$_2$) (10 mM); *V. cholerae* (2 mU), sodium acetate buffer (50 mM) pH 5.5, CaCl$_2$) (10 mM) and NaCl (150 mM). The reactions were carried out for 40 min to 2 hrs for *C. perfringens* and overnight for *V. cholerae*. The assays were stopped by adding 65 μL of CAPS buffer (N-cyclohexyl-3-aminopropane sulfonic acid, 0.5 M, pH 10.5). The amount of the para-nitrophenolate formed was determined by measuring the A405 nm of the reaction mixtures using a microplate reader. Three compounds (Neu5 Ac-α2,6-GalβpNP, 3F$^{ax}$-Neu5Ac-α2,6-GalβpNP and 3OH$^{eq}$-Neu5Ac-α2,6-GalβpNP) were tested as substrates for the enzymes. All three compounds have the background absorbance of A405 nm at 20 mM after incubation for 1 hr at 37° C. in the absence of sialidase. The absorbance of the three compounds Neu5Ac-α2,6-GalβpNP, 3F$^{ax}$-Neu5Ac-α2,6-GalβpNP and 3OH$^{eq}$-Neu5Ac-α2,6-GalβpNP were 0.044, 0.129 and 0.072, respectively. The standard curve of pNP was determined by series two-fold dilution of 0.35 mM of pNP, then graphing the A405 nm against the concentration of pNP resulted in the standard curve of pNP.

Inhibition Assays for Sialidases:

The assays were carried out at 37° C. in duplicates in 96-well plates in a final volume of 50 μL containing the substrate Neu5Ac-α2,6-GalβpNP (0.6 mM), β-galactosidase (100 mU), and sialidase in the absence or presence of an inhibitor at varied concentrations (0-20 mM). Reactions were allowed to proceed for 40 min to 2 hrs for *C. perfringens* and overnight for *V. cholera*. The assays were stopped by adding CAPS buffer (65 μL, 0.5 M, pH 10.5). The amount of the para-nitrophenolate formed was determined by measuring the A405 nm of the reaction mixture using a microplate reader (FIG. 1).

Example 3: Preparation of Homogeneous mAb Modified with 3F$^{ax}$-Neu5Ac and Neu5Ac to Study the Effect on Binding to FcγRIIIa by Surface Plasmon Resonance (SPR) Analysis Expression of Enzymes:

The endo-glycosidases Endo-S, Endo-S2, Endo-S2 mutant (D184Q), and the α-L-fucosidase from *Bacteroides fragilis* NCTC 9343 were expressed in *Escherichia coli* and the purification of enzymes was performed using Ni-NTA agarose beads.

Preparation of Mono-GlcNAc-Rituximab:

As described previously,[32] Rituximab (3.0 mg; Rituxan® Roche) in a Tris-HCl buffer (50 mM, pH 7.4, 1.5 mL) was incubated with Endo-S (120 μg), Endo-S2 (240 μg) and BfFucH (4.5 mg) at 37° C. for 24 h. LC-MS and SDS-PAGE analyses indicated the complete cleavage of the N-glycans on the heavy chain. The reaction mixture was subjected to affinity chromatography on a column of protein A-agarose resin (1 mL; GE Healthcare) pre-equilibrated with a Tris-HCl buffer (50 mM, pH 7.4). Then, the column was washed with a Tris-HCl buffer (50 mM, pH 7.4, 20 mL). The bound IgG was released with glycine-HCl (100 mM, pH 3.0, 10 mL), and the elution fractions were immediately neutralized with Tris-HCl buffer (1.0 M, pH 8.3). The fractions containing the antibody were combined and concentrated by centrifugal filtration (Amicon Ultra centrifugal filter, Millipore, Billerica, MA) to give mono-GlcNAc Rituximab (2.4 mg). The product was trypsinized, and the glycopeptides, TKPREEQYNSTYR (m/z=1391.58) and EEQYNSTYR (m/z=1873.88) were analyzed using nanospray LC/MS to confirm the glycosylation pattern of mono-GlcNAc.

Transglycosylation of Mono-GlcNAc Rituximab with Glycan Oxazolines:

A glycan oxazoline was added to the mixture of an Endo-S2 D184Q and Mono-GlcNAc Rituximab in 50 mM Tris buffer (pH 7.4). The solution was incubated for 30 min at 37° C. Then, the reaction mixture was purified with protein-A affinity column, followed by an anion exchange column of Capto Q (GE Healthcare) to collect the desired product.

Figure 2:
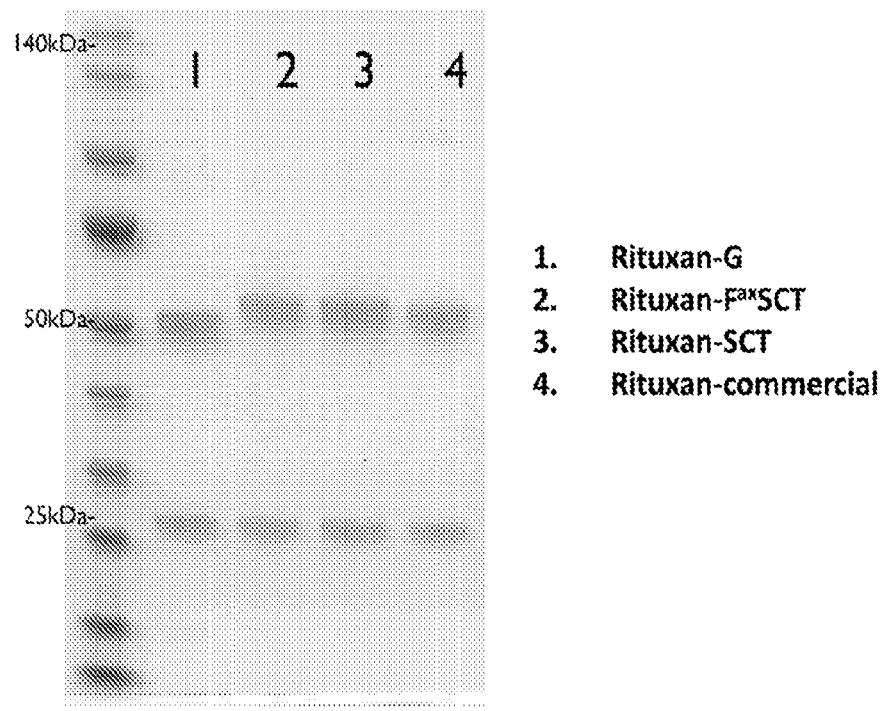
FIG. 2 is a stained electrophoresis gel of four N-glycans: (1) rituxan-G, (2) rituxan-$F^{ax}$-SCT, (3) rituxan-SCT, and (4) commercial rituxan.

SDS-PAGE Detection of Glycoengineered Herceptin Antibodies:

All the SDS-PAGE analyses were performed with NuPAGE® Novex® 4-12% Bis-Tris gel (Invitrogen) in MOPS buffer with 2-mercaptoethanol present in samples (FIG. 2).

Figure 3:
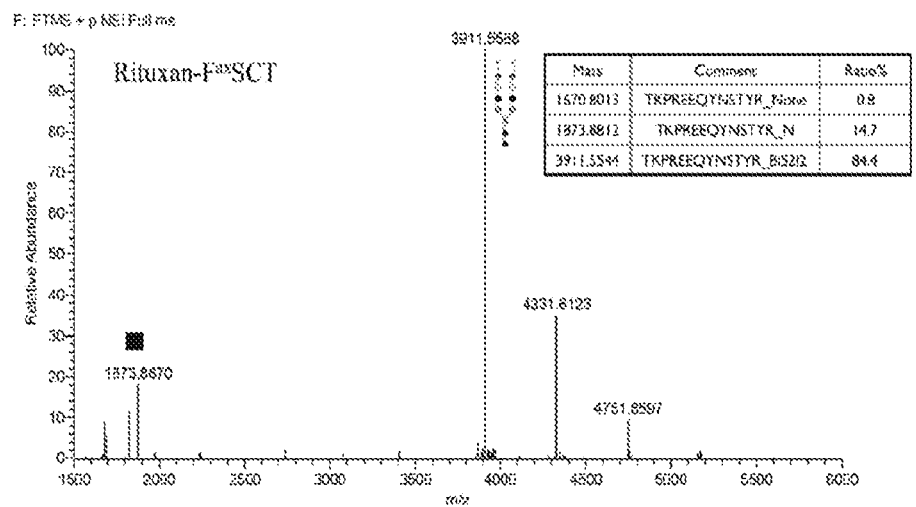
FIG. 3 shows mass spectra obtained for three N-glycans, i.e., rituxan-$F^{ax}$-SCT, rituxan-SCT, and rituxan.
Figure 3:
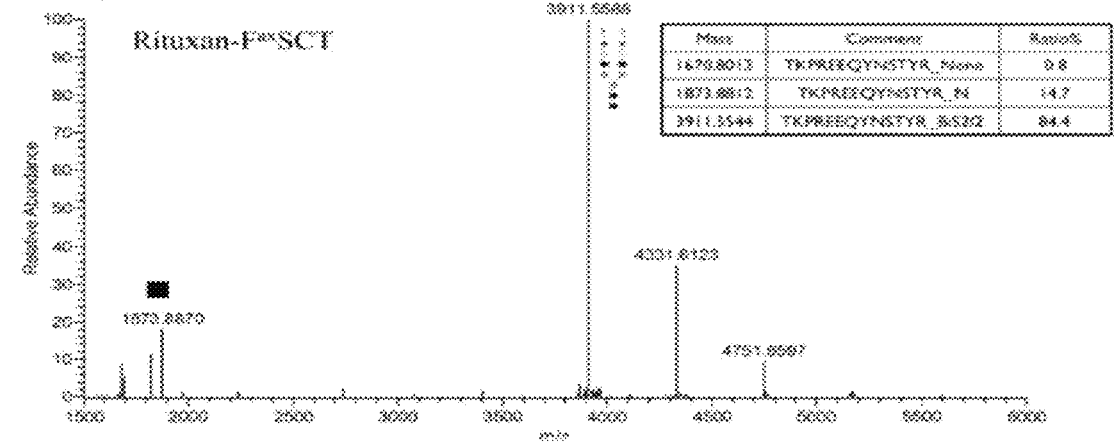
Figure 3:
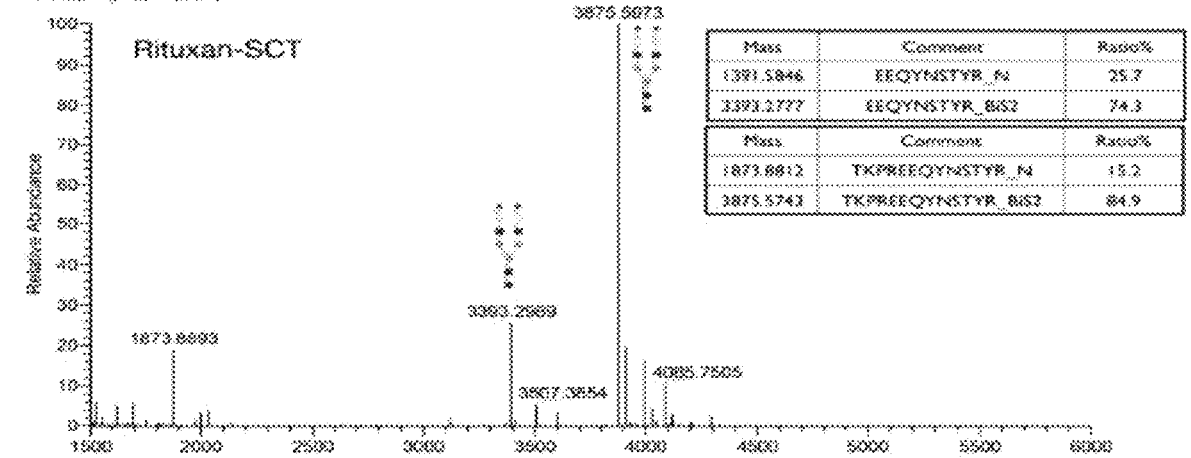
Figure 3:
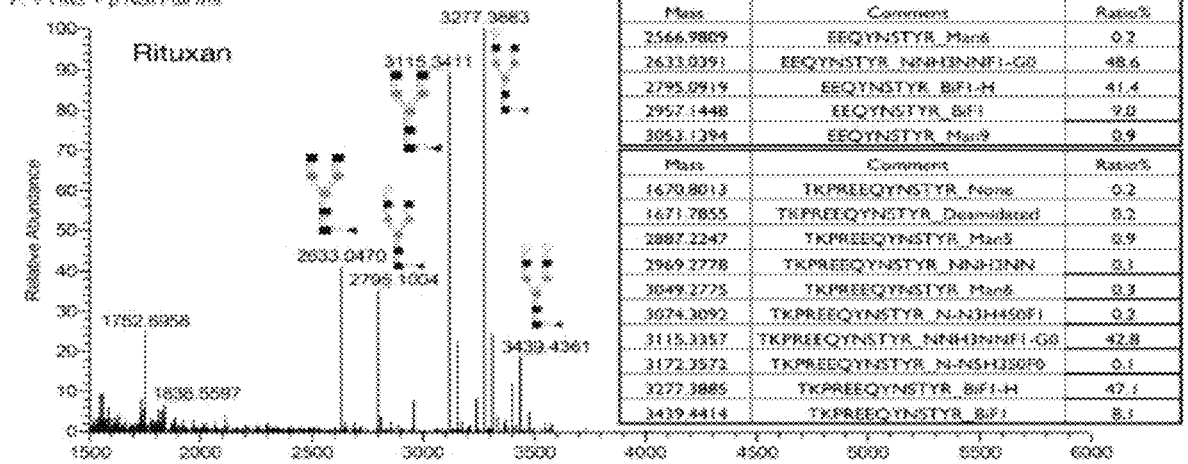

MS Spectrometry Analysis of Glycoengineered mAb:

For the analysis of trypsinized glycopeptides, high resolution and high mass accuracy nanoflow LC-MS/MS experiments were performed on a LTQFT Ultra (linear quadrupole ion trap Fourier transform ion cyclotron resonance) mass spectrometer (Thermo Electron, San Jose, CA) equipped with a nanoelectrospry ion source (New Objective, Inc.), an Agilent 1100 Series binary high-performance liquid chromatography pump (Agilent Technologies, Palo Alto, CA), and a Famos autosampler (LC Packings, San Francisco, CA). The digestion solution (6 μL) was injected at the 10 μL/min flow rate to a self-packed precolumn (150 μm I.D.×20 mm, 5 μm, 100 Å). The chromatographic separation was performed on a self-packed reversed phase C18 nano-column (75 μm I.D.×300 mm, 5 μm, 100 Å) using 0.1% formic acid in water as a mobile phase A and 0.1% formic acid in 80% acetonitrile as mobile phase B operated at 300 nL/min flow rate. Survey of full-scan MS conditions: mass range m/z 320-2000, resolution 100,000 at m/z 400. The ten most intense ions were sequentially isolated for MS2 by LTQ. Electrospray voltage was maintained at 1.8 kV and the capillary temperature was set at 200° C. (FIG. 3 and Table 3).

Surface Plasmon Resonance (SPR) Analysis

All the SPR experiments were performed with the single cycle kinetic method by BIACORE T200 at 25° C. using HBS-EP (10 mM HEPES pH7.4, 0.15M NaCl, 3mMEDTA, 0.005% surfactant P20) as running buffer. FcγRIIIa was transfected into HEK-293 cells to express the complex-type glycosylated recombinant protein as analyte. For the analysis of Rituximabs binding to FcγRIIIa receptor, antihuman Fab antibodies in human Fab capture kit (GE Healthcare) were immobilized onto both the reference and active channels of CM5 sensor chip, and then Rituximabs were captured on the active channel for interacting with the serial dilutions of FcγRIIIa analyte (2.5, 5, 10, 20, 40 nM for 2,6-FluoSCT and 2,6-SCT; 8, 24, 72, 216, 648 nM for the commercial Rituximabs) at 30 μl/min for association of 240 seconds followed by dissociation time of 420 seconds. Rituximab data were processed with double referencing for background subtraction. Data of Rituximabs was fitted to 1:1 Langmuir binding model in BiaEvaluation software (GE Healthcare) to obtain the kinetic/affinity constants (Table 4). Analyzed antibodies were captured by the Human Fab capture kit and detected with the single cycle kinetic method.

TABLE 3

Calibration of N-glycan Relative Abundance[33]

| Rit-F$^{ax}$SCT Concentrate | Rit-SCT Concentrate | % |  |
|---|---|---|---|
| 1.0 | 0.0 | none |  |
| 1.7 | 1.8 | Rit-GlcNa |  |
| 0.0 | 98.2 | Rit-SCT |  |
| 97.3 | 0.0 | Rit-FluoSCT |  |

TABLE 4

Binding Avidity of Glycoengineered Rituximab IgG1 to FcγRIIIa Measured by SPR

| Sample | ka (1/Ms) | kd (1/s) | KD (M) | Rmax (RU) | Fold |
|---|---|---|---|---|---|
| Rituximab | 2.31E+05 | 0.07054 | 3.06E−07 | 32.33 | 1-fold |
| 2,6-F$^{ax}$SCT | 2.44E+05 | 0.001996 | 8.18E−09 | 71.28 | 37.4-fold |
| 2,6-SCT | 2.68E+05 | 0.002059 | 7.67E−09 | 60.64 | 39.9-fold |

Example 4: Relative Reactivity Values (RRV) of Compounds 4 and 18

The RRVs were measured in triplicates by following the experimental procedure reported previously.[34] The RRV (2053) of disaccharide donor 4 was measured against a competition reference donor S3423 (RRV=1791). The RRV (537) of disaccharide donor 18 was measured against a competition reference donor S23 (RRV=286).

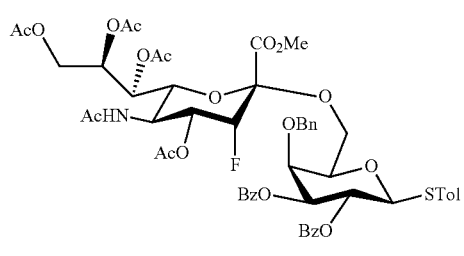

4

RRV = 2053

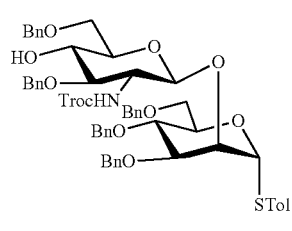

18

RRV = 537

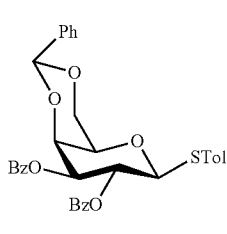

S5

RRV = 286

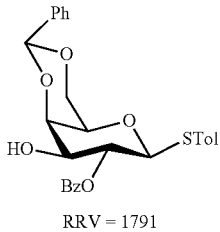

S34

RRV = 1791

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

REFERENCES (1) Varki, A. Sialic acids in human health and disease. *Trends Mol. Med.* 2008, 14, 351.
(2) (a) Liu, Y.-C.; Yen, H.-Y.; Chen, C.-Y.; Chen, C.-H.; Cheng, P.-F.; Juan, Y.-H.; Chen, C.-H.; Khoo, K.-H.; Yu, C.-J.; Yang, P.-C.; Hsu, T.-L.; Wong, C.-H. Sialylation and fucosylation of epidermal growth factor receptor suppress its dimerization and activation in lung cancer cells. *Proc. Natl. Acad. Sci. U.S.A.* 2011, 108, 11332. (b) Yen, H.-Y.; Liu, Y.-C.; Chen, N.-Y.; Tsai, C.-F.; Wang, Y.-T.; Chen, Y.-J.; Hsu, T.-L.; Yang, P.-C.; Wong, C.-H. Effect of sialylation on EGFR phosphorylation and resistance to tyrosine kinase inhibition. *Proc. Natl. Acad. Sci. U.S.A.* 2015, 112, 6955.
(3) (a) Ashwell, G.; Harford, J. Carbohydrate-specific receptors of the liver. *Annu. Rev. Biochem.* 1982, 51, 531. (b) Weigel, P. H.; Yik, J. H. Glycans as endocytosis signals:

the cases of the asialoglycoprotein and hyaluronan/chondroitin sulfate receptors. *Biochim. Biophys. Acta* 2002, 1572, 341.

(4) (a) Wang, Z.; Chinoy, Z. S.; Ambre, S. G.; Peng, W.; McBride, R.; de Vries, R. P.; Glushka, J.; Paulson, J. C.; Boons, G. J. A general strategy for the chemoenzymatic synthesis of asymmetrically branched N-glycans. *Science* 2013, 341, 379. (b) Shivatare, S. S.; Chang, S. H.; Tsai, T. I.; Tseng, S. Y.; Shivatare, V. S.; Lin, Y. S.; Cheng, Y. Y.; Ren, C. T.; Lee, C. C.; Pawar, S.; Tsai, C. S.; Shih, H. W.; Zeng, Y. F.; Liang, C. H.; Kwong, P. D.; Burton, D. R.; Wu, C. Y.; Wong, C. H. Modular synthesis of N-glycans and arrays for the hetero-ligand binding analysis of HIV antibodies. *Nat. Chem.* 2016, 8, 338. (c) Li, L.; Liu, Y.; Ma, C.; Qu, J.; Calderon, A. D.; Wu, B.; Wei, N.; Wang, X.; Guo, Y.; Xiao, Z.; Song, J.; Sugiarto, G.; Li, Y.; Yu, H.; Chen, X.; Wang, P. G. Efficient chemoenzymatic synthesis of an N-glycan isomer library. *Chem. Sci.* 2015, 6, 5652.

(5) Li, C.; Wang, L.-X. Chemoenzymatic Methods for the Synthesis of Glycoproteins. *Chem. Rev.* 2018, 118, 8359.

(6) (a) Lin, C.-W.; Tsai, M.-H.; Li, S.-T.; Tsai, T.-I.; Chu, K.-C.; Liu, Y.-C.; Lai, M.-Y.; Wu, C.-Y.; Tseng, Y.-C.; Shivatare, S. S.; Wang, C.-H.; Chao, P.; Wang, S.-Y.; Shih, H.-W.; Zeng, Y.-F.; You, T.-H.; Liao, J.-Y.; Tu, Y.-C.; Lin, Y.-S.; Chuang, H.-Y.; Chen, C.-L.; Tsai, C.-S.; Huang, C.-C.; Lin, N.-H.; Ma, C.; Wu, C.-Y.; Wong, C.-H. A common glycan structure on immunoglobulin G for enhancement of effector functions. *Proc. Natl. Acad. Sci. U.S.A.* 2015, 112, 10611. (b) Tsai, T.-I.; Li, S.-T.; Liu, C.-P.; Chen, K. Y.; Shivatare, S. S.; Lin, C.-W.; Liao, S.-F.; Lin, C.-W.; Hsu, T.-L.; Wu, Y.-T.; Tsai, M.-H.; Lai, M.-Y.; Lin, N.-H.; Wu, C.-Y.; Wong, C.-H. An Effective Bacterial Fucosidase for Glycoprotein Remodeling. *ACS Chem. Biol.* 2017, 12, 63. (c) Liu, C.-P.; Tsai, T.-I.; Cheng, T.; Shivatare, V. S.; Wu, C.-Y.; Wu, C.-Y.; Wong, C.-H. Glycoengineering of antibody (Herceptin) through yeast expression and in vitro enzymatic glycosylation. *Proc. Natl. Acad. Sci. U.S.A.* 2018, 115, 720.

(7) (a) Gantt, R.; Millner, S.; Binkley, S. B. Inhibition of N-Acetylneuraminic Acid Aldolase by 3-Fluorosialic Acid. Biochemistry 1964, 3, 1952. (b) Hagiwara, T.; Kijima-Suda, I.; Ido, T.; Ohrui, H.; Tomita, K. Inhibition of bacterial and viral sialidases by 3-fluoro-N-acetyl-neuraminic acid. *Carbohydr. Res.* 1994, 263, 167. (c) Burkart, M. D.; Zhang, Z.; Hung, S.-C.; Wong, C.-H. A New Method for the Synthesis of Fluoro-Carbohydrates and Glycosides Using Selectfluor. *J. Am. Chem. Soc.* 1997, 119, 11743. (d) D. Burkart, M.; P. Vincent, S.; Wong, C.-H. An efficient synthesis of CMP-3-fluoroneuraminic acid. *Chem. Commun.* 1999, 1525. (e) Burkart, M. D.; Vincent, S. P.; Duffels, A.; Murray, B. W.; Ley, S. V.; Wong, C.-H. Chemoenzymatic synthesis of fluorinated sugar nucleotide: useful mechanistic probes for glycosyltransferases. *Bioorg. Med. Chem.* 2000, 8, 1937. (f) Sun, X.-L.; Kanie, Y.; Guo, C.-T.; Kanie, O.; Suzuki, Y.; Wong, C.-H. Syntheses of C-3-Modified Sialylglycosides as Selective Inhibitors of Influenza Hemagglutinin and Neuraminidase. *Eur. J. Org. Chem.* 2000, 2643. (g) Rillahan, C. D.; Antonopoulos, A.; Lefort, C. T.; Sonon, R.; Azadi, P.; Ley, K.; Dell, A.; Haslam, S. M.; Paulson, J. C. Global metabolic inhibitors of sialyl- and fucosyltransferases remodel the glycome. *Nat. Chem. Biol.* 2012, 8, 661.

(8) Ishiwata, K.; Ido, T.; Nakajima, T.; Ohrui, H.; Kijima-Suda, I.; Itoh, M. Tumor uptake study of 18F-labeled N-acetylneuraminic acids. International journal of radiation applications and instrumentation. *Int. J. Rad. Appl. Instrum. B* 1990, 17, 363.

(9) (a) Watts, A. G.; Damager, I.; Amaya, M. L.; Buschiazzo, A.; Alzari, P.; Frasch, A. C.; Withers, S. G. *Trypanosoma cruzi* Trans-sialidase Operates through a Covalent Sialyl-Enzyme Intermediate: Tyrosine Is the Catalytic Nucleophile. *J. Am. Chem. Soc.* 2003, 125, 7532. (b) Buchini, S.; Gallat, F. X.; Greig, I. R.; Kim, J. H.; Wakatsuki, S.; Chavas, L. M.; Withers, S. G. Tuning Mechanism-Based Inactivators of Neuraminidases: Mechanisticand Structural Insights. *Angew. Chem. Int. Ed. Engl.* 2014, 53, 3382. (c) Kim, J. H.; Resende, R.; Wennekes, T.; Chen, H. M.; Bance, N.; Buchini, S.; Watts, A. G.; Pilling, P.; Streltsov, V. A.; Petric, M.; Liggins, R.; Barrett, S.; McKimm-Breschkin, J. L.; Niikura, M.; Withers, S. G. Mechanism-Based Covalent Neuraminidase Inhibitors with Broad-Spectrum Influenza Antiviral Activity. *Science* 2013, 340, 71.

(10) Tsai, C. S.; Yen, H. Y.; Lin, M. I.; Tsai, T. I.; Wang, S. Y.; Huang, W. I.; Hsu, T. L.; Cheng, Y. S.; Fang, J. M.; Wong, C.-H. Cell-permeable probe for identification and imaging of sialidases. *Proc. Natl. Acad. Sci. U.S.A.* 2013, 110, 2466.

(11) (a) Chokhawala, H. A.; Cao, H.; Yu, H.; Chen, X. Enzymatic Synthesis of Fluorinated Mechanistic Probes for Sialidases and Sialyltransferases. *J. Am. Chem. Soc.* 2007, 129, 10630. (b) McArthur, J. B.; Yu, H.; Zeng, J.; Chen, X. Converting *Pasteurella multocida* α2-3-sialyltransferase 1 (PmST1) to a regioselective α2,6-sialyltransferase by saturation mutagenesis and regioselective screening. *Org. Biomol. Chem.,* 2017, 15, 1700.

(12) Petrie, C. R.; Sharma, M.; Simmons, O. D.; Korytnyk, W. Synthesis of analogs of N-acetylneuraminic acid and their effect on CMP-sialate synthase. *Carbohydr. Res.* 1989, 186, 326.

(13) Nakajima, T.; Hori, H.; Ohrui, H.; Meguro, H.; Ido, T. Synthesis of N-Acetyl-3-fluoro-neuraminic Acids *Agric. Biol. Chem.* 1988, 52, 1209.

(14) Watts, A. G.; Withers, S. G. The synthesis of some mechanistic probes for sialic acid processing enzymes and the labeling of a sialidase from *Trypanosoma rangeli*. *Can. J. Chem* 2004, 82, 1581.

(15) Hayashi, T.; Kehr, G.; Gilmour R. Stereospecific α-sialylation by site-selective fluorination. *Angew. Chem. Int. Ed. Engl.* 10.1002/anie.201812963.

(16) Okamoto, K.; Kondo, T.; Goto, T. An effective synthesis of α-glycosides of N-acetylneuraminic acid derivatives by use of 2-deoxy-2β-halo-3β-hydroxy-4,7,8,9-tetra-O-acetyl-N-acetylneuraminic acid methyl ester. *Tetrahedron* 1987, 43, 5919.

(17) Bennua-Skalmowski, B.; Vorbrüggen, H. A facile conversion of primary or secondary alcohols with n-perfluorobutane-sulfonyl fluoride/1,8-diazabicyclo[5.4.0]undec-7-ene into their corresponding fluorides. *Tetrahedron Lett.* 1995, 36, 2611.

(18) Cao, H.; Li, Y.; Lau, K.; Muthana, S.; Yu, H.; Cheng, J.; Chokhawala, H. A.; Sugiarto, G.; Zhang, L.; Chen, X. Sialidase substrate specificity studies using chemoenzymatically synthesized sialosides containing C5-modified sialic acids. *Org. Biomol. Chem.,* 2009, 7, 5137.

(19) Orlova, A. V.; Shpirt, A. M.; Kulikova, N. Y.; Kononov, L. O. N,N-Diacetylsialyl chloride—a novel readily accessible sialyl donor in reactions with neutral and charged nucleophiles in the absence of a promoter. *Carbohydr. Res.* 2010, 345, 721.

(20) Okamoto, K.; Kondo, T.; Goto. T. Functionalization of 2-Deoxy-2,3-dehydro-N-acetylneuraminic Acid Methyl Ester. *Bull. Chem. Soc. Jpn.* 1987, 60, 631.

(21) Pascolutti, M.; Madge, P. D.; Thomson, R. J.; von Itzstein, M. Access to 3-O-Functionalized N-Acetylneuraminic Acid Scaffolds. *J. Org. Chem.* 2015, 80, 7746.

(22) Wang, C.-C.; Lee, J.-C.; Luo, S.-Y.; Kulkarni, S. S.; Huang, Y.-W.; Lee, C.-C.; Chang, K.-L.; Hung, S.-C. Regioselective one-pot protection of carbohydrates. *Nature* 2007, 446, 896.

(23) Zhang, Z.; Ollmann, I. R.; Ye, X.-S.; Wischnat, R.; Baasov, T.; Wong, C.-H. Programmable One-Pot Oligosaccharide Synthesis. *J. Am. Chem. Soc.* 1999, 121, 734.

(24) Huang, L.; Huang, X. Highly Efficient Syntheses of Hyaluronic Acid Oligosaccharides. *Chem. Eur. J.* 2007, 13, 529.

(25) Shivatare, S. S.; Chang, S.-H.; Tsai, T.-I; Ren, C.-T.; Chuang, H.-Y.; Hsu, L.; Lin, C.-W.; Li, S.-T.; Wu, C.-Yi; Wong, C.-H. Efficient Convergent Synthesis of Bi—, Tri-, and Tetra-antennary

(26) Complex Type N-Glycans and Their HIV-1 Antigenicity. *J. Am. Chem. Soc.* 2013, 135, 15382.

(27) Shivatare, S. S.; Chang, S.-H.; Tsai, T.-I; Tseng, S. Y.; Shivatare, V. S.; Lin, Y.-S.; Cheng, Y.-Y.; Ren, C.-T.; Lee, C.-C. D.; Pawar, S.; Tsai, C.-S.; Shih, H.-W.; Zeng, Y.-F.; Liang, C.-H.; Kwong, P. D.; Burton, D. R.; Wu, C.-Y.; Wong, C.-H. Modular synthesis of N-glycans and arrays for the hetero-ligand binding analysis of HIV antibodies. *Nat. Chem.* 2016, 8, 338.

(28) Mong, T. K.-K.; Huang, C.-Y.; Wong, C.-H. A New Reactivity-Based One-Pot Synthesis of N-Acetyllactosamine Oligomers. *J. Org. Chem.* 2003, 68, 2135.

(29) Dinkelaar, J.; Duivenvoorden, B. A.; Wennekes, T.; Overkleeft, H. S.; Boot, R. G.; Aerts, J. M. F. G.; Codée, J. D. C.; van der Marel, G. A. A Preparative Synthesis of Human Chitinase Fluorogenic Substrate (4'-Deoxychitobiosyl)-4-methylumbelliferone. *Eur. J. Org. Chem.* 2010, 2565.

(30) Chayajarus, K.; Chambers, D. J.; Chughtai, M. J.; Fairbanks, A. J. Stereospecific Synthesis of 1,2-cis Glycosides by Vinyl-Mediated IAD. *Org. lett.* 2004, 6, 3797-3800.

(31) Cao, H.; Li, Y.; Lau, K.; Muthana, S.; Yu, H.; Cheng, J.; Chokhawala, H. A.; Sugiarto, G.; Zhang, L.; Chen, X. Sialidase substrate specificity studies using chemoenzymatically synthesized sialosides containing C5-modified sialic acids. *Org. Biomol. Chem.*, 2009, 7, 5137.

(32) Lin, C.-W.; Tsai, M.-H.; Li, S.-T.; Tsai, T.-I.; Chu, K.-C.; Liu, Y.-C.; Lai, M.-Y.; Wu, C.-Y.; Tseng, Y.-C.; Shivatare, S. S.; Wang, C.-H.; Chao, P.; Wang, S.-Y.; Shih, H.-W.; Zeng, Y.-F.; You, T.-H.; Liao, J.-Y.; Tu, Y.-C.; Lin, Y.-S.; Chuang, H.-Y.; Chen, C.-L.; Tsai, C.-S.; Huang, C.-C.; Lin, N.-H.; Ma, C.; Wu, C.-Y.; Wong, C.-H. A common glycan structure on immunoglobulin G for enhancement of effector functions. *Proc. Natl. Acad. Sci. U.S.A.* 2015, 112, 10611.

(33) Stavenhagen, K.; Hinneburg, H.; Thaysen-Andersen, M.; Hartmann, L.; Silva, D. V.; Fuchser, J.; Kaspar, S.; Rapp, E.; Seebergera, P. H.; Kolaricha D. Quantitative mapping of glycoprotein micro-heterogeneity and macro-heterogeneity: an evaluation of mass spectrometry signal strengths using synthetic peptides and glycopeptides. *J. Mass Spectrom.* 2013, 48, 627.

(34) Lee, J.-C.; Greenberg, W. A; Wong, C.-H. Programmable reactivity-based one-pot oligosaccharide synthesis. *Nat. Protoc.* 2006, 1, 3143.

What is claimed is:

1. A method of preparing a saccharide containing a 3-fluoro-sialic acid, the method comprising:
conducting a glycosylation reaction by reacting a 3-hydroxy-sialic acid with a saccharide to form an α2,6-linked 3-hydroxy-sialoside, wherein:
the 3-hydroxy-sialic acid is of formula (I):

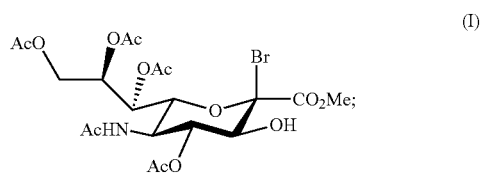

the saccharide is a compound of formula (II):

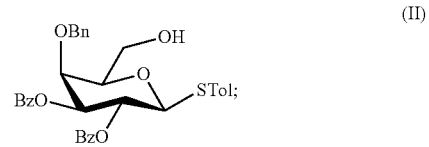

and
the α2,6-linked 3-hydroxy-sialoside is a compound of formula (III):

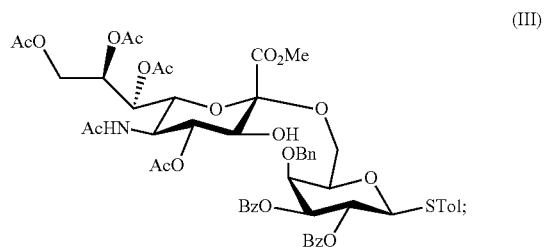

and
conducting a fluorination reaction by reacting the α2,6-linked 3-hydroxy-sialoside with a fluorinating agent to form a saccharide containing a 3-fluoro-sialic acid, wherein the saccharide containing a 3-fluoro-sialic acid is a compound of formula (IV):

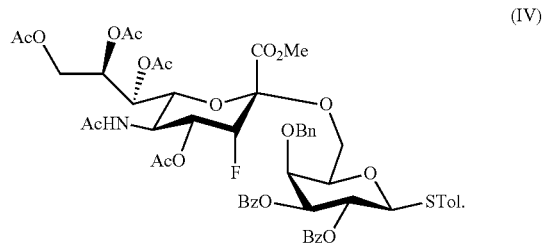

2. The method of claim 1, wherein the fluorinating agent is perfluoro-1-butanesulfonyl fluoride (NfF), and the fluorination reaction is conducted in the presence of a catalyst, wherein the catalyst is 1,8-diazabicyclo[5,4,0]-undec-7-ene (DBU) and the fluorination reaction is optionally conducted in toluene, wherein the fluorination reaction is conducted further in the presence of tris(dimethylamino)sulfonium difluorotrimethylsilicate (TASF).

3. The method of claim 1, wherein the fluorinating agent is NfF, the glycosylation reaction is conducted in the presence of AgOTf and $Na_2HPO_4$, and the fluorination reaction is conducted in the presence of a catalyst.

4. The method of claim 3, wherein the catalyst is DBU and each of the glycosylation and fluorination reactions is conducted in toluene and wherein the fluorination reaction is conducted further in the presence of TASF.

5. The method of claim 1, further comprising conducting another glycosylation reaction by reacting the saccharide containing a 3-fluoro-sialic acid with a second saccharide, wherein the fluorinating agent is NfF, the glycosylation reaction is conducted in the presence of AgOTf and $Na_2HPO_4$, and the fluorination reaction is conducted in the presence of a catalyst; wherein the catalyst is DBU and each of the glycosylation and fluorination reactions is conducted in toluene, and wherein the fluorination reaction is optionally conducted further in the presence of TASF.

6. A method of preparing a homogeneous antibody bonded to a saccharide containing a 3-fluoro-sialic acid, comprising:
   preparing a saccharide containing a 3-fluoro-sialic acid according to claim 1; and
   glycosylating a monoclonal antibody with said saccharide containing a 3-fluoro-sialic acid.

7. The method of claim 6, wherein the fluorinating agent is NfF, the glycosylation reaction is conducted in the presence of AgOTf and $Na_2HPO_4$, and the fluorination reaction is conducted in the presence of a catalyst, wherein the catalyst is DBU and each of the glycosylation and fluorination reactions is conducted in toluene, and
   optionally further comprising after the fluorination reaction, conducting another glycosylation reaction by reacting the saccharide containing a 3-fluoro-sialic acid with a second saccharide.

* * * * *